* (12) United States Patent
Rasgon et al.

(10) Patent No.: US 12,391,962 B2
(45) Date of Patent: Aug. 19, 2025

(54) TARGETING PEPTIDE TO DELIVER A COMPOUND TO OOCYTES

(71) Applicant: THE PENN STATE RESEARCH FOUNDATION, University Park, PA (US)

(72) Inventors: Jason Laurence Rasgon, State College, PA (US); Duverney De Jesus Chaverra Rodriguez, State College, PA (US); Grant Leslie Hughes, Wirral (GB); Chan Chin Heu, Bellefonte, PA (US)

(73) Assignee: THE PENN STATE RESEARCH FOUNDATION, University Park (PA)

( * ) Notice: Subject to any disclaimer, the term of this patent is extended or adjusted under 35 U.S.C. 154(b) by 1459 days.

(21) Appl. No.: 15/929,408

(22) Filed: Apr. 30, 2020

(65) Prior Publication Data

US 2020/0299731 A1 Sep. 24, 2020

Related U.S. Application Data

(63) Continuation of application No. PCT/US2018/057988, filed on Oct. 29, 2018.

(60) Provisional application No. 62/578,805, filed on Oct. 30, 2017.

(51) Int. Cl.
| | | |
|---|---|---|
| *C12N 15/90* | (2006.01) | |
| *A01K 67/68* | (2025.01) | |
| *C07K 14/435* | (2006.01) | |
| *C12N 9/22* | (2006.01) | |

(52) U.S. Cl.
CPC ............ *C12N 15/902* (2013.01); *A01K 67/68* (2025.01); *C12N 9/22* (2013.01); *A01K 2217/072* (2013.01); *A01K 2227/706* (2013.01); *C07K 14/43581* (2013.01); *C12N 2310/20* (2017.05); *Y02A 50/30* (2018.01)

(58) Field of Classification Search
CPC .... C12N 15/902; C12N 9/22; A01K 67/0339; A01K 2227/706; C07K 14/43563
USPC .................................................. 435/455, 440
See application file for complete search history.

(56) References Cited

U.S. PATENT DOCUMENTS

2005/0208558 A1* 9/2005 Venter .................. C12Q 1/6888
435/6.16
2007/0275037 A1 11/2007 Ding et al.

FOREIGN PATENT DOCUMENTS

| WO | 2004003157 A2 | 1/2004 |
| WO | 2016073433 A1 | 5/2016 |
| WO | 2017024343 A1 | 2/2017 |

OTHER PUBLICATIONS

Izumi et al., "Design of Peptide-based Inhibitors for Human Immunodeficiency Virus Type 1 Strains Resistant to T-20". The Journal of Biological Chemistry. Feb. 20, 2009. (284):8, 4914-4920 (Year: 2009).*
Bownes et al., "*Drosophila* yolk protein produced in E. coli is accumulated by mosquito ovaries". Insect Mol Biol. Oct. 2002; 11(5): 487-96. (Year: 2002).*
Grant et al. "Receptor-mediated endocytosis in the Caenorhabditis elegans oocyte". Mol Biol Cell. Dec. 1999; 10(12):4311-26. doi: 10.1091/mbc.10.12.4311. (Year: 1999).*
Kathryn et al., "Genome Engineering with CRISPR-Cas9 in the Mosquito *Aedes aegypti*". Cell Rep. Apr. 7, 2015;11(1):51-60. (Year: 2015).*
Armbruster, Peter A., "Molecular pathways to nonbiting mosquitoes", PNAS, vol. 115, No. 5, 3 pages, Jan. 30, 2018.
Boudko et al., "Substrate specificity and transport mechanism of amino-acid transceptor Slimfast from Aedes aegypti", Nature Communications, 6:8546, 10 pages, Oct. 9, 2015.
Bownes et al., "*Drosophila* yolk protein produced in E. coli is accumulated by mosquito ovaries", Insect Mol. Biol., vol. 11(5), pp. 487-496, Oct. 2002.
Chaverra-Rodriguez et al., "Targeted delivery of CRISPR-Cas9 ribonucleoprotein into arthropod ovaries for heritable germline gene editing", Nature Communications, 9:3008, 11 pages, 2018.
Gantz et al., "Highly efficient Cas9-mediated gene drive for population modification of the malaria vector mosquito *Anopheles stephensi*", PNAS, www.pnas.org/cgi/doi/10.1073/pnas.1521077112, 8 pages, published online Nov. 23, 2015.
Hammond et al., "A CRISPR-Cas9 gene drive system targeting female reproduction in the malaria mosquito vector *Anopheles gambiae*", Nature Biotechnology, vol. 34, No. 1, pp. 78-85, Jan. 2016.
Herren et al., "Vertical Transmission of a Drosophila Endosymbiont Via Cooption of the Yolk Transport and Internalization Machinery", Mbio., vol. 4, Issue 2, 8 pages, Mar. 2013.

(Continued)

*Primary Examiner* — Allison M Fox
*Assistant Examiner* — Hanan Isam Abuzeineh
(74) *Attorney, Agent, or Firm* — McKee, Voorhees & Sease, PLC

(57) ABSTRACT

Methods of targeting a molecule of interest to the oocyte of an animal are shown. In an embodiment the method utilizes a receptor binding region of a yolk protein precursor. In embodiment the yolk protein precursor is a YP1 sequence, functional fragment of functional variant thereof. The targeting molecule is linked to the molecule of interest. The molecule of interest may be a molecule of a gene editing system, such as CRISPR/Cas and in an embodiment comprises Cas. The methods and composition are useful for targeting a molecule of interest to an animal, such as an invertebrate or insect.

22 Claims, 26 Drawing Sheets
(12 of 26 Drawing Sheet(s) Filed in Color)
Specification includes a Sequence Listing.

(56) References Cited

OTHER PUBLICATIONS

International Searching Authority in connection with PCT/US2018/057988 filed Oct. 29, 2018, "The International Search Report and the Written Opinion of the International Searching Authority, or the Declaration", 19 pages, mailed Feb. 19, 2019.

Jinek et al., "A programmable dual RNA-guided DNA endonuclease in adaptive bacterial immunity", Science, 337 (6096), pp. 816-821, Aug. 17, 2012.

Kistler et al., "Genome Engineering with CRISPR-Cas9 in the Mosquito *Aedes aegypti*", CellPress, vol. 11, 40 pages, Apr. 7, 2015.

Li et al., "Germline Cas9 expression yields highly efficient genome engineering in a major worldwide disease vector, Aedes aegypti", PNAS, www.pnas.org/cgi/doi/10.1073/pnas.1711538114, 10 pages, Oct. 23, 2017.

Li et al., "Receptor-Ligand Interaction between Vitellogenin Receptor (VtgR) and Vitellogenin (Vtg), Implications on Low Density Lipoprotein Receptor and Apolipoprotein B/E", Journal of Biological Chemistry, vol. 278, No. 5, pp. 2799-2806, Jan. 31, 2003.

Rungger et al., "Oocyte shuttle, a recombinant protein transporting donor DNA into the Xenopus oocyte in situ", The Company of Biologists, vol. 6, pp. 290-295, Jan. 4, 2017.

Terenius et al., "Molecular Genetic Manipulation of Vector Mosquitoes", Cell Host & Microbe, vol. 4, pp. 417-423, Nov. 13, 2008.

\* cited by examiner

SEQUENCE LISTING

<160> NUMBER OF SEQ ID NOS: 75

<210> SEQ ID NO 1
<211> LENGTH: 439
<212> TYPE: PRT
<213> ORGANISM: Drosophila melanogaster

<400> SEQUENCE: 1

```
Met Asn Pro Met Arg Val Leu Ser Leu Leu Ala Cys Leu Ala Val Ala
1               5                   10                  15

Ala Leu Ala Lys Pro Asn Gly Arg Met Asp Asn Ser Val Asn Gln Ala
            20                  25                  30

Leu Lys Pro Ser Gln Trp Leu Ser Gly Ser Gln Leu Glu Ala Ile Pro
        35                  40                  45

Ala Leu Asp Asp Phe Thr Ile Glu Arg Leu Glu Asn Met Asn Leu Glu
    50                  55                  60
```

```
Arg Gly Ala Glu Leu Leu Gln Gln Val Tyr His Leu Ser Gln Ile His
 65                  70                  75                  80

His Asn Val Glu Pro Asn Tyr Val Pro Ser Gly Ile Gln Val Tyr Val
                 85                  90                  95

Pro Lys Pro Asn Gly Asp Lys Thr Val Ala Pro Leu Asn Glu Met Ile
            100                 105                 110

Gln Arg Leu Lys Gln Lys Gln Asn Phe Gly Glu Asp Glu Val Thr Ile
        115                 120                 125

Ile Val Thr Gly Leu Pro Gln Thr Ser Glu Thr Val Lys Lys Ala Thr
    130                 135                 140

Arg Lys Leu Val Gln Ala Tyr Met Gln Arg Tyr Asn Leu Gln Gln Gln
145                 150                 155                 160

Arg Gln His Gly Lys Asn Gly Asn Gln Asp Tyr Gln Asp Gln Ser Asn
                165                 170                 175

Glu Gln Arg Lys Asn Gln Arg Thr Ser Ser Glu Glu Asp Tyr Ser Glu
            180                 185                 190

Glu Val Lys Asn Ala Lys Thr Gln Ser Gly Asp Ile Ile Val Ile Asp
        195                 200                 205

Leu Gly Ser Lys Leu Asn Thr Tyr Glu Arg Tyr Ala Met Leu Asp Ile
    210                 215                 220

Glu Lys Thr Gly Ala Lys Ile Gly Lys Trp Ile Val Gln Met Val Asn
225                 230                 235                 240

Glu Leu Asp Met Pro Phe Asp Thr Ile His Leu Ile Gly Gln Asn Val
                245                 250                 255

Gly Ala His Val Ala Gly Ala Ala Gln Glu Phe Thr Arg Leu Thr
            260                 265                 270

Gly His Lys Leu Arg Arg Val Thr Gly Leu Asp Pro Ser Lys Ile Val
        275                 280                 285

Ala Lys Ser Lys Asn Thr Leu Thr Gly Leu Ala Arg Gly Asp Ala Glu
    290                 295                 300

Phe Val Asp Ala Ile His Thr Ser Val Tyr Gly Met Gly Thr Pro Ile
305                 310                 315                 320

Arg Ser Gly Asp Val Asp Phe Tyr Pro Asn Gly Pro Ala Ala Gly Val
                325                 330                 335

Pro Gly Ala Ser Asn Val Val Glu Ala Ala Met Arg Ala Thr Arg Tyr
            340                 345                 350

Phe Ala Glu Ser Val Arg Pro Gly Asn Glu Arg Ser Phe Pro Ala Val
        355                 360                 365

Pro Ala Asn Ser Leu Gln Gln Tyr Lys Gln Asn Asp Gly Phe Gly Lys
    370                 375                 380

Arg Ala Tyr Met Gly Ile Asp Thr Ala His Asp Leu Glu Gly Asp Tyr
385                 390                 395                 400

Ile Leu Gln Val Asn Pro Lys Ser Pro Phe Gly Arg Asn Ala Pro Ala
                405                 410                 415

Gln Lys Gln Ser Ser Tyr His Gly Val His Gln Ala Trp Asn Thr Asn
            420                 425                 430

Gln Asp Ser Lys Asp Tyr Gln
        435
```

<210> SEQ ID NO 2
<211> LENGTH: 122
<212> TYPE: PRT
<213> ORGANISM: Drosophila melanogaster

```
<400> SEQUENCE: 2

His Leu Ser Gln Ile His His Asn Val Glu Pro Asn Tyr Val Pro Ser
1               5                   10                  15

Gly Ile Gln Val Tyr Val Pro Lys Pro Asn Gly Asp Lys Thr Val Ala
            20                  25                  30

Pro Leu Asn Glu Met Ile Gln Arg Leu Lys Gln Lys Gln Asn Phe Gly
        35                  40                  45

Glu Asp Glu Val Thr Ile Ile Val Thr Gly Leu Pro Gln Thr Ser Glu
50                  55                  60

Thr Val Lys Lys Ala Thr Arg Lys Leu Val Gln Ala Tyr Met Gln Arg
65                  70                  75                  80

Tyr Asn Leu Gln Gln Gln Arg Gln His Gly Lys Asn Gly Asn Gln Asp
                85                  90                  95

Tyr Gln Asp Gln Ser Asn Glu Gln Arg Lys Asn Gln Arg Thr Ser Ser
            100                 105                 110

Glu Glu Asp Tyr Ser Glu Glu Val Lys Asn
        115                 120

<210> SEQ ID NO 3
<211> LENGTH: 41
<212> TYPE: PRT
<213> ORGANISM: Drosophila melanogaster

<400> SEQUENCE: 3

Asn Leu Gln Gln Gln Arg Gln His Gly Lys Asn Gly Asn Gln Asp Tyr
1               5                   10                  15

Gln Asp Gln Ser Asn Glu Gln Arg Lys Asn Gln Arg Thr Ser Ser Glu
            20                  25                  30

Glu Asp Tyr Ser Glu Glu Val Lys Asn
        35                  40

<210> SEQ ID NO 4
<211> LENGTH: 8
<212> TYPE: PRT
<213> ORGANISM: Aedes aegypti

<400> SEQUENCE: 4

Gln Val Thr Lys Thr Gln Asn Phe
1               5

<210> SEQ ID NO 5
<211> LENGTH: 2148
<212> TYPE: PRT
<213> ORGANISM: Aedes aegypti

<400> SEQUENCE: 5

Met Leu Ala Lys Leu Leu Leu Ala Leu Ala Gly Leu Thr Ala Ala
1               5                   10                  15

Tyr Gln Tyr Glu Asn Ser Phe Lys Gly Tyr Asn Pro Gly Tyr Lys Gly
            20                  25                  30

Tyr Asp Ala Gly Tyr Lys Gly Tyr Gly Tyr Asp Ala Gly Tyr Lys Gly
        35                  40                  45

Tyr Gly Tyr Asp Ala Gly Tyr Lys Tyr Asn Asn Gln Gly Tyr Ser Tyr
50                  55                  60

Lys Asn Gly Phe Glu Tyr Gly Tyr Gln Asn Ala Tyr Gln Ala Ala Phe
65                  70                  75                  80

Tyr Lys His Arg Pro Asn Val Thr Glu Phe Glu Phe Ser Ser Trp Met
                85                  90                  95
```

```
Pro Asn Tyr Glu Tyr Val Tyr Asn Val Thr Ser Lys Thr Met Thr Ala
                100             105                 110

Leu Ala Glu Leu Asp Asp Gln Trp Thr Gly Val Phe Thr Arg Ala Tyr
        115                 120                 125

Leu Val Ile Arg Pro Lys Ser Arg Asp Tyr Val Ala Tyr Val Lys
    130                 135                 140

Gln Pro Glu Tyr Ala Val Phe Asn Glu Arg Leu Pro His Gly Tyr Ala
145                 150                 155                 160

Thr Lys Phe Tyr His Asp Met Phe Lys Phe Gln Pro Met Pro Met Ser
                165                 170                 175

Ser Lys Pro Phe Gly Ile Arg Tyr His Lys Gly Ala Ile Lys Gly Leu
            180                 185                 190

Tyr Val Glu Lys Thr Ile Pro Asn Asn Glu Val Asn Ile Leu Lys Ala
                195                 200                 205

Trp Ile Ser Gln Leu Gln Val Asp Thr Arg Gly Ala Asn Leu Met His
    210                 215                 220

Ser Ser Lys Pro Ile His Pro Ser Lys Asn Glu Trp Asn Gly His Tyr
225                 230                 235                 240

Lys Val Met Glu Pro Leu Val Thr Gly Glu Cys Glu Thr His Tyr Asp
                245                 250                 255

Val Asn Leu Ile Pro Ala Tyr Met Ile Gln Ala His Lys Gln Trp Val
            260                 265                 270

Pro Gln Gly Gln Leu Arg Gly Glu Asp Gln Phe Ile Gln Val Thr
                275                 280                 285

Lys Thr Gln Asn Phe Asp Arg Cys Asp Gln Arg Met Gly Tyr His Phe
            290                 295                 300

Gly Phe Thr Gly Tyr Ser Asp Phe Arg Pro Asn Thr Asn Gln Met Gly
305                 310                 315                 320

Asn Val Ala Ser Lys Ser Leu Val Ser Tyr Met Tyr Leu Thr Gly Asn
                325                 330                 335

Trp Tyr Asn Phe Thr Ile Gln Ser Ser Met Ile Asn Lys Val Ala
                340                 345                 350

Ile Ala Pro Ser Leu Val Asn Lys Glu Pro Ala Leu Val Tyr Ala Gln
            355                 360                 365

Val Asn Met Thr Leu Asn Asp Val His Pro Tyr Asp Lys Val Pro Met
370                 375                 380

Gly Pro Ala Glu Asp Leu Lys Val Phe Val Asp Leu Val Tyr Ser Tyr
385                 390                 395                 400

Asn Met Pro Ser Asp Lys Lys Asn Tyr Val Arg Pro Gly Asn Glu Thr
                405                 410                 415

Ser Ser Ser Ser Ser Ser Ser Ser Ser Ser Ser Ser Ser Ser Ser Glu
            420                 425                 430

Ser Ser Ser Ser Ser Ser Glu Ser Val Glu Asn Pro Lys Ile Ser Pro
            435                 440                 445

Val Glu Gln Tyr Lys Pro Leu Leu Asp Lys Val Glu Lys Arg Gly Asn
                450                 455                 460

Arg Tyr Arg Arg Asp Leu Asn Ala Ile Lys Glu Lys Lys Tyr Tyr Glu
465                 470                 475                 480

Ala Tyr Lys Met Asp Gln Tyr Arg Leu His Arg Leu Asn Asp Thr Ser
                485                 490                 495

Ser Asp Ser Ser Ser Asp Ser Ser Ser Ser Ser Ser Ser Glu Ser
            500                 505                 510
```

-continued

```
Lys Glu His Arg Asn Gly Thr Ser Ser Tyr Ser Ser Ser Ser Ser
            515                 520                 525
Ser Ser Ser Ser Ser Ser Glu Ser Ser Tyr Ser Ser Ser
        530                 535                 540
Ser Ser Ser Ser Glu Ser Tyr Ser Ile Ser Ser Glu Glu Tyr Tyr Tyr
545                 550                 555                 560
Gln Pro Thr Pro Ala Asn Phe Ser Tyr Ala Pro Glu Ala Pro Phe Leu
                565                 570                 575
Pro Phe Phe Thr Gly Tyr Lys Gly Tyr Asn Ile Phe Tyr Ala Arg Asn
                580                 585                 590
Val Asp Ala Ile Arg Ser Val Gly Lys Leu Val Glu Glu Ile Ala Ser
            595                 600                 605
Asp Leu Glu Asn Pro Ser Asn Leu Pro Lys Ala Asn Thr Met Ser Lys
        610                 615                 620
Phe Asn Ile Leu Thr Arg Ala Ile Arg Ala Met Gly Tyr Glu Asp Ile
625                 630                 635                 640
Tyr Glu Leu Ala Gln Lys Tyr Phe Val Ser Gln Lys Glu Arg Gln Val
                645                 650                 655
Ala Gln Phe Ser Asp Lys Lys Phe Ser Lys Arg Val Asp Ala Trp Val
                660                 665                 670
Thr Leu Arg Asp Ala Val Ala Glu Ala Gly Thr Pro Ser Ala Phe Lys
            675                 680                 685
Leu Ile Phe Asp Phe Ile Lys Glu Lys Lys Leu Arg Gly Tyr Glu Ala
        690                 695                 700
Ala Thr Val Ile Ala Ser Leu Ala Gln Ser Ile Arg Tyr Pro Thr Glu
705                 710                 715                 720
His Leu Leu His Glu Phe Phe Leu Val Thr Ser Asp Val Val Leu
                725                 730                 735
His Gln Glu Tyr Leu Asn Ala Thr Ala Leu Phe Ala Tyr Ser Asn Phe
                740                 745                 750
Val Asn Gln Ala His Val Ser Asn Arg Ser Ala Tyr Asn Tyr Tyr Pro
            755                 760                 765
Val Phe Ser Phe Gly Arg Leu Ala Asp Ala Asp Tyr Lys Ile Ile Glu
        770                 775                 780
His Lys Ile Val Pro Trp Phe Ala His Gln Leu Arg Glu Ala Val Asn
785                 790                 795                 800
Glu Gly Asp Ser Val Lys Ile Gln Val Tyr Ile Arg Ser Leu Gly Asn
                805                 810                 815
Leu Gly His Pro Gln Ile Leu Ser Val Phe Glu Pro Tyr Leu Glu Gly
                820                 825                 830
Thr Ile Gln Ile Thr Asp Phe Gln Arg Leu Ala Ile Met Val Ala Leu
            835                 840                 845
Asp Asn Leu Val Ile Tyr Tyr Pro Ser Leu Ala Arg Ser Val Leu Tyr
        850                 855                 860
Arg Ala Tyr Gln Asn Thr Ala Asp Val His Glu Val Arg Cys Ala Ala
865                 870                 875                 880
Val His Leu Leu Met Arg Thr Asp Pro Pro Ala Asp Met Leu Gln Arg
                885                 890                 895
Met Ala Glu Phe Thr His His Asp Pro Arg Leu Tyr Val Arg Ala Ala
                900                 905                 910
Val Lys Ser Ala Ile Glu Thr Ala Ala Leu Ala Asp Asp Tyr Asp Glu
            915                 920                 925
Asp Ser Lys Leu Ala Leu Asn Ala Lys Ala Ala Ile Asn Phe Leu Asn
```

```
            930             935             940
Pro Glu Asp Val Ser Ile Gln Tyr Ser Phe Asn His Ile Arg Asp Tyr
945                 950             955             960
Ala Leu Glu Asn Leu Glu Leu Ser Tyr Arg Leu His Tyr Gly Glu Ile
                965             970             975
Ala Ser Asn Asp His Arg Tyr Pro Ser Gly Leu Phe His Leu Arg
            980             985             990
Gln Asn Phe Gly Gly Phe Lys Lys Tyr Thr Ser Phe Tyr Tyr Leu Val
        995             1000            1005
Ser Ser Met Glu Ala Phe Phe Asp Ile Phe Lys Gln Tyr Asn
        1010            1015            1020
Thr Lys Tyr Phe Ala Asp Tyr Tyr Lys Ser Ala Asp Tyr Ser Thr
        1025            1030            1035
Asn Tyr Tyr Asn Phe Asp Lys Tyr Ser Lys Tyr Tyr Lys Gln Tyr
        1040            1045            1050
Tyr Tyr Ser Lys Asp Ser Glu Tyr Tyr Gln Lys Phe Tyr Gly Gln
        1055            1060            1065
Lys Lys Asp Tyr Tyr Asn Asp Lys Glu Pro Phe Lys Phe Thr Ala
        1070            1075            1080
Pro Arg Ile Ala Lys Leu Leu Asn Ile Asp Ala Glu Glu Ala Glu
        1085            1090            1095
Gln Leu Glu Gly Gln Leu Leu Phe Lys Leu Phe Asn Gly Tyr Phe
        1100            1105            1110
Phe Thr Ala Phe Asp Asn Gln Thr Ile Glu Asn Leu Pro His Lys
        1115            1120            1125
Met Arg His Leu Phe Glu Asn Leu Glu Asp Gly Tyr Ala Phe Asp
        1130            1135            1140
Val Thr Lys Phe Tyr Gln Gln Gln Asp Val Val Leu Ala Trp Pro
        1145            1150            1155
Leu Ala Thr Gly Phe Pro Phe Ile Tyr Thr Leu Lys Ala Pro Thr
        1160            1165            1170
Val Phe Lys Phe Glu Val Asp Ala Ser Ala Lys Thr His Pro Gln
        1175            1180            1185
Val Tyr Lys Met Pro Ala Gly His Pro Glu Thr Glu Asn Asp Asp
        1190            1195            1200
Phe Phe Tyr Met Pro Gln Ser Ile Asn Gly Ser Val Asp Val Asn
        1205            1210            1215
Leu Leu Tyr His Arg Met Val Asp Ala Lys Val Gly Phe Val Thr
        1220            1225            1230
Pro Phe Asp His Gln Arg Tyr Ile Ala Gly Tyr Gln Lys Lys Leu
        1235            1240            1245
His Gly Tyr Leu Pro Phe Asn Val Glu Leu Gly Leu Asp Phe Val
        1250            1255            1260
Lys Asp Glu Tyr Glu Phe Glu Phe Lys Phe Leu Glu Pro Lys Asp
        1265            1270            1275
Asp His Leu Leu Phe His Met Ser Ser Trp Pro Tyr Thr Gly Tyr
        1280            1285            1290
Lys Asp Ile Thr Asp Met Arg Pro Ile Ala Glu Asn Pro Asn Ala
        1295            1300            1305
Lys Ile Val His Asp Asp Asn Gln Ser Thr Lys Thr Met Glu His
        1310            1315            1320
Thr Phe Gly Gln Asp Met Thr Gly Val Ala Leu Arg Phe His Ala
        1325            1330            1335
```

```
Lys Tyr Asp Phe Asp Leu Ile Asn Phe Gln Gln Phe Trp Ser Leu
    1340            1345                1350

Ile Gln Lys Asn Asp Phe Val Ser Ala Val Asn Tyr Pro Phe Ala
    1355            1360                1365

Tyr Gln Pro Tyr Glu Tyr His Gln Phe Asn Leu Phe Tyr Asp Ser
    1370            1375                1380

Gln Arg Thr His Ala Lys Ser Phe Lys Phe Phe Ala Tyr Gln Lys
    1385            1390                1395

Phe Gly Ala Pro Ser Phe Glu Glu Thr Gly Pro Lys His Pro Ala
    1400            1405                1410

Asn Arg His Ser Tyr Ser Gly Asn Tyr Tyr Glu Ser Asn Tyr Ala
    1415            1420                1425

Gln Pro Phe Val Tyr Ser Pro Gly Ser Gln Arg Arg Tyr Glu Gln
    1430            1435                1440

Phe Phe Arg Asn Ala Ala Ser Gly Ile Arg Asn Ser Phe Val Arg
    1445            1450                1455

Tyr Tyr Asp Phe Gly Phe Glu Phe Tyr Ala Pro Gln Tyr Lys Ser
    1460            1465                1470

Glu Phe Thr Phe Thr Thr Ala Phe Ala Asp Ser Pro Val Asp Lys
    1475            1480                1485

Thr Ser Arg Gln Leu Tyr Tyr Phe Tyr Ala Ser Pro Met Phe Pro
    1490            1495                1500

Ser Gln Ser Tyr Phe Lys Asp Ile Pro Phe Ser Gly Lys Gln Phe
    1505            1510                1515

Gln Phe Cys Ala Thr Ala Thr Ser Glu Phe Pro Arg Val Pro Tyr
    1520            1525                1530

Leu Lys Phe Ser Asp Phe Asp Lys Tyr Tyr Gly Asp Ala Ser Gln
    1535            1540                1545

Tyr Phe Asp Phe Leu Tyr Gly Glu Ser Cys Gln Gly Gly Ala His
    1550            1555                1560

Ile Ala Val Lys Gly Lys Gln Lys Gln Thr Gly Lys Cys Arg Glu
    1565            1570                1575

Tyr Leu Arg Phe Ser Asp Val Ala Lys Ala Cys Lys Glu Gln Met
    1580            1585                1590

Ala Asn Gly Tyr Tyr Gln Phe Glu Glu Cys Gln Gln Ala Ile Asp
    1595            1600                1605

Gln Ala Tyr Tyr Tyr Asp Phe Tyr Asp Tyr Ala Ile Glu Tyr Lys
    1610            1615                1620

Asp Val Gly Ser Val Ala Lys Asn Leu Thr Asn Lys Phe Tyr Asn
    1625            1630                1635

Tyr Phe Gln Tyr Ala Phe Tyr Pro Tyr Phe Glu Ser Asn Phe Phe
    1640            1645                1650

Tyr His Gly Lys Ser Asn Tyr Ile Lys Ala Glu Phe Glu Phe Ala
    1655            1660                1665

Pro Tyr Gly Asp Tyr Tyr Asn Ala Ser Phe Phe Gly Pro Ser Tyr
    1670            1675                1680

Ala Phe Gln Val Gln Asn Tyr Pro Val Phe Asn Asp Tyr Ser Thr
    1685            1690                1695

Tyr Phe Pro Tyr Phe Phe Lys Tyr Thr Phe Phe Pro Arg Tyr Gln
    1700            1705                1710

Pro Tyr Tyr Met His Arg Leu Pro Ser His Lys Pro Arg Asn Arg
    1715            1720                1725
```

```
Pro Tyr Tyr Glu Leu Ser Asn Tyr Glu Gln Phe Ala Ile Phe Asp
    1730                1735                1740

Arg Lys Pro Gln Tyr Pro Ser Cys Ser Phe Ser Asn Asp Asn Phe
    1745                1750                1755

Tyr Thr Phe Asp Asn Lys Lys Tyr Phe Tyr Asp Met Gly Glu Cys
    1760                1765                1770

Trp His Ala Val Met Tyr Thr Val Lys Pro Asp Tyr Asp Phe Tyr
    1775                1780                1785

Ala Gln Gln Ser His Phe Tyr Asn Ser Asp Phe Glu Tyr Lys Tyr
    1790                1795                1800

Lys Asn Gly Phe Glu Glu Tyr Glu Gln Phe Ala Ala Leu Ala Arg
    1805                1810                1815

Arg Gly Ser Asp Asn Gln Leu Tyr Phe Lys Phe Leu Phe Gly Asp
    1820                1825                1830

Asn Tyr Ile Glu Val Phe Pro Asn Asn Gly Gly Val Pro Phe Val
    1835                1840                1845

Lys Tyr Asn Gly Arg Pro Tyr Asp Ile Ser Lys Ser Asn Ile Ala
    1850                1855                1860

His Phe Glu Tyr Lys Glu Gly Tyr Pro Ser Phe Pro Phe Phe Tyr
    1865                1870                1875

Ala Phe Ala Tyr Pro Asn Lys Asp Leu Glu Val Ser Phe Phe Gly
    1880                1885                1890

Gly Lys Leu Lys Phe Ala Thr Asp Gly Tyr Arg Ala Arg Phe Phe
    1895                1900                1905

Ser Asp Tyr Ser Phe Tyr Asn Asn Phe Val Gly Leu Cys Gly Thr
    1910                1915                1920

Asn Asn Gly Glu Tyr Phe Asp Glu Phe Val Thr Ala Asp Gln Cys
    1925                1930                1935

Tyr Met Arg Lys Pro Glu Phe Phe Ala Ala Ser Tyr Ala Ile Thr
    1940                1945                1950

Gly Gln Asn Cys Thr Gly Pro Ala Lys Ala Phe Asn Tyr Ala Tyr
    1955                1960                1965

Gln Gln Lys Ala Lys Gln Glu Cys Val Lys Arg Glu Val Tyr Tyr
    1970                1975                1980

Gly Asp Ile Ile Tyr Asn Gln Glu Tyr Tyr His Pro Arg Tyr Arg
    1985                1990                1995

Tyr Tyr Asn His Asn Val Glu Glu Ser Ser Ser Ser Ser Ser Ser
    2000                2005                2010

Ser Ser Ser Asp Ser Ser Ser Ser Ser Ser Ser Glu Phe Ser
    2015                2020                2025

Ser Leu Gly Arg Ser Gly Ser Ser Ser Ser Ser Ser Ser Ser Glu
    2030                2035                2040

Glu Gln Lys Glu Phe His Pro His Lys Gln Glu His Ser Met Lys
    2045                2050                2055

Glu Cys Pro Val Gln His Gln His Gln Phe Phe Glu Gln Gly Asp
    2060                2065                2070

Arg Ile Cys Phe Ser Leu Arg Pro Leu Pro Val Cys His Ser Lys
    2075                2080                2085

Cys Ala Ala Thr Glu Lys Ile Ser Lys Tyr Phe Asp Val His Cys
    2090                2095                2100

Phe Glu Lys Asp Ser Thr Gln Ala Lys Lys Tyr Lys Ser Glu Ile
    2105                2110                2115

Gly Arg Gly Tyr Thr Pro Asp Phe Lys Ser Phe Ala Pro His Lys
```

```
                    2120                2125                2130
         Thr Tyr Lys Phe Asn Tyr Pro Lys Ser Cys Val Tyr Lys Ala Tyr
                2135                2140                2145

<210> SEQ ID NO 6
<211> LENGTH: 8
<212> TYPE: PRT
<213> ORGANISM: Ichthyomyzon unicuspis

<400> SEQUENCE: 6

Ala Val Val Lys Thr Lys Asp Leu
1               5

<210> SEQ ID NO 7
<211> LENGTH: 8
<212> TYPE: PRT
<213> ORGANISM: Caenorhabditis elegans

<400> SEQUENCE: 7

Ile Ile Thr Lys Ser Ile Asn Phe
1               5

<210> SEQ ID NO 8
<211> LENGTH: 8
<212> TYPE: PRT
<213> ORGANISM: Graptopsaltria nigrofuscata

<400> SEQUENCE: 8

Arg Val Val Lys Thr Ile Asn Tyr
1               5

<210> SEQ ID NO 9
<211> LENGTH: 8
<212> TYPE: PRT
<213> ORGANISM: Riptortus clavatus

<400> SEQUENCE: 9

Glu Val Val Lys Thr Arg Asn Phe
1               5

<210> SEQ ID NO 10
<211> LENGTH: 8
<212> TYPE: PRT
<213> ORGANISM: Athalia rosae

<400> SEQUENCE: 10

Asp Ile Val Lys Thr Ser Asn Phe
1               5

<210> SEQ ID NO 11
<211> LENGTH: 8
<212> TYPE: PRT
<213> ORGANISM: Pimpla nipponica

<400> SEQUENCE: 11

Asp Ile Val Lys Thr Lys Asn Tyr
1               5

<210> SEQ ID NO 12
<211> LENGTH: 8
<212> TYPE: PRT
<213> ORGANISM: Blattella germanica

<400> SEQUENCE: 12
```

Thr Ile Met Lys Thr His Gln Phe
1               5

<210> SEQ ID NO 13
<211> LENGTH: 8
<212> TYPE: PRT
<213> ORGANISM: Xenopus laevis

<400> SEQUENCE: 13

Arg Ile Ile Lys Ser Thr Asp Phe
1               5

<210> SEQ ID NO 14
<211> LENGTH: 8
<212> TYPE: PRT
<213> ORGANISM: Anthonomus grandis

<400> SEQUENCE: 14

Glu Val Ile Lys Ser Lys Asn Tyr
1               5

<210> SEQ ID NO 15
<211> LENGTH: 8
<212> TYPE: PRT
<213> ORGANISM: Antheraea yamamai

<400> SEQUENCE: 15

Glu Ile Thr Lys Ser Lys Asn Tyr
1               5

<210> SEQ ID NO 16
<211> LENGTH: 8
<212> TYPE: PRT
<213> ORGANISM: Bombyx mori

<400> SEQUENCE: 16

Glu Val Thr Lys Ser Thr Asn Tyr
1               5

<210> SEQ ID NO 17
<211> LENGTH: 8
<212> TYPE: PRT
<213> ORGANISM: Acipenser transmontanus

<400> SEQUENCE: 17

Ile Val Thr Lys Ser Lys Asp Leu
1               5

<210> SEQ ID NO 18
<211> LENGTH: 8
<212> TYPE: PRT
<213> ORGANISM: Danio rerio

<400> SEQUENCE: 18

Ile Val Thr Lys Ser Lys Asp Leu
1               5

<210> SEQ ID NO 19
<211> LENGTH: 8
<212> TYPE: PRT
<213> ORGANISM: Cyprinus carpio

<400> SEQUENCE: 19

Thr Val Thr Lys Ser Lys Asp Leu
1               5

<210> SEQ ID NO 20
<211> LENGTH: 8
<212> TYPE: PRT
<213> ORGANISM: Samia cynthia

<400> SEQUENCE: 20

Glu Val Thr Lys Ser Lys Asn Leu
1               5

<210> SEQ ID NO 21
<211> LENGTH: 8
<212> TYPE: PRT
<213> ORGANISM: Oncorhynchus mykiss

<400> SEQUENCE: 21

His Leu Thr Lys Ser Lys Asp Leu
1               5

<210> SEQ ID NO 22
<211> LENGTH: 8
<212> TYPE: PRT
<213> ORGANISM: Oreochromis aureus

<400> SEQUENCE: 22

His Leu Thr Lys Thr Lys Asp Leu
1               5

<210> SEQ ID NO 23
<211> LENGTH: 8
<212> TYPE: PRT
<213> ORGANISM: Fundulus heteroclitus

<400> SEQUENCE: 23

Leu Leu Thr Lys Thr Arg Asp Leu
1               5

<210> SEQ ID NO 24
<211> LENGTH: 8
<212> TYPE: PRT
<213> ORGANISM: Oryzias latipes

<400> SEQUENCE: 24

Leu Leu Thr Lys Thr Arg Asp Met
1               5

<210> SEQ ID NO 25
<211> LENGTH: 8
<212> TYPE: PRT
<213> ORGANISM: Marsupenaeus japonicus

<400> SEQUENCE: 25

Ile Val Val Lys Glu Lys Asn His
1               5

<210> SEQ ID NO 26
<211> LENGTH: 8
<212> TYPE: PRT
<213> ORGANISM: Bemisia tabaci

<400> SEQUENCE: 26

Asp Ile Val Lys Thr Thr Asn Tyr
1               5

```
<210> SEQ ID NO 27
<211> LENGTH: 8
<212> TYPE: PRT
<213> ORGANISM: Bombus impatiens

<400> SEQUENCE: 27

Arg Lys Ser Lys Asn Phe Asp Lys
1               5

<210> SEQ ID NO 28
<211> LENGTH: 8
<212> TYPE: PRT
<213> ORGANISM: Ixodes scapularis

<400> SEQUENCE: 28

Asn Phe Thr Lys Thr Lys Asn Tyr
1               5

<210> SEQ ID NO 29
<211> LENGTH: 8
<212> TYPE: PRT
<213> ORGANISM: Danio rerio

<400> SEQUENCE: 29

Ile Val Thr Lys Ser Lys Asp Leu
1               5

<210> SEQ ID NO 30
<211> LENGTH: 13
<212> TYPE: PRT
<213> ORGANISM: Bemisia tabaci

<400> SEQUENCE: 30

Lys Pro Tyr Gly Val Tyr Lys Thr Met Glu Asp Ser Val
1               5                   10

<210> SEQ ID NO 31
<211> LENGTH: 17
<212> TYPE: PRT
<213> ORGANISM: Macrobrachium rosenbergii

<400> SEQUENCE: 31

Lys Pro Ala Tyr Gly Ser Tyr Lys Tyr Val Glu Ala His Gln Glu Ser
1               5                   10                  15

Val

<210> SEQ ID NO 32
<211> LENGTH: 13
<212> TYPE: PRT
<213> ORGANISM: Aedes aegypti

<400> SEQUENCE: 32

Glu Trp Asn Gly His Tyr Lys Val Met Glu Pro Leu Val
1               5                   10

<210> SEQ ID NO 33
<211> LENGTH: 13
<212> TYPE: PRT
<213> ORGANISM: Anopheles gambiae

<400> SEQUENCE: 33

Thr Leu Thr Gly Val Tyr Lys Thr Met Glu Pro Ser Val
1               5                   10
```

```
<210> SEQ ID NO 34
<211> LENGTH: 80
<212> TYPE: DNA
<213> ORGANISM: Artificial Sequence
<220> FEATURE:
<223> OTHER INFORMATION: Primer

<400> SEQUENCE: 34
aaaagcaccg actcggtgcc acttttttcaa gttgataacg gactagcctt attttaactt    60
gctatttcta gctctaaaac                                                 80

<210> SEQ ID NO 35
<211> LENGTH: 20
<212> TYPE: DNA
<213> ORGANISM: Artificial Sequence
<220> FEATURE:
<223> OTHER INFORMATION: Primer

<400> SEQUENCE: 35
ttcaagacca ggcctcaatc                                                 20

<210> SEQ ID NO 36
<211> LENGTH: 25
<212> TYPE: DNA
<213> ORGANISM: Artificial Sequence
<220> FEATURE:
<223> OTHER INFORMATION: Primer

<400> SEQUENCE: 36
tcactaaact cagccagtat cctat                                           25

<210> SEQ ID NO 37
<211> LENGTH: 10
<212> TYPE: DNA
<213> ORGANISM: Aedes aegypti

<400> SEQUENCE: 37
ggtgatcatt                                                            10

<210> SEQ ID NO 38
<211> LENGTH: 100
<212> TYPE: DNA
<213> ORGANISM: Aedes aegypti

<400> SEQUENCE: 38
tgtgggcggc aaggcggtga tcattggtga tgcggcacat gccatggttc ccttctacgg     60
gcagggaatg aatgccggat tcgaggattg tactgtgttg                          100

<210> SEQ ID NO 39
<211> LENGTH: 97
<212> TYPE: DNA
<213> ORGANISM: Aedes aegypti

<400> SEQUENCE: 39
tgtgggcggc aaggcggtga ttggtgatgc ggcacatgcc atggttccct tctacgggca     60
gggaatgaat gccggattcg aggattgtac tgtgttg                              97

<210> SEQ ID NO 40
<211> LENGTH: 95
<212> TYPE: DNA
<213> ORGANISM: Aedes aegypti

<400> SEQUENCE: 40
```

```
tgtgggcggc aaggcggtgg tgtgatgcgg cacatgccat ggttcccttc tacgggcagg    60
gaatgaatgc cggattcgag gattgtactg tgttg                              95

<210> SEQ ID NO 41
<211> LENGTH: 90
<212> TYPE: DNA
<213> ORGANISM: Aedes aegypti

<400> SEQUENCE: 41
tgtgggcggc aaggcggtga tgcggcacat gccatggttc ccttctacgg gcagggaatg    60
aatgccggat tcgaggattg tactgtgttg                                     90

<210> SEQ ID NO 42
<211> LENGTH: 98
<212> TYPE: DNA
<213> ORGANISM: Aedes aegypti

<400> SEQUENCE: 42
acccgccgtt ccgccactag taaccactac gccgtgtacg gtaccaaggg aagatgcccg    60
tcccttaatt acggcctaag ctcctaacat gacacaac                            98

<210> SEQ ID NO 43
<211> LENGTH: 90
<212> TYPE: DNA
<213> ORGANISM: Aedes aegypti

<400> SEQUENCE: 43
acccgccgtt ccgccactag taaccactac gccgtgtacg gtaccaaggg aagatgcccg    60
tcccttactt acggcctaac atgacacaac                                     90

<210> SEQ ID NO 44
<211> LENGTH: 88
<212> TYPE: DNA
<213> ORGANISM: Aedes aegypti

<400> SEQUENCE: 44
acccgccgtt ccgccactac gccgtgtacg gtaccaaggg aagatgcccg tcccttactt    60
acggcctaag ctcctaacat gacacaac                                       88

<210> SEQ ID NO 45
<211> LENGTH: 90
<212> TYPE: DNA
<213> ORGANISM: Aedes aegypti

<400> SEQUENCE: 45
acccgccgtt ccgccattag taaccactac gccgtgtacg gtaccaaggg aagatgcccg    60
tcccttactt acggcctaac atgacacaac                                     90

<210> SEQ ID NO 46
<211> LENGTH: 95
<212> TYPE: DNA
<213> ORGANISM: Aedes aegypti

<400> SEQUENCE: 46
acccgccgtt ccgccactaa ccactacgcc gtgtacggta ccaagggaag atgcccgtcc    60
cttacttacg gcctaagctc ctaacatgac acaac                               95

<210> SEQ ID NO 47
<211> LENGTH: 90
```

```
<212> TYPE: DNA
<213> ORGANISM: Aedes aegypti

<400> SEQUENCE: 47
acccgccgtt ccgccactag taaccactac gccgtgtacg ctaccaaggg aagatgcccg    60
tcccttactt acggcctaac atgacacaac                                     90

<210> SEQ ID NO 48
<211> LENGTH: 97
<212> TYPE: DNA
<213> ORGANISM: Aedes aegypti

<400> SEQUENCE: 48
acccgccgtt ccgccactag taaccactac gccgtgtacg gtaccaaggg aagatgcccg    60
tcccttaatt acggcctaag ctcctaacat gacacaa                             97

<210> SEQ ID NO 49
<211> LENGTH: 86
<212> TYPE: DNA
<213> ORGANISM: Aedes aegypti

<400> SEQUENCE: 49
acccgccgtt ccgccactag taaccactac gccgtgtacg gtaccaaggg aagatgcccg    60
tcccttactt acggcctaac atgaca                                         86

<210> SEQ ID NO 50
<211> LENGTH: 82
<212> TYPE: DNA
<213> ORGANISM: Aedes aegypti

<400> SEQUENCE: 50
acccgccgtt ccgccactac gccgtgtacg gtaccaaggg aaaatgcccg tcccttactt    60
acggcgccta acatgacaca ac                                             82

<210> SEQ ID NO 51
<211> LENGTH: 38
<212> TYPE: DNA
<213> ORGANISM: Bemisia tabaci

<400> SEQUENCE: 51
ccagtaactg ggatagcata cccaggtgag ctgttagc                            38

<210> SEQ ID NO 52
<211> LENGTH: 38
<212> TYPE: DNA
<213> ORGANISM: Bemisia tabaci

<400> SEQUENCE: 52
gctaacagct cacctgggta tgctatccca gttactgg                            38

<210> SEQ ID NO 53
<211> LENGTH: 12
<212> TYPE: PRT
<213> ORGANISM: Bemisia tabaci

<400> SEQUENCE: 53

Val Thr Gly Ile Ala Tyr Pro Gly Glu Leu Leu Ala
  1               5                  10

<210> SEQ ID NO 54
<211> LENGTH: 41
```

```
<212> TYPE: DNA
<213> ORGANISM: Bemisia tabaci

<400> SEQUENCE: 54
ccagtaactg ggatagcata tcacccaggt gagctgttag c                          41

<210> SEQ ID NO 55
<211> LENGTH: 38
<212> TYPE: DNA
<213> ORGANISM: Bemisia tabaci

<400> SEQUENCE: 55
ccagtaactg ggatagcagg cccaggtgag ctgttagc                              38

<210> SEQ ID NO 56
<211> LENGTH: 38
<212> TYPE: DNA
<213> ORGANISM: Bemisia tabaci

<400> SEQUENCE: 56
ccagtaactg ggatagcagg cccaggtgag ctgttagc                              38

<210> SEQ ID NO 57
<211> LENGTH: 31
<212> TYPE: DNA
<213> ORGANISM: Bemisia tabaci

<400> SEQUENCE: 57
gaactcctgg tagaataaag ggtatatcag g                                     31

<210> SEQ ID NO 58
<211> LENGTH: 31
<212> TYPE: DNA
<213> ORGANISM: Bemisia tabaci

<400> SEQUENCE: 58
cctgatatac cctttattct accaggagtt c                                     31

<210> SEQ ID NO 59
<211> LENGTH: 11
<212> TYPE: PRT
<213> ORGANISM: Bemisia tabaci

<400> SEQUENCE: 59

Gly Thr Pro Gly Arg Ile Lys Gly Ile Ser Gly
1               5                   10

<210> SEQ ID NO 60
<211> LENGTH: 52
<212> TYPE: DNA
<213> ORGANISM: Bemisia tabaci

<400> SEQUENCE: 60
gaactcctgg taataaaggg aataaagggg gtggaataaa gggtatatca gg              52

<210> SEQ ID NO 61
<211> LENGTH: 24
<212> TYPE: PRT
<213> ORGANISM: Macrobrachium rosenbergii

<400> SEQUENCE: 61

Asp Lys Asn Ile Ile Lys Pro Ala Tyr Gly Ser Tyr Lys Tyr Val Glu
1               5                   10                  15
```

Ala His Gln Glu Ser Val Leu Arg
            20

<210> SEQ ID NO 62
<211> LENGTH: 60
<212> TYPE: PRT
<213> ORGANISM: Bemisia tabaci

<400> SEQUENCE: 62

Lys Asn Val Ser Asp Trp Glu Leu Asn Ile Ile Lys Ala Val Val Ser
1               5                   10                  15

Gln Ile Gln Val Asp Thr Gln Gly Gln Asn Leu Lys Lys Ser Ser His
            20                  25                  30

Asn Gln Leu Pro Lys Glu Asn Lys Pro Tyr Gly Val Tyr Lys Thr Met
        35                  40                  45

Glu Asp Ser Val Thr Gly Glu Cys Glu Thr Leu Tyr
    50                  55                  60

<210> SEQ ID NO 63
<211> LENGTH: 60
<212> TYPE: PRT
<213> ORGANISM: Bemisia tabaci

<400> SEQUENCE: 63

Lys Asn Val Ser Asp Trp Glu Leu Asn Ile Ile Lys Ala Val Val Ser
1               5                   10                  15

Gln Ile Gln Val Asp Thr Gln Gly Gln Asn Leu Lys Lys Ser Ser His
            20                  25                  30

Asn Gln Leu Pro Lys Glu Asn Lys Pro Tyr Gly Val Tyr Lys Thr Met
        35                  40                  45

Glu Asp Ser Val Thr Gly Glu Cys Glu Thr Leu Tyr
    50                  55                  60

<210> SEQ ID NO 64
<211> LENGTH: 60
<212> TYPE: PRT
<213> ORGANISM: Aedes aegypti

<400> SEQUENCE: 64

Lys Thr Ile Pro Asn Asn Glu Val Asn Ile Leu Lys Ala Trp Ile Ser
1               5                   10                  15

Gln Leu Gln Val Asp Thr Arg Gly Ala Asn Leu Met His Ser Ser Lys
            20                  25                  30

Pro Ile His Pro Ser Lys Asn Glu Trp Asn Gly His Tyr Lys Val Met
        35                  40                  45

Glu Pro Leu Val Thr Gly Glu Cys Glu Thr His Tyr
    50                  55                  60

<210> SEQ ID NO 65
<211> LENGTH: 60
<212> TYPE: PRT
<213> ORGANISM: Anopheles gambiae

<400> SEQUENCE: 65

Lys Thr Val Pro Asn His Glu Val Asn Met Leu Lys Gly Trp Val Ser
1               5                   10                  15

Gln Leu Gln Leu Asp Thr Gln Gly Ala Tyr Val Ile Lys Ser Glu Phe
            20                  25                  30

Asn Gln Phe Pro Glu Asn Asn Thr Leu Thr Gly Val Tyr Lys Thr Met
        35                  40                  45

```
Glu Pro Ser Val Thr Gly Glu Cys Glu Thr Leu Tyr
 50                  55                  60
```

```
<210> SEQ ID NO 66
<211> LENGTH: 20
<212> TYPE: DNA
<213> ORGANISM: Artificial Sequence
<220> FEATURE:
<223> OTHER INFORMATION: Primer

<400> SEQUENCE: 66
atccactgtg cggcattctt                                                    20

<210> SEQ ID NO 67
<211> LENGTH: 20
<212> TYPE: DNA
<213> ORGANISM: Artificial Sequence
<220> FEATURE:
<223> OTHER INFORMATION: Primer

<400> SEQUENCE: 67
ttccattgac tgctcgctgg                                                    20

<210> SEQ ID NO 68
<211> LENGTH: 24
<212> TYPE: DNA
<213> ORGANISM: Artificial Sequence
<220> FEATURE:
<223> OTHER INFORMATION: Primer

<400> SEQUENCE: 68
tgctggaaag gtagaatttg aacg                                               24

<210> SEQ ID NO 69
<211> LENGTH: 22
<212> TYPE: DNA
<213> ORGANISM: Artificial Sequence
<220> FEATURE:
<223> OTHER INFORMATION: Primer

<400> SEQUENCE: 69
tggatgccca acaacattct tt                                                 22

<210> SEQ ID NO 70
<211> LENGTH: 62
<212> TYPE: DNA
<213> ORGANISM: Artificial Sequence
<220> FEATURE:
<223> OTHER INFORMATION: Guide sequence

<400> SEQUENCE: 70
gaaattaata cgactcacta tagtgaggac gcattggtct gtgttttaga gctagaaata       60
gc                                                                      62

<210> SEQ ID NO 71
<211> LENGTH: 62
<212> TYPE: DNA
<213> ORGANISM: Artificial Sequence
<220> FEATURE:
<223> OTHER INFORMATION: Guide sequence

<400> SEQUENCE: 71
gaaattaata cgactcacta tagttgatgc cggaccacgt gtgttttaga gctagaaata       60
gc                                                                      62
```

```
<210> SEQ ID NO 72
<211> LENGTH: 62
<212> TYPE: DNA
<213> ORGANISM: Artificial Sequence
<220> FEATURE:
<223> OTHER INFORMATION: Guide sequence

<400> SEQUENCE: 72
gaaattaata cgactcacta taggcatcaa cgtcttcgcc tcgttttaga gctagaaata        60
gc                                                                       62

<210> SEQ ID NO 73
<211> LENGTH: 62
<212> TYPE: DNA
<213> ORGANISM: Artificial Sequence
<220> FEATURE:
<223> OTHER INFORMATION: Guide sequence

<400> SEQUENCE: 73
gaaattaata cgactcacta tagtaactgg gatagcatac ccgttttaga gctagaaata        60
gc                                                                       62

<210> SEQ ID NO 74
<211> LENGTH: 62
<212> TYPE: DNA
<213> ORGANISM: Artificial Sequence
<220> FEATURE:
<223> OTHER INFORMATION: Guide sequence

<400> SEQUENCE: 74
gaaattaata cgactcacta tagatatacc ctttattcta ccgttttaga gctagaaata        60
gc                                                                       62

<210> SEQ ID NO 75
<211> LENGTH: 80
<212> TYPE: DNA
<213> ORGANISM: Artificial Sequence
<220> FEATURE:
<223> OTHER INFORMATION: Guide sequence

<400> SEQUENCE: 75
aaaagcaccg actcggtgcc acttttttcaa gttgataacg gactagcctt attttaactt      60
gctatttcta gctctaaaac                                                    80
```

TARGETING PEPTIDE TO DELIVER A COMPOUND TO OOCYTES

CROSS-REFERENCE TO RELATED APPLICATION

This application is a by-pass continuation of PCT/US18/57988, filed Oct. 29, 2018, which claims priority to U.S. provisional application Ser. No. 62/578,805, filed Oct. 30, 2017, the contents of which are incorporated herein by reference in their entirety.

GRANT REFERENCE

This invention was made with government support under Grant No. AI111175, awarded by the National Institute of Health and under Hatch Act Project No. PEN04445, awarded by the United States Department of Agriculture and NSF/BIO grant 1645331. The Government has certain rights in the invention.

SEQUENCE LISTING

The instant application contains a Sequence Listing which has been submitted in ASCII format via EFS-Web and is hereby incorporated by reference in its entirety. Said ASCII copy, created on May 14, 2020, is named P12402US01_SEQLISTING_05-14-20_ST25.txt, and is 39,263 bytes in size.

BACKGROUND

The use of specific ligands to deliver material into mammalian cells by receptor-mediated endocytosis has been explored for drug delivery since the 1980's (Wagner, Curiel and Cotten, 1994; Qian et al., 2002; Bareford and Swaan, 2007). For example, when the protein transferrin (Tf) was used as a ligand and chemically conjugated to molecular compound such as toxins (FitzGerald et al., 1983), liposomes (Hege et al., 1989; Matthay et al., 1989) proteins (Wagner, Curiel and Cotten, 1994) or DNA (Stavridis and Psallidopoulos, 1982), these molecules were internalized into the cell via the transferrin receptor (TfR) and released into the cell cytoplasm in vitro and in vivo (Widera, Norouziyan and Shen, 2003; Vácha, Martinez-Veracoechea and Frenkel, 2011; Chen et al., 2013). Delivery efficacy depends on successful release of compound from the endosomes and lysosomes (Stavridis and Psallidopoulos, 1982; Takahashi and Tavassoli, 1983; Hege et al., 1989; Matthay et al., 1989; Wagner, Curiel and Cotten, 1994; Widera, Norouziyan and Shen, 2003; Kiesgen et al., 2014), often by chemical membrane destabilizers such as ammonium chloride, amines, chloroquine or monensin (Wagner, Curiel and Cotten, 1994; Qian et al., 2002; Fuchs, Bachran and Flavell, 2013; Gilabert-Oriol et al., 2014).

Gene editing systems, such as CRISPR/Cas9 is a powerful tool for addressing research questions in diverse organisms. Current approaches rely upon delivering Cas9 ribonucleoprotein (RNP) complex to eggs/embryos by microinjection. However, embryonic microinjection is challenging, not possible in many species, and inefficient even in optimized taxa.

SUMMARY

The present methods are to targeting molecules to oocytes of animals and insects. In an embodiment a molecule of interest is targeted to the oocyte utilizing an oocyte targeting molecule. The oocyte targeting molecule in an embodiment is a yolk protein precursor. Such precursors may in further embodiments be vitellogenin, lipophorin, YP1, P2, P2C or a functional fragment or functional variant thereof. Gene editing may be accomplished using the process where, for example, a gene editing molecule of such processes as CRISPR/Cas, TALEN, Zinc Finger Nucleases or other molecules used in gene editing are targeted to the oocyte. Further embodiments provide for use of such processes to modify expression of a sequence within the animal.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 9A shows the G0 white (arrows) and wild type larvae. FIG. 9B shows mosaic pupae. FIG. 9C shows wild type and white pupae. FIG. 9D shows mosaic adult. FIG. 9E shows wild type and white adults.

Figure 1:
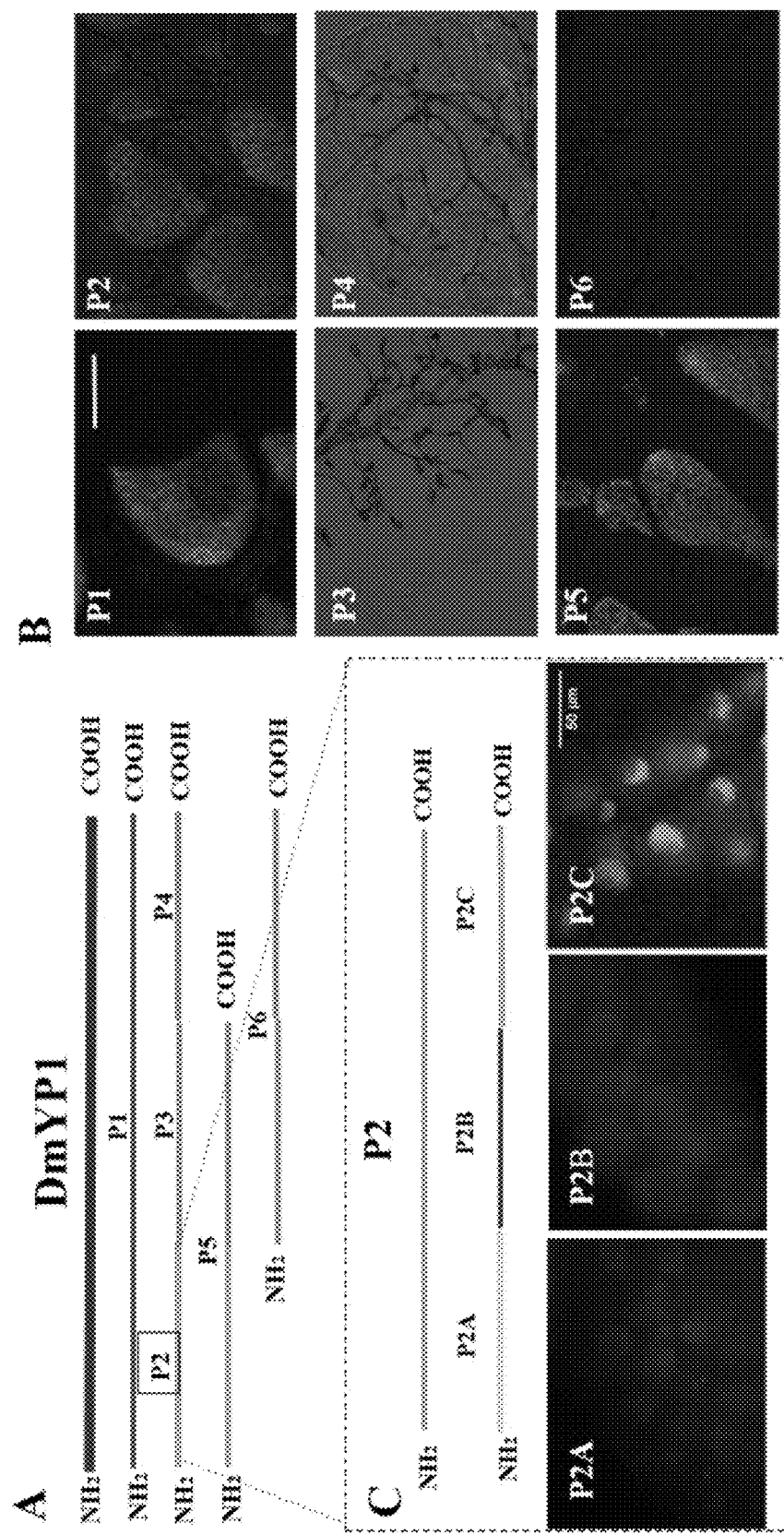
FIG. 1 shows the deletion mapping to identify the receptor binding region (RBR) of DmYP1. The schematic shows the deletion analysis strategy of DmYP1 (439 amino acids). Each portion (P1-P6) was expressed as an EGFP fusion protein. Visualization of EGFP by fluorescence microscopy in *Anopheles gambiae* oocytes following injection of DmYP1 fragment (P1-P6)-EGFP fusion proteins. P2 was further divided in three portions (P2A, P2B and P2C) and expressed as EGFP fusion proteins. Portion P2C (41 amino acids) contained the RBR.
Figure 2:
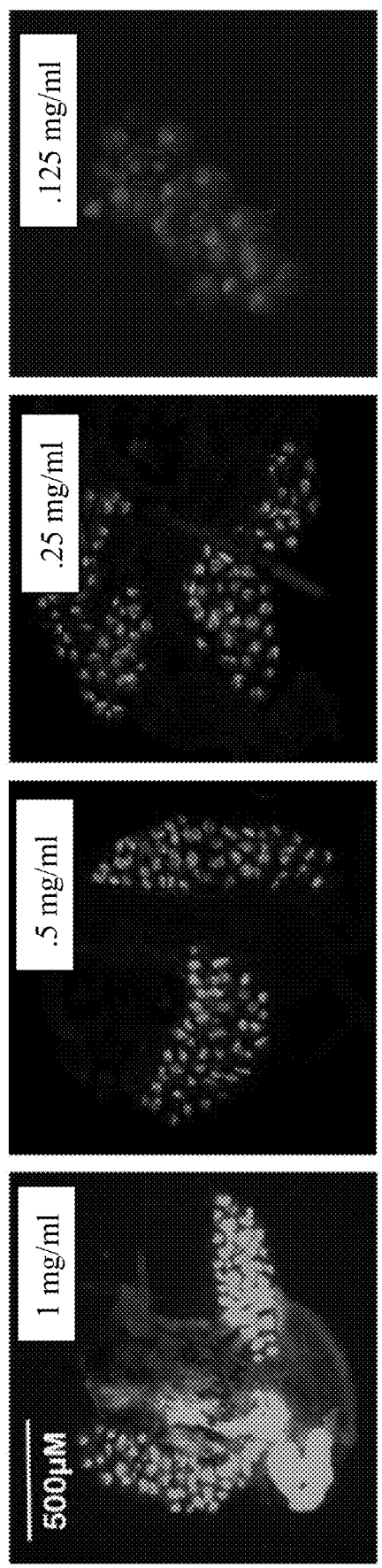
FIG. 2 shows P2C-mediated transduction of EGFP is dose-dependent. All mosquitoes were injected 12 h PBG and ovaries dissected 24 h PBF.

FIG. 18 depicts wild-type and mutant *B. tabaci*. Panels A, B, C, and D show wild-type from 2nd, 3rd, and 4th instar nymphs, and adult, respectively. Panels F, G, H, and I show matched-stage mutant individuals resulting from ReMOT Control editing of the *B. tabaci* white gene by BtKV targeting of Cas9 ribonucleoprotein complex. Black arrows point to eye(s) of wild-type and mutants. Panel E shows both mutant and wild-type in the same image. Black arrowhead points to mutant adult.

FIGS. 19A-C show mutant alleles and homology modeling of the [21 bp] insertion. FIG. 19A shows the mutant alleles (M1; 3 nt insertion and M2; 2 nt substitution, M3; 4 nt deletion) identified at exon 3 compared to the wild-type sequence (SEQ ID NOs: 51-56). 2nd and ♂ indicates the instar/life stage the mutation was identified in (2 adult males shared this mutation). FIG. 19B shows the 21 bp insertion (M) at exon 5 in a 1st nymphal instar (SEQ ID NOs: 57-60). FIG. 19C shows the predicted 3D structure of the wild-type *B. tabaci* white protein (left) corn-pared to the structure of the in-frame 21 bp insertion mutant (right). The insertion is predicted to cause a loop (arrow) across the channel pore, sterically hindering function of the transporter, leading to a null mutation.

FIG. 20 is a depiction of the crossing scheme to identify heritability. Injected females (G-1) can produce wild-type males and females (black), mutant males (red), and/or hemizygous females (red/black) in G0. The resulting mutant males were crossed with the female siblings to generate the G1. The G1 hemizygous females were backcrossed with G0 mutant males to generate G2 offspring which were scored as juveniles for white or wild-type eyes.

FIG. 21 shows the identification of the BtKV ligand. Microbrachiumrosenbergii 24 amino acid sequence identified in Roth et al. 2013, *B. tabaci* predicted vitellogenin-A1-like (XP_018912902.1), *B. tabaci* predicted vitellogenin (XP_018897090.1), *B. tabaci* predicted low quality vitellogenin (XP_018897089.1), *Aedes aegypti* vitellogenin (AAA99486.1), and *Anopheles gambiae* vitellogenin (AAF82131.1) were aligned using ClustalW in MEGA 7.0.26, then manually aligned the "KP" amino acids to match the "KP" of the vitellogenins of *B. tabaci* (SEQ ID NOs: 61-65). As the targeting ligand we chose the sequence from the *B. tabaci* "KP" to the conserved valine (V) (red arrows).

DETAILED DESCRIPTION

Methods are provided here to target a molecule of interest to the oocyte of an animal or insect. The methods utilized in an embodiment oocyte targeting molecule conjugated to a molecule of interest. Where that molecule of interest is a molecule utilized in gene editing, it may be targeted to the oocyte. Methods here provide for identification of such oocyte targeting peptides that can enter the oocyte through endocytosis. One such targeting molecule are yolk protein precursors (YPP). Embodiments provide the targeting molecule is a receptor binding region of a yolk protein precursor. In one embodiment the YPP may be vitellogenin, lipophorin, the YP1, 2, 3, protein or a fragment thereof such as the PC sequence or P2C sequence. Nucleic acid molecules encoding such peptides may be utilized in the process.

The methods here may use the targeting peptides to deliver a compound to an oocyte without resorting to embryo microinjection. The targeting peptide along with the molecule of interest may be injected into an organism in an embodiment and the targeting peptide delivers the molecule of interest to the oocyte.

With such methods one may use a targeting peptide to target transformed or transgenic cells expressing the targeting peptide receptor in tissues or organisms that may not naturally express the receptor. Where the molecule of interest is a gene editing component, gene editing of the animal may be accomplished in which a modification has been made to the gene of the animal, whether a deletion, insertion, mutation, replacement, duplication, translocation of sequences or the like. Examples of gene editing techniques and molecules utilized in such systems include, without limitation, the CRISPR/Cas process, the use of TALENs and Zinc Finger Nucleases, as discussed further below. Components of TALENs include transcription activator-like effectors (TALEs) proteins with a central domain for DNA binding, a nuclear localization signal and a domain activating target gene transcription. Certain of the TALE proteins recognize specific DNA, tandem repeats of 33 or 34 amino acids, where a repeat variable diresidue is responsible for recognition of a particular nucleotide. TALENs are able to recognize a single nucleotide.

CRISPR/Cas is one such gene editing system. CRISPR/Cas uses non-coding RNAs and Cas endonuclease proteins. The non-coding RNA and target site complementary interact. Short regions of unique RNA are separated by short palindromic repeats. CRISPR stands for Clustered Regular Interspaced Short Palindromic Repeats. The molecules used in such processes including crRNA, tracRNA which may be sgRNA, and Cas protein. Zinc Finger nucleases use an endonuclease with a zinc finger protein domain recognizing a nucleotide triplet. In the present methods the oocyte targeting molecule may be used to further direct one or more components of such editing systems. For example, the Cas molecule may be delivered to the animal with the oocyte targeting compound to enhance gene editing in the oocyte. Such methods are discussed further below.

Any molecule of interest may be delivered to the oocyte using the methods disclosed. Examples of other such molecules include one or more of the gene editing molecules discussed above, which may result in deletion, insertion, duplication, translocation or the like. Other molecules may be introduced such as molecules having a desired effect at the target site such as increasing, decreasing or otherwise modifying expression; labeling molecules such as a compound producing a visible response or providing resistance to a substance; molecules beneficial to the subject, cell or nucleic acid molecule or polypeptide, or that may be detrimental to the cell or nucleic acid molecule of peptide, such as when used in cancer therapies. Still further examples include use to target molecules for column purification, ELISA, or labeling. One skilled in the art can and will envision may uses for delivering a molecule to the oocyte.

Mosquitoes are excellent models for development of this technology because synchronous egg development can be induced by blood feeding, significant literature exists on vitellogenesis and receptor-mediated internalization of yolk proteins (Raikhel, 1984; Noah Koller, Dhadialla and Raikhel, 1989; Sun et al., 2000; Cheon et al., 2001; Tufail and Takeda, 2005), and multiple validated target genes and Cas9 single guide RNAs (sgRNAs) have already been tested (Basu et al., 2015) for *Ae. aegypti*, allowing us to directly compare peptide targeting efficacy to standard embryonic microinjection-based delivery.

Most female oviparous animals successfully deliver material to their developing ovaries through a conserved process of ovary and egg maturation called vitellogenesis. In mosquitoes and other arthropods, yolk protein precursors (YPPs) are synthesized in the fat body, secreted into the hemolymph, and are taken up into the ovaries by receptor-mediated endocytosis (RME). Developing eggs can increase in size up to 300-fold during this process (Koller, Dhadialla and Raikhel, 1989). During vitellogenesis, multiple receptors in the oocyte membrane are available and bind several YPP ligands that are internalized, accumulated in endosomal vesicles and sorted into yolk granules for nutrient storage for the developing embryo (Davail et al., 1998; Sappington and Raikhel, 1998).

Here disclosed are small targeting peptides that preferentially target to and bind sequences of oocytes, such as yolk protein precursors. Embodiments provide the peptides and nucleic acid sequences encoding same mediate transduction of a compound to cells. An example is a molecule which recognizes Yolk Protein 1 (YP1). The term "Yolk Protein Precursor" or "YPP" refers to any protein that is selectively taken up into oocytes during vitellogenesis, and includes, but is not limited to yolk proteins, vitellogenins, or lipophorins. The targeting moieties can be attached to molecules of interest, also referred to as effectors (e.g., detectable labels, drugs, antimicrobial peptides, polynucleotide or protein sequences etc. such as those referred to above) to form chimeric constructs for specifically/preferentially delivering the effector to and/or into the target oocyte.

In an embodiment the targeting peptide binds to a receptor found on at least oocytes. In another embodiment the targeting peptide is the binding site present in a YP1 protein. In a further aspect the targeting peptide is a subunit of YP1 that retains its ability to bind to the YP1 receptor on the oocyte.

In still a further aspect, the targeting peptide is the *Drosophila melanogaster* YP1 (DmYP) protein. See, for example the 439 amino acid sequence of GenBank Accession No. NP_511103.1 "Yolk protein 1, isoform A [*Drosophila melanogaster*]" (2018) and GenBank Accession No. NP_001285071 "Yolk protein 1, isoform B [*Drosophila melanogaster*]" (2018) (SEQ ID NO: 1). In yet another aspect the targeting peptide is a 120 amino acid subunit of DmYP that retains the binding affinity of DmYP to target receptors termed "P2". (SEQ ID NO: 2): HLSQIHHNVEPNYVPSGIQVYVPKPNGDKTVAPLNE-MIQRLKQKQNFGEDEVTIIVTGLPQTSE TV KKATRKLVQAYMQRYNLQQQRQHGKNG-NQDYQDQSNEQRKNQRTSSEEDYSEEVKN. In another aspect, a smaller subunit of DmYP is termed "P2C" and is defined by the 41 amino acid sequence NLQQQRQHGKNGNQDYQDQSNEQRKNQRTS-SEEDYSEEVKN (SEQ ID NO: 3). In yet another aspect, orthologs of this sequence from homologous genes of similar function from other organisms.

In one embodiment a nucleic acid is provided (a) encoding YP1 or a subunit of YP1 such as, but not limited to, P2 or P2C, that retains the receptor biding function or (b) having a nucleic acid sequence which is at least 70% homology, more preferably at least 80%, 81%, 82%, 83%, 84%, 85%, 86%, 87%, 88%, 89%, 90%, 91%, 92%, 93%, 94%, 95%. 96%, 97%, 98%, or 99% homology to YP1 or a subunit; or (c) which hybridizes to a nucleic acid sequence which encodes the same under at least moderately to highly stringent conditions. In certain embodiments the nucleic acid sequence includes one modification so that it does not encode the native protein.

In one aspect proteins or peptides which target receptors on at least the oocyte, as well as modified forms, subsequences or fragments thereof. In one embodiment includes a polypeptide comprising (a) having a nucleic acid sequence which is at least 70% homology, more preferably at least 80%, 81%, 82%, 83%, 84%, 85%, 86%, 8'7%, 88%, 89%, 90%, 91%, 92%, 93%, 94%, 95%. 96%, 97%, 98%, or 99% homology to YP1 or a subunit (b) a polypeptide encoded by a nucleic acid; and (c) a polypeptide comprising targeting activity and comprising at least 8 amino acids conserved of (a). In certain embodiments the protein includes at least one modification, substitution or amino acid change from the native protein.

Amino acid sequences which are functional fragments or variants or are substantially similar to the amino acid sequences described above, and which are capable of targeting binding to at least oocytes are within the scope of this invention.

In a further aspect, targeting sequences derived from other YPP genes that bind to yolk protein receptors in a similar manner to DmYP, P2, P2C and the like.

In a further aspect the nucleic acid sequence encoding the targeting peptide and a molecule of interest form a heterologous construct. In another embodiment, the above heterologous construct may part of an expression vector. The expression vector may then be transfected into the cells appropriate to activate the promoter, causing the expression of a fusion protein. The fusion protein may be YP1 or a subunit and the molecule of interest. In further aspects, the invention relates to a polynucleotide encoding a conjugate according to the invention, a vector comprising said polynucleotide and a host cell comprising said polynucleotide or said vector.

In another example the targeting molecule may be vitellogenin ligands that bind to oocyte receptors. The targeting molecule may encompass positions 286-293 of the *Aedes aegypti* vitellogenin gene QVTKTQNF (SEQ ID NO: 4), VgA1, GenBank accession number AAA99486.1 (SEQ ID NO: 5) or homologous region in the vitellogenin gene of other organisms. For example, the targeting molecule may be any of AVVKTKDL(lamprey, SEQ ID NO: 6), IITKSINF (nematode, SEQ ID NO: 7), RVVKTINY (cicada, SEQ ID NO: 8), EVVKTRNF (bean bug, SEQ ID NO: 9), DIVKTSNF (saw fly, SEQ ID NO: 10), DIVKTKNY (wasp, SEQ ID NO: 11), TIMKTHQF (cockroach, SEQ ID NO: 12), RIIKSTDF (frog, SEQ ID NO: 13), EVIKSKNY (weevil, SEQ ID NO: 14), EITKSKNY (oak silkmoth, SEQ ID NO: 15), EVTKSTNY (silkworm, SEQ ID NO: 16), IVTKSKDL (sturgeon, SEQ ID NO: 17), IVTKSKDL (zebrafish, SEQ ID NO: 18) TVTKSKDL (carp, SEQ ID NO: 19), EVTKSKNL (silkmoth, SEQ ID NO: 20), HLTKSKDL (trout, SEQ ID NO: 21), HLTKTKDL (tilapia, SEQ ID NO: 22), LLTKTRDL (killifish, SEQ ID NO: 23), LLTKTRDM (ricefish SEQ ID NO:24), IVVKEKNH (prawn, SEQ ID NO: 25), DIVKTTNY (*Bemisia tabaci*, SEQ ID NO: 26), RKSKNFDK (*Bombus impatiens*, SEQ ID NO: 27), NFTKTKNY (*Ixodes scapularis*, SEQ ID NO: 28), IVTKSKDL (*Danio rerio*, SEQ ID NO: 29), KPYGVYKTMEDSV (*B. tabaci*, SEQ ID NO:30), KPAYGSYKYVEAHQESV (*Macrobrachium rosenbergii*, SEQ ID NO:31), EWNGHYKVMEPLV (*Aedes aegypti*, SEQ ID NO:32), TLTGVYKTMEPSV (*Anopheles gambiae*, SEQ ID NO:33)

A further aspect may be the fusion protein where the targeting peptide and the molecule of interest are separated by a linker. A further embodiment may be YP1 or a subunit linked to one or more affinity ligands such as, but not limited to, an antibody.

Functional fragments and variants of such peptides are disclosed herein and are encompassed within the method described.

A functional fragment or variant of a nucleic acid molecule or amino acid is one which retains the property of targeting to the oocyte, such as binding to a receptor of the yolk protein precursor. As described herein, there are many methods to identify such variants or fragments.

One example is deletion analysis. In such methods smaller fragments may yet contain the properties of the sequence so identified and deletion analysis is one method of identifying essential regions Fragments can be obtained by site-directed mutagenesis, mutagenesis using the polymerase chain reaction and the like. (See, *Directed Mutagenesis: A Practical Approach IRL Press* (1991)).

Any molecule of interest may be delivered to the oocyte. Another aspect may be the targeting peptide linked to multiple molecules, such as but not limited to a compound to be delivered and one or more affinity ligands.

In other embodiments a targeting peptide can be conjugated with a therapeutic agent.

In other aspects the targeting peptide can be bound to a stationary base and be used to purify the targeting peptide targets.

In other aspects the compound attached to the targeting peptide may also be a virus, a bacteriophage, a bacterium, a liposome, a microparticle, a magnetic bead, a yeast cell, a mammalian cell or a cell. In particular embodiments, the complex is a virus or a bacteriophage. A virus includes, but is not limited to adenovirus, retrovirus, or adeno-associated virus (AAV). A virus may be a gene therapy vector containing a therapeutic nucleic acid or a gene therapy. In certain aspects the peptide is attached to a eukaryotic expression vector, preferably a gene therapy vector. Compositions comprising the isolated peptide will typically be comprised in a pharmaceutically acceptable composition.

In yet another aspect the targeting peptide is conjugated with a genomic editing system such as, but not limited to, CRISPR/Cas9 ribonucleic protein, TALEN system, or zinc finger nuclease system as discussed further herein. It is contemplated by this invention that organisms with germline changes are also encompassed.

In other aspects, the targeting peptides receptor can be transfected into and synthetically expressed in cells which normally do not express the receptor. The targeting peptide can then be used for specific delivery to the transfected cells.

Further, it has been shown here that it is possible for a molecule delivered by the oocyte targeting molecule and/or the resulting modification to the targeted molecule and/or the phenotype resulting can be stably incorporated into the animal or insect and is heritable by progeny.

In order to provide a clear and consistent understanding of the specification and the claims, including the scope given to such terms, the following definitions are provided. Units, prefixes, and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range and include each integer within the defined range. Amino acids may be referred to herein by either their commonly known three letter symbols or by the one-letter symbols recommended by the IUPAC-IUB Biochemical Nomenclature Commission.

Nucleotides, likewise, may be referred to by their commonly accepted single-letter codes. Unless otherwise provided for, software, electrical, and electronics terms as used herein are as defined in The New IEEE Standard Dictionary of Electrical and Electronics Terms (5th edition, 1993). The terms defined below are more fully defined by reference to the specification as a whole. The singular terms "a", "an", and "the" include plural referents unless context clearly indicates otherwise. Similarly, the word "or" is intended to include "and" unless the context clearly indicate otherwise. The word "or" means any one member of a particular list and also includes any combination of members of that list.

The term "molecule of interest" or "compound" is used to mean any substance that can be either affinity or covalently bound to a targeting peptide. Examples include, but are not limited to protein, macromolecule, therapeutic agent, peptide, nucleic acid, lipid, virus, cell, cell component, individually or in combination. For example, the CRISPR/Cas9 protein and the guide ribonucleic acid. One skilled in the art will understand that this is not an exhaustive list of possible compounds. Other examples are set forth herein.

A "ligand" is a molecule that forms a complex with another molecule. In protein-ligand binding the ligand may cause the receptor to signal, an agonist, or prevents the receptor to signa, an antagonist.

As used herein the term "targeting molecule," "targeting moiety," or "targeting ligand" refers to any molecule that provides an enhanced affinity for a selected target, e.g., a cell, cell type, tissue, organ, region of the body, or a compartment, e.g., a cellular, tissue or organ compartment. The targeting molecule, moiety, or ligand can comprise a wide variety of entities. Such ligands can include naturally occurring molecules, or recombinant or synthetic molecules.

A targeting molecule may be a targeting peptide. Such a peptide comprises in an example contiguous sequence of amino acids, which is characterized by selective localization to an organ, tissue, or cell type.

Additional exemplary targeting ligands may be provided and include, but are not limited to, antibodies, antigen binding fragments of antibodies, antigens, folates, EGF, albumin, receptor ligands, carbohydrates, aptamers, integrin receptor ligands, chemokine receptor ligands, transferrin, biotin, serotonin receptor ligands, PSMA, endothelin, GCPII, somatostatin, LDL and HDL ligands. Additional exemplary ligands include, but are not limited to, polylysine (PLL), poly L-aspartic acid, poly L-glutamic acid, styrene-maleic acid anhydride copolymer, poly(L-lactide-co-gly-colied) copolymer, divinyl ether-maleic anhydride copolymer, N-(2-hydroxypropyl)methacrylamide copolymer (HMPA), polyethylene glycol (e.g., PEG-2K, PEG-5K, PEG-10K, PEG-12K, PEG-15K, PEG-20K, PEG-40K), MPEG, [MPEG]2, polyvinyl alcohol (PVA), polyurethane, poly(2-ethylacryllic acid), N-isopropylacrylamide polymers, polyphosphazine, polyethylenimine, cationic groups, spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, thyrotropin, melanotropin, lectin, glycoprotein, surfactant protein A, mucin, glycosylated polyaminoacids, transferrin, bisphosphonate, polyglutamate, polyaspartate, aptamer, asialofetuin, hyaluronan, procollagen, immunoglobulins (e.g., antibodies), insulin, transferrin, albumin, sugar-albumin conjugates, intercalating agents (e.g., acridines), cross-linkers (e.g. psoralen, mitomycin C), porphyrins (e.g., TPPC4, texaphyrin, Sapphyrin), polycyclic aromatic hydrocarbons (e.g., phenazine, dihydrophenazine), artificial endonucleases (e.g., EDTA), lipophilic molecules (e.g., steroids, bile acids, cholesterol, cholic acid, adamantane acetic acid, 1-pyrene butyric acid, dihydrotestosterone, 1,3-Bis-O(hexadecyl) glycerol, geranyloxyhexyl group, hexadecylglycerol, borneol, menthol, 1,3-propanediol, heptadecyl group, palmitic acid, myristic acid, 03-(oleoyl)lithocholic acid, 03-(oleoyl) cholenic acid, dimethoxytrityl, or phenoxazine), peptides (e.g., an alpha helical peptide, amphipathic peptide, RGD peptide, cell permeation peptide, endosomolytic/fusogenic peptide), alkylating agents, phosphate, amino, mercapto, polyamino, alkyl, substituted alkyl, radiolabeled markers, enzymes, haptens (e.g. biotin), transport/absorption facilitators (e.g., naproxen, aspirin, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP, AP, antibodies, hormones and hormone receptors, lectins, carbohydrates, multivalent carbohydrates, vitamins (e.g., vitamin A, vitamin E, vitamin K, vitamin B, e.g., folic acid, B12, riboflavin, biotin and pyridoxal), vitamin cofactors, lipopolysaccharide, an activator of p38 MAP kinase, an activator of NF-κB, taxon, vincristine, vinblastine, cytochalasin, nocodazole, japlakinolide, latrunculin A, phalloidin, swinholide A, indanocine, myoservin, tumor necrosis factor alpha (TNFα), interleukin-1 β, γ interferon, natural or recombinant low density lipoprotein (LDL), natural or recombinant high-density lipoprotein (HDL), and a cell-permeation agent (e.g., a.helical cell-permeation agent).

Peptide and peptidomimetic molecules include those having naturally occurring or modified peptides, e.g., D or L peptides; α, β, or γ peptides; N-methyl peptides; azapeptides; peptides having one or more amide, i.e., peptide, linkages replaced with one or more urea, thiourea, carbamate, or sulfonyl urea linkages; or cyclic peptides. A peptidomimetic (also referred to herein as an oligopeptidomimetic) is a molecule capable of folding into a defined three-dimensional structure similar to a natural peptide. The peptide or peptidomimetic ligand can be about 2-50 amino acids long, e.g., about 5, 10, 15, 20, 25, 30, 35, 40, 45, or 50 amino acids long.

Carbohydrate based targeting molecules include, but are not limited to, D-galactose, multivalent galactose, N-acetyl-D-galactose (GalNAc), multivalent GalNAc, e.g. GalNAc2 and GalNAc3; D-mannose, multivalent mannose, multivalent lactose, N-acetyl-galactosamine, N-acetyl-gulucosamine, multivalent fucose, glycosylated polyaminoacids and lectins. The term multivalent indicates that more than one monosaccharide unit is present. Such monosaccharide subunits can be linked to each other through glycosidic linkages or linked to a scaffold molecule.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6} M^{-1}$ or lower. "Affinity" refers to the strength of binding: increased binding affinity being correlated with a lower $K_d$.

A binding molecule is a molecule such as a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

As used herein, the term "affinity peptide," "affinity moiety," or "affinity ligand" refers to any molecule that binds to a targeting ligand. Generally, the affinity ligand binds with the targeting ligand at a site that does not inhibit or reduce binding of the targeting ligand to its target.

Without limitation, the affinity molecule or ligand can be selected from the group consisting of small organic or inorganic molecules, peptides, proteins, peptide derivatives and analogs, peptidomimetics, nucleic acids, nucleic acid derivatives and acid analogs, saccharines, oligosaccharides, polysaccharides, lipids, glycoproteins, glycopeptides, and any combinations thereof.

The targeting molecule, peptide, targeting ligand, or affinity ligand can be linked or conjugated to the molecule of interest such that the targeting molecule delivers the molecule of interest to the oocyte. The method of linking is not limited to any particular methodology and will vary depending upon the application and refers to two or more molecules joined. The molecules may be fused, may be associated by providing additional molecules having affinity to each other such as streptavidin and biotin, may be joined by a linker or any convenient methods.

In one example they may be joined via a linker. As used herein, the term "linker" means an organic moiety that connects two parts of a compound. Linkers typically comprise a direct bond or an atom such as oxygen or sulfur, a unit such as NH, C(O), C(O)NH, SO, $SO_2$, $SO_2NH$ or a chain of atoms, such as substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, where one or more methylenes can be interrupted or terminated by O, S, S(O), SO$_2$, NH, C(O). The terms linker and spacer are used interchangeably herein. The linker can comprise any combinations of the above. Accordingly, in some embodiments, the linker can comprise hydrocarbons, amino acids, peptides, polyethylene glycol of various lengths, cyclodextrins, and derivatives and any combinations thereof.

A linker may also be a "branched linker." By a branched linker is meant a linker that can connect together three or more part together. The branch-point of the branched linker may be at least trivalent, but can be a tetravalent, pentavalent or hexavalent atom, or a group presenting such multiple valencies. In some embodiments, the branchpoint is —N, —N(Q)-C, —O—C, —S—C, —SS—C, —C(O)N(Q)-C, —OC(O)N(Q)-C, —N(Q)C(O)—C, or —N(Q)C(O)O—C; wherein Q is independently for each occurrence H or optionally substituted alkyl. In some embodiments, the branchpoint is glycerol or derivative thereof, and normal chain sugars such as monosaccharides and polysaccharides. A branched linker can be used to connect two or more (e.g., 2, 3, 4, 5, 6, 7, 8, 9, 10 or more) molecules of interest (which can be same or different) to one affinity ligand; two or more (e.g., 2, 3, 4, 5, 6, 7, 8, 9, 10 or more) affinity ligands (which can be same or different) to one molecule of interest; or two or more (e.g., 2, 3, 4, 5, 6, 7, 8, 9, 10 or more) molecules of interest (which can be same or different) to two or more (e.g., 2, 3, 4, 5, 6, 7, 8, 9, 10 or more) affinity ligands (which can be same or different).

A linker may comprise of at least one cleavable linking group. A cleavable linking group is one which is sufficiently stable outside the cell, but which upon entry into a target cell is cleaved to release the two parts the linker is holding together. In a preferred embodiment, the cleavable linking group is cleaved at least 10 times or more, preferably at least 100 times faster in the target cell or under a first reference condition (which can, e.g., be selected to mimic or represent intracellular conditions) than in the blood or serum of a subject, or under a second reference condition (which can, e.g., be selected to mimic or represent conditions found in the blood or serum).

Cleavable linking groups are susceptible to cleavage agents, e.g., pH, redox potential or the presence of degradative molecules. Generally, cleavage agents are more prevalent or found at higher levels or activities inside cells than in serum or blood. Examples of such degradative agents include: redox agents which are selected for particular substrates or which have no substrate specificity, including, e.g., oxidative or reductive enzymes or reductive agents such as mercaptans, present in cells, that can degrade a redox cleavable linking group by reduction; esterases; amidases; endosomes or agents that can create an acidic environment, e.g., those that result in a pH of five or lower; enzymes that can hydrolyze or degrade an acid cleavable linking group by acting as a general acid, peptidases (which can be substrate specific) and proteases, and phosphatases. The cleavable linking group can comprise esters, peptides, carbamates, acid-labile, reduction-labile, oxidation-labile, disulfides, and modifications thereof.

A linker can include a cleavable linking group that is cleavable by a particular enzyme. The type of cleavable linking group incorporated into a linker can depend on the cell to be targeted. In some embodiments, cleavable linking group is cleaved at least 1.25, 1.5, 1.75, 2, 3, 4, 5, 10, 25, 50, or 100 times faster in the cell (or under in vitro conditions selected to mimic intracellular conditions) as compared to blood or serum (or under in vitro conditions selected to mimic extracellular conditions). In some embodiments, the cleavable linking group is cleaved by less than 90%, 80%, 70%, 60%, 50%, 40%, 30%, 20%, 10%, 5%, or 1% in the blood (or in vitro conditions selected to mimic extracellular conditions) as compared to in the cell (or under in vitro conditions selected to mimic intracellular conditions).

Exemplary cleavable linking groups include, but are not limited to, redox cleavable linking groups (e.g., —S— and —C(R)$_2$—S—, wherein R is H or C$_1$-C$_6$ alkyl and at least one R is C$_1$-C$_6$ alkyl such as CH$_3$ or CH$_2$CH$_3$); phosphate-based cleavable linking groups (e.g., —O—P(O)(OR)—O—, —O—P(S)(OR)—O—, —O—P(S)(SR)—O—, —S—P(O)(OR)—O—, —O—P(O)(OR)—S—, —S—P(O)(OR)—S—, —O—P(S)(ORk)-S—, —S—P(S)(OR)—O—, —O—P(O)(R)—O—, —O—P(S)(R)—O—, —S—P(O)(R)—O—, —S—P(S)(R)—O—, —S—P(O)(R)—S—, —O—P(S)(R)—S—, —O—P(O)(OH)—O—, —O—P(S)(OH)—O—, —O—P(S)(SH)—O—, —S—P(O)(OH)—O—, —O—P(O)(OH)—S—, —S—P(O)(OH)—S—, —O—P(S)(OH)—S—, —S—P(S)(OH)—O—, —O—P(O)(H)—O—, —O—P(S)(H)—O—, —S—P(O)(H)—O—, —S—P(S)(H)—O—, —S—P(O)(H)—S—, and —O—P(S)(H)—S—, wherein R is optionally substituted linear or branched C$_1$-C$_{10}$ alkyl); acid cleavable linking groups (e.g., hydrazones, esters, and esters of amino acids, —C=NN— and —OC(O)—); ester-based cleavable linking groups (e.g., —C(O)O—); peptide-based cleavable linking groups, (e.g., linking groups that are cleaved by enzymes such as peptidases and proteases in cells, e.g., —NHCHR$^A$C(O)NHCHR$^B$C(O)—, where R$^A$ and R$^B$ are the R groups of the two adjacent amino acids). A peptide based cleavable linking group comprises two or more amino acids. In some embodiments, the peptide-based cleavage linkage comprises the amino acid sequence that is the substrate for a peptidase or a protease found in cells.

The cleavable linking group can be located anywhere in the linker. For example, the cleavable linking group can be located at a terminus of the linker. In some embodiments, the cleavable linking group is located at the linker terminus distal to the affinity ligand. In some embodiments, the cleavable linking group is located at the linker terminus distal to the molecule of interest, e.g., therapeutic agent. In some embodiments, the cleavable linking group is in the linker itself. In some embodiments, the cleavable linking group connects the linker to the molecule of interest, e.g., therapeutic agent. In some embodiments, the cleavable linking group connects the linker to the affinity ligand. Thus, in some embodiments, the linker can be linked to the affinity ligand and/or the molecule of interest via a cleavable linking group.

A "macromolecular complex" refers to a collection of molecules that may be random, ordered or partially ordered in their arrangement. The term encompasses biological organisms such as bacteriophage, viruses, bacteria, unicellular pathogenic organisms, multicellular pathogenic organisms and prokaryotic or eukaryotic cells. The term also encompasses non-living assemblages of molecules, such as liposomes, microcapsules, microparticles, magnetic beads and microdevices. The only requirement is that the complex contains more than one molecule. The molecules may be identical or may differ from each other.

A "receptor" is a molecular structure or site that binds with another molecules. Receptors may be peptides, proteins, glycoproteins, lipoproteins, epitopes, antibodies, lipids, carbohydrates, multi-molecular structures, a specific conformation of one or more molecules and a morphoanatomic entity that has a binding affinity for a specific group of chemicals or molecules, such as other proteins or viruses.

"Ribonuclear protein" (RNP) is an association of a RNA-binding protein and a ribonucleic acid.

"Fuse," "fused," "fusion," or "chimeric" proteins are proteins created by joining two or more genes or parts of genes that originally code for separate proteins. A "linker" or "spacer" sequence may be placed between the fusion proteins to help ensure proper folding and function are maintained. Alternatively, linker sequence may contain cleavage sights so the fused proteins may be separated.

Without limitations any molecule of interest can be conjugated to the targeting peptide. This can include without limitation a therapeutic agent. Embodiments provide the molecule of interest can inhibit, increase, decrease, or otherwise modify nucleic acid expression, or protein or cell function. It may provide for identification of an associated sequence or molecule, through, for example, labeling or detection, may provide for binding to another substance for purification, or any one of a myriad of uses. Such various uses are discussed further herein.

As used herein, the term "therapeutic agent" refers to a substance used in the diagnosis, treatment, or prevention of a disease or other undesirable state. Any therapeutic agent known to those of ordinary skill in the art to be of benefit in the diagnosis, treatment or prevention of a undesired state is contemplated as a therapeutic agent. Therapeutic agents include pharmaceutically active compounds, hormones, growth factors, enzymes, DNA, plasmid DNA, RNA, siRNA, antisense oligonucleotides, aptamers, ribozymes, viruses, proteins, lipids, pro-inflammatory molecules, antibodies, antibiotics, anti-inflammatory agents, anti-sense nucleotides and transforming nucleic acids or combinations thereof. Any of the therapeutic agents can be combined to the extent such combination is biologically compatible. The therapeutic agent is selected according to the treatment objective and biological action desired. Other molecules which may be conjugated include polynucleotides for genetic modification, and the like.

The term "sequence" refers to a nucleotide sequence of any length, which can be DNA or RNA; can be linear, circular or branched and can be either single-stranded or double stranded. The term "donor sequence" refers to a molecule of interest that is a nucleotide sequence that is inserted into a genome. A donor sequence can be of any length, for example between 1, 2 and 10,000 nucleotides in length (or any integer value there between or thereabove), between about 100 and 1,000 nucleotides in length (or any integer there between), between about 200 and 500 nucleotides in length or any length convenient to the desired result.

The terms "polypeptide," "peptide" and "protein" are used interchangeably to refer to a polymer of amino acid residues. The term also applies to amino acid polymers in which one or more amino acids are chemical analogues or modified derivatives of a corresponding naturally-occurring amino acids.

As used herein, amino acids include natural or unnatural amino acids. Thus, as used herein, the term "amino acid" includes compounds which depart from the structure of the naturally occurring amino acids, but which have substantially the structure of an amino acid, such that they can be substituted within a peptide which retains is activity, e.g., biological activity. Thus, for example, in some embodiments amino acids can also include amino acids having side chain modifications or substitutions, and also include related organic acids, amides or the like. Without limitation, an amino acid can be a proteogenic or non-proteogenic amino acid. As used herein, the term "proteogenic" indicates that the amino acid can be incorporated into a protein in a cell through well-known metabolic pathways. Exemplary amino acids include, but are not limited to, alanine; argnine; asparagine; aspartic acid; cysteine; glutamic acid; glutamine; glycine; histadine; isoleucine; leucine; lysine; methionine; phenylalanine; proline; serine; threonine; tryptophan; tyrosine; valine; homocysteine; phosphoserine; phosphothreonine; phosphotyrosine; hydroxyproline; γ-carboxyglutamate; hippuric acid; octahydroindole-2-carboxylic acid; statine; 1,2,3,4,-tetrahydroisoquinoline-3-carboxylic acid; penicillamine (3-mercapto-D-valine); ornithine (Orn); citruline; alpha-methyl-alanine; para-benzoylphenylalanine; para-aminophenylalanine; p-fluorophenylalanine; phenylglycine; propargylglycine; N-methylglycins (sarcosine, Sar); and tert-butylglycine; diaminobutyric acid; 7-hydroxy-tetrahydroisoquinoline carboxylic acid; naphthylalanine; biphenylalanine; cyclohexylalanine; amino-isobutyric acid (Aib); norvaline; norleucine (Nle); tert-leucine; tetrahydroisoquinoline carboxylic acid; pipecolic acid; phenylglycine; homophenylalanine; cyclohexylglycine; dehydroleucine; 2,2-diethylglycine; 1-amino-1-cyclopentanecarboxylic acid; 1-amino-1-cyclohexanecarboxylic acid; amino-benzoic acid; amino-naphthoic acid; γ-aminobutyric acid; difluorophenylalanine; nipecotic acid; N-α-imidazole acetic acid (IMA); thienyl-alanine; t-butylglycine; desamino-Tyr; aminovaleric acid (Ava); pyroglutaminic acid (Glp); α-aminoisobutyric acid (αAib); γ-aminobutyric acid (γAbu); α-aminobutyric acid (αAbu); αγ-aminobutyric acid (αγAbu); 3-pyridylalanine (Pal); Isopropyl-α-N$^{\varepsilon}$-lysine (ILys); Napthyalanine (Nal); α-napthyalanine (α-Nal); β-napthyalanine (β-Nal); Acetyl-β-napthyalanine (Ac-β-napthyalanine); napthyalanine; 4-halo-Phenyl; 4-pyrolidyl-alanine; isonipecotic carboxylic acid (inip); β-amino acids; and isomers, analogs and derivatives thereof. One of skill in the art would know that this definition includes, D- and L-amino acids, α- and β-amino acids, chemically modified amino acids, naturally occurring non-proteogenic amino acids, rare amino acids, and chemically synthesized compounds that have properties known in the art to be characteristic of an amino acid.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" referred to herein as a "variant" where the alteration results in the substitution of an amino acid with a chemically similar amino acid. Conservative substitution tables providing functionally similar amino acids are well known in the art. See, for example, Davis et al., "Basic Methods in Molecular Biology" Appleton & Lange, Norwalk, Conn. (1994).

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., see, e.g., Creighton, Proteins: Structures and Molecular Properties (WH Freeman & Co.; 2nd edition (December 1993)).

Peptide modifications are well known in the art. Thus, a peptide described herein, e.g., a linker peptide, can comprise one or more peptide modifications known in the art. Exemplary peptide modifications for modifying the fusion protein described herein include, but are not limited to, D amino acids, a amino acids, β amino acids, non-amide or modified amide linkages, chemically modified amino acids, naturally occurring non-proteogenic amino acids, rare amino acids, chemically synthesized compounds that have properties known in the art to be characteristic of an amino acid, and the like. Thus, as used herein, peptide includes natural or unnatural amino acids, or a combination thereof.

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T. A nucleic acid can be single-stranded or double-stranded. A single-stranded nucleic acid can have double-stranded regions and a double-stranded nucleic acid can have single-stranded regions.
Synthetic Methods for Constructing Nucleic Acids The nucleic acids can also be prepared by direct chemical synthesis by methods such as the phosphotriester method of Narang, et al., (1979) Meth. Enzymol. 68:90 9; the phosphodiester method of Brown, et al., (1979) Meth. Enzymol. 68:109 51; the diethylphosphoramidite method of Beaucage, et al., (1981) Tetra. Letts. 22(20):1859 62; the solid phase phosphoramidite triester method described by Beaucage, et al., supra, e.g., using an automated synthesizer, e.g., as described in Needham VanDevanter, et al., (1984) Nucleic Acids Res. 12:6159 68; and, the solid support method of U.S. Pat. No. 4,458,066. Chemical synthesis generally produces a single stranded oligonucleotide. This may be converted into double stranded DNA by hybridization with a complementary sequence or by polymerization with a DNA polymerase using the single strand as a template. One of skill will recognize that while chemical synthesis of DNA is limited to sequences of about 100 bases, longer sequences may be obtained by the ligation of shorter sequences.
Sequence Shuffling The present processes may use methods for sequence shuffling using polynucleotides, and compositions resulting therefrom. Sequence shuffling is described in PCT Publication No. 96/19256. See also, Zhang, et al., (1997) Proc. Natl. Acad. Sci. USA 94:4504-9; and Zhao, et al., (1998) Nature Biotech 16:258-61. Generally, sequence shuffling provides a means for generating libraries of polynucleotides having a desired characteristic, which can be selected or screened for. Libraries of recombinant polynucleotides are generated from a population of related sequence polynucleotides, which comprise sequence regions, which have substantial sequence identity and can be homologously recombined in vitro or in vivo. The population of sequence-recombined polynucleotides comprises a subpopulation of polynucleotides which possess desired or advantageous characteristics and which can be selected by a suitable selection or screening method. The characteristics can be any property or attribute capable of being selected for or detected in a screening system, and may include properties of: an encoded protein, a transcriptional element, a sequence controlling transcription, RNA processing, RNA stability, chromatin conformation, translation, or other expression property of a gene or transgene, a replicative element, a protein-binding element, or the like, such as any feature which confers a selectable or detectable property. In some embodiments, the selected characteristic will be an altered Km and/or Kcat over the wild-type protein as provided herein. In other embodiments, a protein or polynucleotide generated from sequence shuffling will have a ligand binding affinity greater than the non-shuffled wild-type polynucleotide. In yet other embodiments, a protein or polynucleotide generated from sequence shuffling will have an altered pH optimum as compared to the non-shuffled wild-type polynucleotide. The increase in such properties can be at least 110%, 120%, 130%, 140% or greater than 150% of the wild-type value.

Nucleic Acids

Provided here are nucleic acids of RNA, DNA, homologs, paralogs and orthologs and/or chimeras thereof, comprising Yolk Protein 1 (YP1) and subunits which retain the ability to bind to the receptor found at least one oocytes. This includes naturally occurring as well as synthetic variants and homologs of the sequences.

Sequences homologous, i.e., that share significant sequence identity or functional similarity, to those provided herein derived *Drosophila melanogaster* or from other oviparous species of choice, are also an aspect. Homologous sequences can be derived from any species including most invertebrates such as, but not limited to, mosquitoes and other *Drosophila* species; amphibians such as frogs and salamanders; birds such as chickens and ostrich; fish such as zebrafish; reptiles; and monotreme mammals such as platypus and echidna.
Orthologs and Paralogs Homologous sequences as described above can comprise orthologous or paralogous sequences. Several different methods are known by those of skill in the art for identifying and defining these functionally homologous sequences. Three general methods for defining orthologs and paralogs are described; an ortholog, paralog or homolog may be identified by one or more of the methods described below.

Orthologs and paralogs are evolutionarily related genes that have similar sequence and similar functions. Orthologs are structurally related genes in different species that are derived by a speciation event. Paralogs are structurally related genes within a single species that are derived by a duplication event Within a single animal species, gene duplication may cause two copies of a particular gene, giving rise to two or more genes with similar sequence and often similar function known as paralogs. A paralog is therefore a similar gene formed by duplication within the same species. Paralogs typically cluster together or in the same clade (a group of similar genes) when a gene family phylogeny is analyzed using programs such as CLUSTAL (Thompson et al. (1994) Nucleic Acids Res. 22: 4673-4680; Higgins et al. (1996) Methods Enzymol. 266: 383-402). Groups of similar genes can also be identified with pair-wise BLAST analysis (Feng and Doolittle (1987) J. Mol. Evol. 25: 351-360).

For example, a clade of very similar HOX domain transcription factors from *Drosophila* all share a common function in development. Analysis of groups of similar genes with similar function that fall within one clade can yield sub-sequences that are particular to the clade. These sub-sequences, known as consensus sequences, can not only be used to define the sequences within each clade, but define the functions of these genes; genes within a clade may contain paralogous sequences, or orthologous sequences that share the same function (see also, for example, Mount (2001), in Bioinformatics: Sequence and Genome Analysis Cold Spring Harbor Laboratory Press, Cold Spring Harbor, N.Y., page 543.)

Speciation, the production of new species from a parental species, can also give rise to two or more genes with similar sequence and similar function. These genes, termed orthologs, often have an identical function within their host animal and are often interchangeable between species without losing function. Because animals have common ancestors, many genes in any animal species will have a corresponding orthologous gene in another animal species. Once a phylogenic tree for a gene family of one species has been constructed using a program such as CLUSTAL (Thompson et al. (1994) Nucleic Acids Res. 22: 4673-4680; Higgins et al. (1996) supra) potential orthologous sequences can be placed into the phylogenetic tree and their relationship to genes from the species of interest can be determined. Orthologous sequences can also be identified by a reciprocal BLAST strategy. Once an orthologous sequence has been identified, the function of the ortholog can be deduced from the identified function of the reference sequence.

Orthologous genes from different organisms have highly conserved functions, and very often essentially identical functions (Lee et al. (2002) Genome Res. 12: 493-502; Remm et al. (2001) J. Mol. Biol. 314: 1041-1052). Paralogous genes, which have diverged through gene duplication, may retain similar functions of the encoded proteins. In such cases, paralogs can be used interchangeably with respect to certain embodiments of the instant invention (for example, transgenic expression of a coding sequence).

The term "conservatively modified variants" applies to both amino acid and nucleic acid sequences. With respect to nucleic acid sequences, a conservatively modified variant refers to those nucleic acids which encode identical or conservatively modified variants of the amino acid sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation. Every nucleic acid sequence herein that encodes a polypeptide also, by reference to the genetic code, describes every possible silent variation of the nucleic acid. One of ordinary skill will recognize that each codon in a nucleic acid (except AUG, which is ordinarily the only codon for methionine; and UGG, which is ordinarily the only codon for tryptophan) can be modified to yield a functionally identical molecule. Accordingly, each silent variation of a nucleic acid which encodes a polypeptide is implicit in each described polypeptide sequence and is within the scope.

"Cleavage" refers to the breakage of the covalent bond, such as that of the backbone of a DNA molecule. Cleavage can be initiated by a variety of methods including, but not limited to, enzymatic or chemical hydrolysis of a phosphodiester bond. Both DNA single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

An "exogenous" or "heterologous" molecule is a molecule that is not normally present in a cell, or not present at a native locus, but can be introduced into a cell by one or more genetic, biochemical, or other methods. Normal presence in the cell is determined with respect to the particular developmental stage and environmental conditions and presentation at a particular locus of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell By contrast, an "endogenous" molecule is one that is normally present in a particular cell at a particular developmental stage or locus or under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of a mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" or modification of gene expression refers to a change in expression or the activity of a gene or the resulting encoded peptide. Modulation of expression can include, but is not limited to, gene activation and gene repression. Nucleic acids of use include those that encode an entire polypeptide or produce an RNA sequence as well as those that encode a subsequence of the polypeptide or RNA or produce a fragment of an interfering RNA. Such molecules can interfere with expression of a target gene or its product. By way of example without intending to be limiting, such methods can include antisense, transcriptional activation, dominant negative mutation protein use, co-suppression, repressor systems, protease and ribozyme encoding sequences, site-direct mutagenesis and other mutagenesis methods, and homologous recombination.

Expression of the sense and antisense molecules can be accomplished by designing the expression cassette to comprise both a sense sequence and an antisense sequence. Alternatively, separate expression cassettes may be used for the sense and antisense sequences. Hosts transformed with the dsRNA interference expression cassette or expression cassettes are then screened to identify those that show the greatest inhibition of polypeptide expression.

Methods for using dsRNA interference to inhibit the expression of endogenous genes are described in Waterhouse et al. (1998) Proc. Natl. Acad. Sci. USA 95:13959-13965, Liu et al. (2002) Plant Physiol. 129:1732-1753, WO 99/53050, and WO 99/61631. In some embodiments, inhibition of the expression of one or more target polypeptide may be obtained by hairpin RNA (hpRNA) interference or intron-containing hairpin RNA (ihpRNA) interference.

These methods are highly efficient at inhibiting the expression of endogenous genes. See, Waterhouse and Helliwell (2003) Nat. Rev. Genet. 4:29-38 and the references cited therein.

For hpRNA interference, the expression cassette is designed to express an RNA molecule that hybridizes with itself to form a hairpin structure that comprises a single-stranded loop region and a base-paired stem. The base-paired stem region comprises a sense sequence corresponding to all or part of the endogenous messenger RNA encoding the gene whose expression is to be inhibited, and an antisense sequence that is fully or partially complementary to the sense sequence. Thus, the base-paired stem region of the molecule generally determines the specificity of the RNA interference. hpRNA molecules are highly efficient at inhibiting the expression of endogenous genes, and the RNA interference they induce is inherited. See, for example, Chuang and Meyerowitz (2000) Proc. Natl. Acad. Sci. USA 97:5985-5990; Stoutjesdijk et al. (2002) Plant Physiol. 129: 1723-1731; and Waterhouse and Helliwell (2003) Nat. Rev. Genet. 5:29-38. Methods for using hpRNA interference to inhibit or silence the expression of genes are described, for example, in Chuang and Meyerowitz (2000) Proc. Natl. Acad. Sci. USA 97:5985-5990; Stoutjesdijk et al. (2002) Plant Physiol. 129:1723-1731; Waterhouse and Helliwell (2003) Nat. Rev. Genet. 5:29-38; Pandolfini et al. BMC Biotechnology 3:7, and U.S. Patent Publication No. 20030175965. hairpin RNAs having the ability to suppress expression of a gene have been described (see, e.g., Matzke et al. (2001) Curr. Opin. Genet. Devel. 11:221-227; Scheid et al. (2002) Proc. Natl. Acad. Sci., USA 99:13659-13662; Waterhouse and Helliwell (2003) supra; Aufsaftz et al (2002) Proc. Nat'l. Acad. Sci. 99(4):16499-16506; and Sijen et al., Curr. Biol. (2001) 11:436-440) A transient assay for the efficiency of hpRNA constructs to silence gene expression in vivo has been described by Panstruga et al. (2003) Mol. Biol. Rep. 30:135-150.

For ihpRNA, the interfering molecules have the same general structure as for hpRNA, but the RNA molecule additionally comprises an intron that is capable of being spliced in the cell in which the ihpRNA is expressed. The use of an intron minimizes the size of the loop in the hairpin RNA molecule following splicing, and this increases the efficiency of interference. See, for example, Smith et al. (2000) Nature 507:319-320. In fact, Smith et al. show 100% suppression of endogenous gene expression using ihpRNA-mediated interference. Methods for using ihpRNA interference to inhibit the expression of endogenous genes are described, for example, in Smith et al. (2000) Nature 507: 319-320; Wesley et al. (2001) Plant J. 27:581-590; Wang and Waterhouse (2001) Curr. Opin. Plant Biol. 5:156-150; Waterhouse and Helliwell (2003) Nat. Rev. Genet. 5:29-38; and Helliwell and Waterhouse (2003) Methods 30:289-295.

The expression cassette for hpRNA interference may also be designed such that the sense sequence and the antisense sequence do not correspond to an endogenous RNA. In this embodiment, the sense and antisense sequence flank a loop sequence that comprises a nucleotide sequence corresponding to all or part of the endogenous messenger RNA of the target gene. Thus, it is the loop region that determines the specificity of the RNA interference. See, for example, WO 02/00905.

Still other systems use "repressor" genes which inhibit the expression of another gene critical to male sterility. See, e.g., Haseloff et al., Nature 334: 585-591 (1988) describing design and use of target RNA-specific ribozymes, and U.S. Pat. No. 5,987,071, and WO 90/08829, using a binding protein to bind an operator. Inhibition of the expression of one or more target polypeptides may be obtained by RNA interference by expression of a gene encoding a micro RNA (miRNA). miRNAs are regulatory agents consisting of about 22 ribonucleotides. miRNA are highly efficient at inhibiting the expression of endogenous genes. See, for example Javier et al. (2003) Nature 525: 257-263, herein incorporated by reference. For miRNA interference, the expression cassette is designed to express an RNA molecule that is modeled on an endogenous miRNA gene. The miRNA gene encodes an RNA that forms a hairpin structure containing a 22-nucleotide sequence that is complementary to another endogenous gene (target sequence).

Gene editing may be accomplished using the methods described herein. Methods which provides for targeting of the molecule of interest (MOI) to the target site of the target gene may be utilized in the method. The following is provided by way of example rather than limitation. In referring to a target gene or molecule is meant to refer to any molecule within the animal genome desired to be modified as described or where it is desired, for example, to delete or insert a nucleic acid molecule or modify the molecule in some manner. Where the target molecule is a nucleic acid sequence, the target molecule can, for example, be a sequence coding a gene product (e.g., a protein) or a non-coding sequence (e.g., a regulatory polynucleotide or a junk DNA).

A guide nucleic acid molecule is one that directs the nuclease to the specific cut site in the genome, whether via use of a binding domain, recognition domains, guide RNAs or other mechanisms. The guide nucleic acid molecule is introduced into the cell under conditions appropriate for operation of the guide nucleic acid molecule in directing cleavage to the target locus. A person of skill in the art will have available a number of methods that may be used, the most common utilizing a nuclease to cleave the target region of the gene, along with sequences which will recognize sequences at the target locus and direct cleavage to the locus. Any nuclease that can cleave the phosphodiester bond of a polynucleotide chain may be used in the methods described here. By way of example without limitation, available systems include those utilizing site specific nucleases (SSN) such as ZFNs (Zinc finger nuclease), (Whyte, J. J. et al. Gene targeting with zinc finger nucleases to produce cloned eGFP knockout pigs. *Mol Reprod Dev* 78, 2 (2011); Whyte, et al. Cell Biology Symposium: Zinc finger nucleases to create custom-designed modifications. *J Anim Sci* 90, 1111-1117 (2012)); TALENs (Transcription activator-like effector nucleases) (see, Carlson, D. F. et al. Efficient TALEN-mediated gene knockout in animals. *Proc Natl Acad Sci USA* 109, 17382-17387 (2012); Tan, W. et al. Efficient nonmeiotic allele introgression in livestock using custom endonucleases. *Proc Natl Acad Sci USA* 110, 16526-16531 (2013); and the CRISPR (Clustered regularly interspaced short palindromic repeats)-associated (Cas) nuclease system (Hai, T., Teng, F., Guo, R., Li, W. & Zhou, Q. One-step generation of knockout pigs by zygote injection of CRISPR/Cas system. *Cell Res* 24, 372-375 (2014)) that have permitted editing of animal genomes. The use of recombinases such as FLP/FRT as described in U.S. Pat. No. 6,720,475, or CRE/LOX as described in U.S. Pat. No. 5,658,772, can be utilized to integrate a polynucleotide sequence into a specific chromosomal site. Meganucleases have been used for targeting donor polynucleotides into a specific chromosomal location as described in Puchta et al., *PNAS USA* 93 (1996) pp. 5055-5060. ZFNs work with proteins or domains of proteins binding to a binding domain having a stabilized structure as a result of use a zinc ion. TALENs utilize domains with repeats of amino acids which can specifically recognize a base pair in a DNA sequence. For a discussion of both systems see Voytas et al. U.S. Pat. No. 8,697,853, incorporated herein by reference in its entirety. These systems utilize enzymes prepared for each target sequence.

The process is useful with knockins and knockouts. One can upregulate gene transcription through insertion of a transcriptional activator, for example, or repress expression using transcriptional repressors. Without intending to be limiting, among the variety of utilities of gene editing include modifying (e.g., deleting, inserting, translocating, inactivating, activating, mutating) a target polynucleotide in a multiplicity of cell types. In some embodiments the polypeptide expressed may be modified. There are a broad spectrum of applications in, e.g., gene therapy, drug screening, disease diagnosis, prognosis, increasing or decreasing growth and body composition, and improving quality or composition of animal products. The methods are useful in any situation where modification of a disease gene is desired. Further examples include improved feed use and meat composition, enhanced reproductive performance, changing component content of animal products such as milk (such as lactose content), and, reduce or eliminate phenotypes such as boar taint phenotype. The process is useful with so-called knockins where a sequence is inserted in the genome or knockouts where gene expression is reduced or eliminated or interrupted. This allows for understanding and control of the gene and its' downstream impact.

CRISPR/Cas, TALENs and Zinc Finger Nucleases are examples of such gene editing.

The CRISPR/Cas nuclease system has evolved in archaea and bacteria as a RNA based adaptive immunity system to detect and cleave invading viruses and plasmids. (Horvath, P. & Barrangou, R. CRISPR/Cas, the immune system of bacteria and archaea. *Science* 327, 167-170 (2010); Wiedenheft, et al. RNA-guided genetic silencing systems in bacteria and archaea. *Nature* 482, 331-338 (2012)). Unlike ZFNs and TALENs, which require assembly of DNA binding domain (DBD) to direct the nuclease to the target site, the CRISPR/Cas system utilizes RNA as a guide. The CRISPR locus is a distinct class of interspersed short sequence repeats (SSRs) recognized in bacterial genes. The repeats are short elements occurring in clusters that are regularly spaced by unique intervening sequences with a substantially constant length. They were observed as an immunity system in which nucleic acid molecules homologous to virus or plasmid sequences are integrated into the CRISPR loci. The foreign DNA or RNA is targeted and cleaved. The system has been adapted for targeted insertion of a nucleic acid molecule at a defined locus. In general, a CRISPR system is characterized by elements that promote the formation of a CRISPR complex at the site of a target sequence to which a guide sequence is designed to have complementarity, where hybridization between a target sequence and a guide sequence promotes the formation of a CRISPR complex. Full complementarity is not necessarily required, provided there is sufficient complementarity to cause hybridization and promote formation of a CRISPR complex. In the CRISPR system one enzyme, a CRISPR enzyme is used for targeting using short RNA molecules.

Two basic components are used with the system, a guide RNA and an endonuclease. The guide RNA is endogenous sequence specifying the target site and tracrRNA, needed to bind to the enzyme. The guide sequence provides target specificity and the tracrRNA provides scaffolding properties. These guide sequences are typically about 15 up to 20 to 25 base pairs (bp) that hybridize with the target site and direct binding of a CRISPR complex to a target sequence. A sequence encoding a CRISPR-associated enzyme may be provided on the same or different vectors. Non-limiting examples of Cas proteins include Cas1, Cas1B, Cas2. Cas3, Cas4, Cas5, Cash. Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologs thereof, or modified versions thereof. In one embodiment the enzyme is a type II CRISPR system enzyme and is Cas9 or variants or modifications thereof. These enzymes are known; for example, the amino acid sequence of *S. pyogenes* Cas9 protein may be found in the SwissProt database under accession number Q99ZW2. The enzyme or Cas9 protein can be used as a nickase or nuclease and cleave one or two strands of DNA. Cas9 has two functional domains, RuvC and HNH and when both are used both strands are cleaved. Cas9 nuclease forms a ribonuclease complex with target CRISPR RNAs (crRNAs) and transactivating RNAs (tracrRNA), and uses the chimeric RNA to target the genomic sequence and induce DSB. The CRISPR/Cas nuclease and other SSN can introduce a targeted double strand break (DSB) in the genomic DNA, which in the presence of a single stranded (SS) DNA oligonucleotide or a double stranded (DS) targeting vector, result in homologous recombination (HR) based alteration of selected nucleotides or KI of transgenes respectively, into the target loci. In another embodiment a SS oligonucleotide having the nucleic acid molecule of interest may be used with Cas9 mRNA and sgRNA to target modification of a particular target gene region. In further embodiments the target gene is complementary to the gRNA sequence and will have a protospacer adjacent motif or PAM sequence. This aids in binding by Cas9. For a discussion of details of the CRISPR/Cas system see Cong et al., U.S. Pat. Nos. 8,932,814; 8,871,445 and 8,906,616, incorporated by reference herein in their entirety.

Breaks in the genome can be repaired by the non-homologous end joining DNA repair pathway (NHEJ) or by homology directed repair pathway (HDR). NHEJ can disrupt the gene, by causing frame shifts or premature stop codons to occur. HDR is an embodiment that provides for insertion of a nucleic acid molecule that avoids such issues. With a double strand break a DNA repair template is provided in which sequences are provided that have homology to and hybridize with genome sequences flanking the cleavage site (homology arm). In one embodiment the DNA template or flanking sequences are transfected into the cell with the CRISPR/Cas vector.

Even though HDR-based gene targeting events are extremely rare, the efficiencies can be improved by several orders of magnitude (>1000-fold) by introducing a DSB at the target locus (Moehle, E. A. et al. Targeted gene addition into a specified location in the human genome using designed zinc finger nucleases. *Proc Natl Acad Sci USA* 104, 3055-3060 (2007)). Following DSB, either a SS oligo, or a DS vector with homology to the ends flanking the DSB, can produce animals with targeted genomic alterations or transgene integrations (Cui, L et al. The permissive effect of zinc deficiency on uroguanylin and inducible nitric oxide synthase gene upregulation in rat intestine induced by interleukin 1alpha is rapidly reversed by zinc repletion. *The Journal of Nutrition* 133, 51-56 (2003); Meyer, M et al. Gene targeting by homologous recombination in mouse zygotes mediated by zinc-finger nucleases. *Proc Natl Acad Sci USA* 107, 15022-15026 (2010)).

Another programmable RNA-guided endonuclease of a class 2 CRISPR-Cas system also has been described and used for gene editing purposes (Zetsche et al., *Cell* 163:759-771, 2015). This system uses a non-specific endonuclease unit from the Cpf1 protein family, with a specificity of cleavage conferred by a single crRNA (lacking tracr RNA). Similar to Cas9, the Cpf1 coding sequence can be fused to UTR sequences described herein to improve its stability, and thus the efficiency of the resulting gene editing method.

Zinc Finger Nucleases use an endonuclease with a zinc finger protein domain recognizing a nucleotide triplet. Zinc fingers are DNA binding domains which recognize three bases and specificity can be altered by changing a few residues in or near an alpha helix in this domain. The cleavage domain of the DNA recognition domain and a cleavage domain are fused or two fusions products with the domain fused to a first cleavage half-domain and a fused separately to a second cleavage half-domain. See. e.g., US Publication 20050064472 incorporated herein by reference in its entirety, as are all references cited herein.

The "TALEN" method of engineering may also be utilized. TALEs are found in plant pathogenic bacteria in the genus *Xanthomonas*. These proteins play important roles in disease, or trigger defense, by binding host DNA and activating effector-specific host genes (see, e.g., Gu et al., *Nature* 435:1122-1125, 2005; Yang et al., *Proc. Natl. Acad. Sci. USA* 103:10503-10508, 2006; Kay et al. *Science* 318: 648-651, 2007; Sugio et al., *Proc. Natl. Acad. Sci. USA* 104:10720-10725, 2007; and Römer et al. *Science* 318:645-648, 2007). Specificity depends on an effector-variable number of imperfect, typically 34 amino acid repeats (Schornack et al., *J. Plant Physiol.* 163:256-272, 2006; and WO 2011/072246). Polymorphisms are present primarily at repeat positions 12 and 13, which are referred to herein as the repeat variable-diresidue (RVD).

The RVDs of TALEs correspond to the nucleotides in their target sites in a direct, linear fashion, one RVD to one nucleotide, with some degeneracy and no apparent context dependence. This mechanism for protein-DNA recognition enables target site prediction for new target specific TALEs, as well as target site selection and engineering of new TALEs with binding specificity for the selected sites.

TALE DNA binding domains can be fused to other sequences, such as endonuclease sequences, resulting in chimeric endonucleases targeted to specific, selected DNA sequences, and leading to subsequent cutting of the DNA at or near the targeted sequences. Such cuts (double-stranded breaks) in DNA can induce mutations into the wild-type DNA sequence via NHEJ or homologous recombination, for example. In some cases, TALE-nucleases can be used to facilitate site directed mutagenesis in complex genomes, knocking out or otherwise altering gene function with great precision and high efficiency. The fact that some endonucleases (e.g., FokI) function as dimers can be used to enhance the target specificity of the TALE-nuclease. When the two TALE-nuclease recognition sites are in close proximity the inactive monomers can come together to create a functional enzyme that cleaves the DNA. By requiring DNA binding to activate the nuclease, a highly site-specific restriction enzyme can be created.

By way of example, a method using TALENs for modifying the genetic material of a cell, can include (a) providing a cell containing a target DNA sequence; and (b) introducing a transcription activator-like (TAL) effector-DNA modifying enzyme into the cell, the TAL effector-DNA modifying enzyme comprising (i) a DNA modifying enzyme domain that can modify double stranded DNA, and (ii) a TAL effector domain comprising a plurality of TAL effector repeat sequences that, in combination, bind to a specific nucleotide sequence in the target DNA sequence, such that the TAL effector-DNA modifying enzyme modifies the target DNA within or adjacent to the specific nucleotide sequence in the cell or progeny thereof. The method can further include providing to the cell a nucleic acid comprising a sequence homologous to at least a portion of the target DNA sequence, such that homologous recombination occurs between the target DNA sequence and the nucleic acid. The target DNA can be chromosomal DNA. The introducing can comprise transfecting the cell with a vector encoding the TAL effector-DNA modifying enzyme, mechanically injecting the TAL effector-DNA modifying enzyme into the cell as a protein, delivering the TAL effector-DNA modifying enzyme into the cell as a protein by means of the bacterial type III secretion system, or introducing the TAL effector-DNA modifying enzyme into the cell as a protein by electroporation. The DNA modifying enzyme can be an endonuclease (e.g., a type II restriction endonuclease, such as FokI).

The TAL effector domain that binds to a specific nucleotide sequence within the target DNA can comprise 10 or more DNA binding repeats, and preferably 15 or more DNA binding repeats. Each DNA binding repeat can include a repeat variable-diresidue (RVD) that determines recognition of a base pair in the target DNA sequence, wherein each DNA binding repeat is responsible for recognizing one base pair in the target DNA sequence, and wherein the RVD comprises one or more of: HD for recognizing C; NG for recognizing T; NI for recognizing A; NN for recognizing G or A; NS for recognizing A or C or G or T; N* for recognizing C or T, where * represents a gap in the second position of the RVD; HG for recognizing T; H* for recognizing T, where * represents a gap in the second position of the RVD; IG for recognizing T; NK for recognizing G; HA for recognizing C; ND for recognizing C; HI for recognizing C; HN for recognizing G; NA for recognizing G; SN for recognizing G or A; and YG for recognizing T. Each DNA binding repeat can comprise a RVD that determines recognition of a base pair in the target DNA sequence, wherein each DNA binding repeat is responsible for recognizing one base pair in the target DNA sequence, and wherein the RVD comprises one or more of: HA for recognizing C; ND for recognizing C; HI for recognizing C; HN for recognizing G; NA for recognizing G; SN for recognizing G or A; YG for recognizing T; and NK for recognizing G, and one or more of: HD for recognizing C; NG for recognizing T; NI for recognizing A; NN for recognizing G or A; NS for recognizing A or C or G or T; N* for recognizing C or T, wherein * represents a gap in the second position of the RVD; HG for recognizing T; H* for recognizing T, wherein * represents a gap in the second position of the RVD; and IG for recognizing T.

Further embodiments of using TALENs include providing a method for generating a nucleic acid encoding a TAL effector specific for a selected nucleotide sequence, comprising: (1) linearizing a starter plasmid with PspXI, the starter plasmid comprising a nucleotide sequence that encodes a first TAL effector DNA binding repeat domain having a repeat variable-diresidue (RVD) specific for the first nucleotide of the selected nucleotide sequence, wherein the first TAL effector DNA binding repeat domain has a unique PspXI site at its 3' end; (2) ligating into the starter plasmid PspXI site a DNA module encoding one or more TAL effector DNA binding repeat domains that have RVDs specific for the next nucleotide(s) of the selected nucleotide sequence, wherein the DNA module has XhoI sticky ends; and (3) repeating steps (1) and (2) until the nucleic acid encodes a TAL effector capable of binding to the selected nucleotide sequence. The method can further comprise, after the ligating, determining the orientation of the DNA module in the PspXI site. The method can comprise repeating steps (1) and (2) from one to 30 times.

Still further TALEN methods are to generating a nucleic acid encoding a transcription activator-like effector endonuclease (TALEN), comprising (a) identifying a first nucleotide sequence in the genome of a cell; and (b) synthesizing a nucleic acid encoding a TALEN that comprises (i) a plurality of DNA binding repeats that, in combination, bind to the first unique nucleotide sequence, and (ii) an endonuclease that generates a double-stranded cut at a position within or adjacent to the first nucleotide sequence, wherein each DNA binding repeat comprises a RVD that determines recognition of a base pair in the target DNA, wherein each DNA binding repeat is responsible for recognizing one base pair in the target DNA, and wherein the TALEN comprises one or more of the above or other identified RVDs. In an example of further methods available, the first nucleotide sequence can meet at least one of the following criteria: i) is a minimum of 15 bases long and is oriented from 5' to 3' with a T immediately preceding the site at the 5' end; ii) does not have a T in the first (5') position or an A in the second position; iii) ends in T at the last (3') position and does not have a G at the next to last position; and iv) has a base composition of 0-63% A, 11-63% C, 0-25% G, and 2-42% T. The method can comprise identifying a first nucleotide sequence and a second nucleotide sequence in the genome of the cell, wherein the first and second nucleotide sequences meet at least one of the criteria set forth above and are separated by 15-18 bp. The endonuclease can generate a double-stranded cut between the first and second nucleotide sequences. Examples of methods of using TALENs may be found at Voytas et al., U.S. Pat. No. 8,697,853, incorporated herein by reference in its entirety.

TALENs utilize domains with repeats of amino acids which can specifically recognize a base pair in a DNA sequence. For a discussion of such systems see Voytas et al. U.S. Pat. No. 8,697,853, incorporated herein by reference in its entirety. These systems utilize enzymes prepared for each target sequence.

In some embodiments, the polynucleotide encodes an antibody that binds to at least one target polypeptide, and reduces the response regulator activity of the target polypeptide. In another embodiment, the binding of the antibody results in increased turnover of the antibody-type target polypeptide complex by cellular quality control mechanisms. The expression of antibodies in cells and the inhibition of molecular pathways by expression and binding of antibodies to proteins in pint cells are well known in the art. See, for example, Conrad and Sonnewald (2003) Nature Biotech. 21:35-36, incorporated herein by reference. In some embodiments, the activity of a target polypeptide is reduced or eliminated by disrupting the gene encoding the target polypeptide. The gene encoding the type A RR polypeptide may be disrupted by any method known in the art. For example, in one embodiment, the gene is disrupted by transposon tagging. In another embodiment, the gene is disrupted by mutagenizing using random or targeted mutagenesis, and selecting for hosts that have reduced response regulator activity.

In one embodiment, transposon tagging is used to reduce or eliminate the response regulator activity of one or more target polypeptides. Transposon tagging comprises inserting a transposon within an endogenous type target polypeptide gene to reduce or eliminate expression of the target polypeptide. In such a process, the expression of one or more target polypeptides is reduced or eliminated by inserting a transposon within a regulatory region or coding region of the gene encoding the target polypeptide. A transposon that is within an exon, intron, 5' or 3' untranslated sequence, a promoter, or any other regulatory sequence of a target gene may be used to reduce or eliminate the expression and/or activity of the encoded target polypeptide.

Methods for the transposon tagging of specific genes in are well known in the art. See, for example, Maes et al. (1999) Trends Plant Sci. 5:90-96; Dharmapuri and Sonti (1999) FEMS Microbiol. Lett. 179:53-59; Meissner et al. (2000) Plant J. 22:265-275; Phogat et al. (2000) J. Biosci. 25:57-63; Walbot (2000) Curr. Opin. Plant Biol. 2:103-107; Gai et al. (2000) Nucleic Acids Res. 28:95-96; Fitzmaurice et al. (1999) Genetics 153:1919-1928). In addition, the TUSC process for selecting Mu insertions in selected genes has been described in Bensen et al. (1995) Plant Cell 7:75-85; Mena et al. (1996) Science 275:1537-1550; and U.S. Pat. No. 5,962,765, incorporated herein by reference.

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

As used herein, "genetically modified cell" refers to a cell, which has been altered "by the hand of man." A genetically modified cell includes a cell, callus, tissue, or animal into which has been introduced an exogenous polynucleotide. Genetically modified cell also refers to a cell that has been genetically manipulated such that endogenous nucleotides have been altered to include a mutation, such as a deletion, an insertion, a transition, a transversion, or a combination thereof. For instance, an endogenous coding region could be deleted. Such mutations may result in a polypeptide having a different amino acid sequence than was encoded by the endogenous polynucleotide. Another example of a genetically modified cell, callus, tissue, or animal is one having an altered regulatory sequence, such as a promoter, to result in increased or decreased expression of an operably linked endogenous coding region.

Unless otherwise specified, "a," "an," "the," and "at least one" are used interchangeably and mean one or more than one.

Also, herein, the recitations of numerical ranges by endpoints include all numbers subsumed within that range (e.g., 1 to 5 includes 1, 1.5, 2, 2.75, 3, 3.80, 4, 5, etc.).

"Guide ribonucleic acid," (gRNA) or "single stranded guide ribonucleic acid" (sgRNA) are heterologous RNA sequences with one part recognized by a Cas9 protein and another section designed to bind to a specific DNA sequence.

When the nucleic acid is prepared or altered synthetically, advantage can be taken of known codon preferences of the intended host where the nucleic acid is to be expressed. The term "nucleic acid construct" or "polynucleotide construct" means a nucleic acid molecule, either single-stranded or double-stranded, which is isolated from a naturally occurring gene or which has been modified to contain segments of nucleic acids in a manner that would not otherwise exist in nature. The term nucleic acid construct is synonymous with the term "expression cassette" when the nucleic acid construct contains the control sequences required for expression of a coding sequence.

In the present context, the term "expression vector" covers a DNA molecule, linear or circular, that comprises a segment encoding a polypeptide, and which is operably linked to additional segments that provide for its transcription.

As used herein, the term vector refers broadly to any plasmid or virus encoding an exogenous nucleic acid. The term should also be construed to include non-plasmid and non-viral compounds which facilitate transfer of nucleic acid into virions or cells, such as, for example, polylysine compounds and the like. The vector may be a viral vector that is suitable as a delivery vehicle for delivery of the nucleic acid, or mutant thereof, to a cell, or the vector may be a non-viral vector which is suitable for the same purpose. Examples of viral and non-viral vectors for delivery of DNA to cells and tissues are well known in the art and are described, for example, in Ma et al. (1997, Proc. Natl. Acad. Sci. U.S.A. 94:12744-12746). Examples of viral vectors include, but are not limited to, a recombinant vaccinia virus, a recombinant adenovirus, a recombinant retrovirus, a recombinant adeno-associated virus, a recombinant avian pox virus, and the like (Cranage et al., 1986, EMBO J. 5:3057-3063; U.S. Pat. No. 5,591,439). Examples of non-viral vectors include, but are not limited to, liposomes, polyamine derivatives of DNA, and the like.

For example, animal expression vectors may include (1) a cloned animal gene under the transcriptional control of 5' and 3' regulatory sequences and (2) a dominant selectable marker. Such animal expression vectors may also contain, if desired, a promoter regulatory region (e.g., one conferring inducible or constitutive, environmentally- or developmentally-regulated, or cell- or tissue-specific, tissue preferred or other scorable or selective expression), a transcription initiation start site, a ribosome binding site, an RNA processing signal, a transcription termination site, and/or a polyadenylation signal.

The term "host cell", as used herein, includes any cell type which is susceptible to transformation with a nucleic acid construct. By "host cell" is meant a cell which contains a vector and supports the replication and/or expression of the vector. Host cells may be prokaryotic cells such as *E. coli*, or eukaryotic cells such as yeast, insect, amphibian, or mammalian cells.

The terms promoter, promoter region or promoter sequence refer generally to transcriptional regulatory regions of a gene, which may be found at the 5' or 3' side of the coding region, or within the coding region, or within introns. Typically, a promoter is a DNA regulatory region capable of binding RNA polymerase in a cell and initiating transcription of a downstream (3' direction) coding sequence. The typical 5' promoter sequence is bounded at its 3' terminus by the transcription initiation site and extends upstream (5' direction) to include the minimum number of bases or elements necessary to initiate transcription at levels detectable above background. Within the promoter sequence is a transcription initiation site (conveniently defined by mapping with nuclease 51), as well as protein binding domains (consensus sequences) responsible for the binding of RNA polymerase. Examples of promoters under developmental control include promoters that initiate transcription only, or preferentially, in certain tissues, such as oocytes, fat, blood of animals. The operation of a promoter may also vary depending on its location in the genome. Thus, an inducible promoter may become fully or partially constitutive in certain locations.

The term "derivative" as used herein refers to a chemical substance related structurally to another, i.e., an "original" substance, which can be referred to as a "parent" compound. A "derivative" can be made from the structurally-related parent compound in one or more steps. In some embodiments, the general physical and chemical properties of a derivative can be similar to or different from the parent compound.

Yolk Protein 1 (YP1) sequences have been identified that specifically targets receptors on at least oocytes. YP1 or proteins of similar function may be introduced into the circulatory system of an organism, into the blood of vertebrates as well as into the hemolymph of invertebrates, through injection or through other means, such as genetic modification. Subunits of YP1 may also be used. For example, some embodiments are a 120 and a 41 amino acid subunit of the *Drosophila melanogaster* Yolk Protein 1 (DmYP) hereinafter called P2 (SEQ ID NO: 2) and P2C (SEQ ID NO: 3) respectively, that retain the binding function of Yolk Protein 1.

In other embodiments the Yolk Proteins can be isolated from other organisms including, but not limited to, other invertebrates, fish, birds, reptiles, amphibians, and monotremes. The sequences may be used in any animal or insect. Animal examples include without limitation, canine (e.g., dogs), feline (e.g., cats); equine (e.g., horses), bovine (e.g., cattle), ovine (e.g. sheep), caprine (e.g. goat) porcine animals (e.g., pigs) and rabbit, as well as in avians including, but not limited to, chickens, turkeys, ducks, geese, a quail, a pheasant, parrots, finches, hawks, crows and ratites (ostrich, emu, cassowary, and the like) as well as domestic fur animals such as ferrets, minks, mustilids, and fish such as fin-fish, shellfish, and other aquatic animals. Any insect may be included, and the method may be used, for example, in controlling mosquito population. Examples of means of controlling mosquito population include by disrupting formation of oocytes, producing nonbiting mosquitoes (see, e.g., Armbruster (2018) "Molecular pathways to nonbiting mosquitoes" PNAS 115(5) 836-838) preventing production of viable progeny, or passing to progeny a disabling condition that prevents the mosquito from transmitting disease to other animals, or a lethal condition, and further where the lethal condition can be passed to progeny prior to death of the parent. (For example, see Terenius et al. (2008) "Molecular genetic manipulation of vector mosquitoes" *Cell Host & Microbe* 4 (Servick (2018) "The microbes in a mosquito's guy may help fight malaria" *Science* doi:10.1126/science.aaq0811).

Construction of Nucleic Acids

The isolated nucleic acids can be made using (a) standard recombinant methods, (b) synthetic techniques, or combinations thereof. In some embodiments, the polynucleotides will be cloned, amplified, or otherwise constructed from a fungus or bacteria.

The nucleic acids may conveniently comprise sequences in addition to a polynucleotide. For example, a multi-cloning site comprising one or more endonuclease restriction sites may be inserted into the nucleic acid to aid in isolation of the polynucleotide. Also, translatable sequences may be inserted to aid in the isolation of the translated polynucleotide. For example, a hexa-histidine marker sequence provides a convenient means to purify the proteins Additional sequences may be added to such cloning and/or expression sequences to optimize their function in cloning and/or expression, to aid in isolation of the polynucleotide, or to improve the introduction of the polynucleotide into a cell.

If polypeptide expression is desired, it is generally desirable to include a polyadenylation region at the 3'-end of a polynucleotide coding region. The polyadenylation region can be derived from a variety of genes, or from T-DNA. The 3' end sequence to be added can be derived from, for example, the nopaline synthase or octopine synthase genes, or alternatively from another gene. Examples of such regulatory elements include, but are not limited to, 3' termination and/or polyadenylation regions such as SV40 polyA or those of the *Agrobacterium tumefaciens* nopaline synthase (nos) gene (Bevan, et al., (1983) Nucleic Acids Res. 12:369-85); the potato proteinase inhibitor II (PINII) gene (Keil, et al., (1986) Nucleic Acids Res. 14:5641-50.

An intron sequence can be added to the 5' untranslated region or the coding sequence of the partial coding sequence to increase the amount of the mature message that accumulates in the cytosol. Inclusion of a spliceable intron in the transcription unit in expression constructs has been shown to increase gene expression at both the mRNA and protein levels up to 1000-fold (Buchman and Berg, (1988) Mol. Cell Biol. 8:4395-4405; Callis, et al., (1987) Genes Dev. 1:1183-200). Such intron enhancement of gene expression is typically greatest when placed near the 5' end of the transcription unit. Use of maize introns Adh1-S intron 1, 2 and 6, the Bronze-1 intron are known in the art. See generally, The Maize Handbook, Chapter 116, Freeling and Walbot, eds., Springer, New York (1994).

The vector comprising the sequences from a polynucleotide will typically comprise a marker gene, which confers a selectable phenotype on cells. Usually, the selectable marker gene will encode antibiotic resistance, with suitable genes including genes coding for resistance to the antibiotic spectinomycin (e.g., the aada gene), the streptomycin phosphotransferase (SPT) gene coding for streptomycin resistance, the neomycin phosphotransferase (NPTII) gene encoding kanamycin or geneticin resistance, the hygromycin phosphotransferase (HPT) gene coding for hygromycin resistance, genes coding for resistance to herbicides which act to inhibit the action of acetolactate synthase (ALS), genes coding for resistance to herbicides which act to inhibit action of glutamine synthase, such as phosphinothricin or basta (e.g., the bar gene), or other such genes known in the art. The bar gene encodes resistance to the herbicide basta, and the ALS gene encodes resistance to the herbicide chlorsulfuron.

Typical vectors useful for expression of genes in prokaryotes, yeast, insects, animals, and higher plants are well known in the art. For animals and insects these include pUC19 and pBS. For plants these include vectors derived from the tumor-inducing (Ti) plasmid of *Agrobacterium tumefaciens* described by Rogers, et al. (1987), Meth. Enzymol. 153:253-77.

It is expected that those of skill in the art are knowledgeable in the numerous expression systems available for expression of a nucleic acid encoding a protein. No attempt to describe in detail the various methods known for the expression of proteins in prokaryotes or eukaryotes will be made.

One of skill would recognize that modifications could be made to a protein without diminishing its biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids (e.g., poly His) placed on either terminus to create conveniently located restriction sites or termination codons or purification sequences.

Expression of Proteins in Host Cells

The nucleic acid sequences described herein can be expressed in a variety of host cells, including, but not limited to, *E. coli*, other bacterial hosts, yeast, plant, mammalian, fungus, and various higher eukaryotic cells such as insect cells (e.g. SF3), the COS, CHO and HeLa cells lines and myeloma cell lines. The recombinant protein gene will typically be operably linked to appropriate expression control sequences for each host. For *E. coli* this can include a promoter such as the T7, trp, or lambda promoters, a ribosome binding site and preferably a transcription termination signal. For eukaryotic cells, the control sequences can include a promoter and often an enhancer (e.g., an enhancer derived from immunoglobulin genes, ie1, SV40, cytomegalovirus, etc.), and a polyadenylation sequence, and may include splice donor and acceptor sequences.

Alternatively, the bacterial, yeast, animal, or other promoter can direct expression of a polynucleotide in a specific tissue or may be otherwise under more precise environmental or developmental control. Such promoters are referred to here as "inducible" promoters. Environmental conditions that may affect transcription by inducible promoters include pathogen attack, anaerobic conditions, or the presence of light. Examples of inducible promoters are the Adh1 promoter, which is inducible by hypoxia or cold stress, the Hsp70 promoter, which is inducible by heat stress, the PPDK promoter, which is inducible by light, and polh, p6.9, and 39k promoters, which are all inducible by baculovirus infection.

Expression in Prokaryotes

Prokaryotic cells may be used as hosts for expression. Prokaryotes most frequently are represented by various strains of *E. coli*; however, other microbial strains may also be used. Commonly used prokaryotic control sequences which are defined herein to include promoters for transcription initiation, optionally with an operator, along with ribosome binding site sequences, include such commonly used promoters as the beta lactamase (penicillinase) and lactose (lac) promoter systems (Chang, et al., (1977) Nature 198: 1056), the tryptophan (trp) promoter system (Goeddel, et al., (1980) Nucleic Acids Res. 8:4057) and the lambda derived P L promoter and N-gene ribosome binding site (Shimatake, et al., (1981) Nature 292:128). The inclusion of selection markers in DNA vectors transfected in *E. coli* is also useful. Examples of such markers include genes specifying resistance to ampicillin, tetracycline, or chloramphenicol.

The vector is selected to allow introduction of the gene of interest into the appropriate host cell. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA. Expression systems for expressing a protein are available using *Bacillus* sp. and *Salmonella* (Palva, et al., (1983) Gene 22:229-35; Mosbach, et al., (1983) Nature 302:543-5).

Expression in Eukaryotes

Synthesis of heterologous proteins in yeast is well known. Sherman, et al., (1982) Methods in Yeast Genetics, Cold Spring Harbor Laboratory is a well-recognized work describing the various methods available to produce the protein in yeast. Two widely utilized yeasts for production of eukaryotic proteins are *Saccharomyces cerevisiae* and *Pichia pastoris*. Vectors, strains, and protocols for expression in *Saccharomyces* and *Pichia* are known in the art and available from commercial suppliers (e.g., Invitrogen). Suitable vectors usually have expression control sequences, such as promoters, including 3-phosphoglycerate kinase or alcohol oxidase, and an origin of replication, termination sequences and the like as desired. A protein, once expressed, can be isolated from yeast by lysing the cells and applying standard protein isolation techniques to the lysates or the pellets. The monitoring of the purification process can be accomplished by using Western blot techniques or radioimmunoassay of other standard immunoassay techniques.

The sequences encoding proteins can also be ligated to various expression vectors for use in transfecting cell cultures of, for instance, animal, mammalian, insect, or bacterial origin. Mammalian cell systems often will be in the form of monolayers of cells although mammalian cell suspensions may also be used. A number of suitable host cell lines capable of expressing intact proteins have been developed in the art, and include the HEK293, BHK21, and CHO cell lines. Expression vectors for these cells can include expression control sequences, such as an origin of replication, a promoter (e.g., the CMV promoter, a HSV tk promoter or pgk (phosphoglycerate kinase) promoter), an enhancer (Queen, et al., (1986) Immunol. Rev. 89:49), and necessary processing information sites, such as ribosome binding sites, RNA splice sites, polyadenylation sites (e.g., an SV40 large T Ag poly A addition site), and transcriptional terminator sequences. Other animal cells useful for production of proteins are available, for instance, from the American Type Culture Collection Catalogue of Cell Lines and Hybridomas (7th ed., 1992).

Appropriate vectors for expressing proteins in insect cells are usually derived from the SF9 baculovirus. Suitable insect cell lines include mosquito larvae, silkworm, armyworm, moth, and *Drosophila* cell lines such as a Schneider cell line (see, e.g., Schneider, (1987) J. Embryol. Exp. Morphol. 27:353-65).

As with yeast, when higher animal or other host cells are employed, polyadenlyation or transcription terminator sequences are typically incorporated into the vector. An example of a terminator sequence is the polyadenlyation sequence from the bovine growth hormone gene. Sequences for accurate splicing of the transcript may also be included. An example of a splicing sequence is the VP1 intron from SV40 (Sprague et al., J. Virol. 45:773 81 (1983)). Additionally, gene sequences to control replication in the host cell may be incorporated into the vector such as those found in bovine papilloma virus type vectors (Saveria-Campo, "Bovine Papilloma Virus DNA a Eukaryotic Cloning Vector," in DNA Cloning: A Practical Approach, vol. II, Glover, ed., IRL Press, Arlington, VA, pp. 213-38 (1985)).

In addition, the gene placed in the appropriate expression vector can be used to transform cells. The polypeptide can then be isolated from the transformed cells or media, Bacterial and Animal Transformation Methods The plasmids can be transferred into the chosen host cell by well-known methods such as calcium chloride transformation for *E. coli* and calcium phosphate treatment or electroporation for mammalian cells. Direct gene transfer and reagent based methods may also be used. Reagent based methods may include the use of LIPOFECTAMINE™ or SuperFect. Cells transformed by the plasmids can be selected by resistance to antibiotics conferred by genes contained on the plasmids, such as the amp, gpt, neo and hyg genes.

Conjugation of the Compound

These targeting molecules may be conjugated to various compounds to be used for many purposes such as, but not limited to, modification of gene expression or protein function; labeling and detection; delivery of the compound to cells expressing the corresponding receptor; binding to a stationary substrate for column purification. Conjugation can be accomplished in multiple ways. The following is provided by way of example without limitation. In one embodiment the conjugation is done by covalently bonding the compound to the targeting peptide. In another embodiment the compound is affinity bound directly to the targeting peptide. In a further embodiment, one or more linkers can be utilized to bind one or more compounds to the targeting peptide.

In some embodiments the linker is covalently bound to both the targeting peptide and the molecule of interest. In other embodiments the linker is covalently bound to either the targeting peptide or the molecule of interest and affinity bound to either the targeting peptide or molecule of interest. In other embodiments the linker is affinity bound to both the targeting peptide and the molecule of interest.

In some embodiments the targeting peptide is covalently bound to at least one molecule of interest. In other embodiments the targeting peptide is covalently bound to at least one molecule of interest and affinity bound to at least one molecule of interest. In some embodiments at least one molecule of interest is affinity bound to the target peptide.

In other embodiments at least one linker is covalently bound to the targeting peptide and covalently bound to at least one molecule of interest. In other embodiments at least one linker is covalently bound to the targeting peptide and affinity bound to at least one molecule of interest. In other embodiments at least one linker is affinity bound to the targeting peptide and covalently bound to at least one molecule of interest. In other embodiments at least one linker is covalently or affinity bound to the targeting peptide and covalently or affinity bound to at least one molecule of interest. In other embodiments a branched linker is bound to the targeting peptide and to at least one molecule of interest.

In some embodiments the targeting peptide and the compound are encoded by a heterologous nucleotide and are expressed as a chimeric polypeptide.

Preparation of the Conjugates

The targeting molecule may be attached to the active compound of therapeutic or diagnostic or other interest by chemical modification. Typically, the chemical methods rely on derivatization of the active agent (therapeutic or diagnostic) with the desired linking agent, and then reaction with the targeting peptide. The chemical methods of derivatization may be carried out using bifunctional cross-linking agents.

If the targeting molecule or active agent does not contain suitable moieties for effecting chemical linkage it can be derivatized. For example, the agent, such as Shiga toxin, gelonin or other such agent, can be derivatized such as by reaction with a linking agent, such as N-succinimidyl-3-(2-pyridyidithio)propionate (SPDP). In other embodiments, the targeted agent, such as shiga A chain, is modified at or near the N-terminus to include a cysteine residue, so that the resulting modified agent can react with the chemokine receptor-binding moiety protein without further derivatization.

Non-limiting examples of possible chemical groups involved in such the conjugation are: a carboxylic acid group on the targeting peptide, which could be reacted with an amino group on the active agent to form an amide group linking the targeting peptide and the active agent; an amino group on the targeting peptide, which could be reacted with a carboxylic acid group on the active agent (for example, the carboxylic acid group on a glutamate or aspartate side chain) to form an amide group linking the targeting peptide and the active agent; a disulfide group on the targeting peptide, which could be reacted with a thiol group on the active agent (for example, the thiol group on a cysteine side chain) to form a disulfide group linking the targeting peptide and the active agent.

Once conjugated, the conjugate generally will be purified to separate the conjugate from unconjugated targeting agents or from other contaminants. A large number of purification techniques are available for use in providing conjugates of a sufficient degree of purity to render them clinically useful.

In certain embodiments, the conjugate is a fusion protein of the targeting peptide and the therapeutic or other agent, in which case the fusion protein or peptide may be isolated or purified. Protein purification techniques are well known to those of skill in the art. These techniques involve, at one level, the homogenization and crude fractionation of the cells, tissue or organ to polypeptide and non-polypeptide fractions. The protein or polypeptide of interest may be further purified using chromatographic and electrophoretic techniques to achieve partial or complete purification (or purification to homogeneity). Analytical methods particularly suited to the preparation of a pure peptide are ion-exchange chromatography, gel exclusion chromatography, polyacrylamide gel electrophoresis, affinity chromatography, immunoaffinity chromatography and isoelectric focusing. A particularly efficient method of purifying peptides is fast performance liquid chromatography (FPLC) or even high performance liquid chromatography (HPLC).

Various techniques suitable for use in protein purification are well known to those of skill in the art. These include, for example, precipitation with ammonium sulphate, PEG, antibodies and the like, or by heat denaturation, followed by: centrifugation; chromatography steps such as ion exchange, gel filtration, reverse phase, hydroxylapatite and affinity chromatography; isoelectric focusing: gel electrophoresis; and combinations of these and other techniques.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

In some embodiments the targeting peptide and molecule of interest are both encoded on a single heterologous nucleic acid sequence. The nucleic acid sequence may be part of a vector, which may be an expression vector. If the vector is an expression vector, a target cell can be used to amplify and make a chimeric peptide sequence comprising both the targeting peptide and the molecule of interest. In some embodiments the host cell is prokaryotic. In other embodiments the host cell is eukaryotic. In some embodiments the host cell is part of the same organism in which contains the target receptors.

In some embodiments the targeting peptide and molecule of interest are injected in an organism such as, but not limited to, arthropods, amphibians, birds, or monotreme mammals and deliver their molecule of interest to a remote cell that recognizes the targeting peptide. In some embodiments the injection site is in the circulatory system and the remote cells are the germline cells.

Some embodiments pertain to a cell modified by the molecule of interest after the targeting peptide binds to the cell's receptor and gains entry to the cell.

The disclosure is further illustrated by the following example which should not be construed as limiting. The examples are illustrative only, and are not intended to limit, in any manner, any of the aspects described herein. The following examples do not in any way limit the invention. All references referred to herein are incorporated herein by reference.

EXAMPLES

We developed a technology called Receptor-Mediated Ovary Transduction of Cargo (ReMOT Control) to deliver Cas9 RNP to the insect germline by injection into adult females. We identified a small peptide that mediates transduction of Cas9 RNP from the hemolymph (insect "bloodstream") to the ovaries, resulting in "in utero" heritable editing of the offspring chromosomes. In *Aedes aegypti*, gene-editing efficiency is as high as 27%. Since germline uptake by receptor-mediated endocytosis is conserved in animals, ReMOT Control will be widely applicable across diverse systems.

Example 1

To show DmYP1 (or fragments thereof) act as suitable ligands to deliver protein cargo into mosquito oocytes, a DmYP1-EGFP, or fragments of DmYP1-EGFP, fusion protein was expressed and injected into the thorax of *Anopheles gambiae* females 12 and 24 h post-blood feeding (PBF).

Mosquitoes

*Anopheles gambiae* (Keele strain) and *Aedes aegypti* (Rock strain) were reared at 27° C., 75+/−10% relative humidity (RH), 12:12 light:dark (L:D) cycle in a walk-in environmental chamber. Larvae were fed with ground Koi pellets (*Ae. aegypti*) or Tetramin (*An. gambiae*) daily. Adults were provided ad lib with 10% sterilized sugar on a cotton wick. For injection experiments female mosquitoes were fed on expired anonymous human blood (Biospecialty Corp.) using a water-jacketed membrane feeding system.

Female Injections and Dissections

Injections were performed with an aspirator tube assembly (A5177, Sigma) fitted with a glass capillary needle. Adult females were immobilized at 4° C. following a bloodmeal and kept on ice during injection. Females were injected intrathoracically until no additional fluid would enter, at an approximate volume of 200 nl per female. To visually confirm EGFP in the ovaries following injection, ovaries were dissected, mounted in saline buffer mixed with SlowFade Gold® antifade reagent (Invitrogen), covered with a coverslip and imaged on an Olympus BX41 epifluorescent microscope. Negative controls were injected with recombinant EGFP lacking a targeting ligand.

Identification of the DmYP1 Receptor Binding Region

A deletion analysis of the DmYP1 protein was conducted to identify the smaller region that efficiently transduced cargo into mosquito ovaries. Three portions of approximately 120 amino acids (FIG. 1) were encoded on an expression plasmid linked to EGFP via a Glycine-Serine linker. Fusion proteins included the DmYP1 secretion signal at the N-terminus. The construct was inserted into the plasmid pAc5-STABLE1-Neo under control of the *Drosophila Actin*5C promoter. Plasmids were transfected into *Drosophila* S2 cells using Lipofectamine® LTX WITH Plus™ Reagent (ThermoFisher). Cell culture supernatant was collected 72 hours post-transfection, concentrated 100× using Amicon® and Centricon® Plus-70 centrifugal filter devices (Millipore) and injected into female *An. gambiae* 12 and 24 hours PBF. Ovaries were dissected 12, 24 and 48 h hours post-injection, dissected and visualized for EGFP fluorescence. EGFP fusion protein fused to the full length DmYP1 protein (439 amino acids) was used as a positive control, while recombinant EGFP without a targeting ligand was used as a negative control.

Fusion Cas9 Protein Expression and Purification

The DmYP1 fragment P2C and EGFP were cloned as a Cas9 fusion into the plasmid pET28a-Cas9-cys (Addgene #53261) to create the constructs pET28a-P2C-Cas9 and pET28a-P2C-EGFP-Cas9. Plasmids were transformed into *E. coli* BL21 (NEB) and Rosetta2™ (DE3) pLysS competent cells Novagen (Millipore Sigma) and transformation verified by PCR. To induce expression of recombinant protein, a preculture was grown overnight at 37° C. in 50 ml of LB medium supplemented with chloramphenicol and/or kanamycin (34 ug/ul; 100 ug/ul). After 12 hours, 10 ml of preculture was transferred to 990 ml of LB supplemented with the same antibiotics, incubated at 37° C. until OD=0.6, when 0.05 mM IPTG was added and the culture incubated overnight at 30° C.

Cells were spun down at >10,000×g for 15 min, resuspended in 50 ml lysis buffer (20 mM Tris-HCl pH 8.0, 300 mM NaCl, 20 mM imidazole), placed at −80° C. overnight and incubated with lysozyme (1 mg/ml) and 100 ppm of paramethylsulfoxide (PMSF) for 30 min at 4° C. The suspension was sonicated 5 times at 60% duty 5 sec pulse 5 sec rest (two aliquots each 25 ml), centrifuged at 13,000×g for 30 min, the supernatant removed and incubated with Ni-NTA beads with rotation at 4° C. overnight. Beads were washed 3 times with 10 ml lysis buffer and eluted with 1 ml elution buffer (20 mM Tris-HCl pH 8.0, 300 mM NaCl, 250 mM imidazole) 10 times. Eluted protein was dialyzed in a Slide-A-Lyzer dialysis cassette (Thermo Fisher) for two hours in dialysis buffer (50 mM Tris-HCl pH 8.0, 300 mM KCl, 0.1 mM EDTA, 0.5 mM PMSF) and buffer changed every 2 hours 2 times, then left overnight at 4° C. with gentle agitation in fresh buffer. Protein purity was visualized by SDS-PAGE and concentration estimated using Bradford assay.

In Vitro DNA Cleavage Assays

Cas9 fusion proteins and sgRNAs were mixed at a molar ratio of 1:2 and used to test in vitro cleavage activity of a PCR fragment spanning the *Ae. aegypti* kmo-460 and kmo-519* target sites following the PNA BIO suggested protocol (pnabio.com). Reactions were performed for 1 h at 37° C. and diagnostic bands visualized by electrophoresis in a 1% agarose/TAE gel.

Embryonic Microinjections

Embryo microinjection mixes contained Cas9 and Cas9 fusion proteins generated in our lab at 300 ng/μL, and 100 ng/μL sgRNA against kmo-460. sgRNA was prepared according to the protocol described in Kistler et al. 2015 (herein incorporated by reference in its entirety) using CRISPR_R: 5'AAA-AGC-ACC-GAC-TCG-GTG-CCA-CTT-TTT-CAA-GTT-GAT-AAC-GGA-CTA-GCC-TTA-TTT-TAA-CTT-GCT-ATT-TCT-AGC-TCT-AAA-AC-3' (SEQ ID NO: 34). Briefly, template for in vitro transcription was generated by amplification of the CRISPR_R and target specific CRISPR F in 4-8 PCR reactions using Phusion (New England Biolabs). The resulting oligos were pooled from all reactions and purified using Cycle Pure kits (Biotek). A microgram of PCR product was used in the T7 Megascript kit (Ambion) following the manufacturer's protocol to generate single stranded sgRNA, which was purified using the Megaclear column purification kit following the manufacturers' protocol. sgRNA concentration was measured using a Nanodrop ND-1000, aliquoted at 2 μg/μL and stored at −80 C.

Protein and the sgRNAs were mixed and incubated at room temperature for 10 minutes before injection into *Aedes* eggs (using an Eppendorf FemtoJet microinjector with InjectMan manipulator on a vibration isolation table) 90-120 minutes post-oviposition as described in Jasinskiene et al., 1998 (herein incorporated by reference in its entirety). After injection, eggs were placed on wet paper filter for four days before hatching. Hatched first-instar $G_0$ larvae were screened for white or mosaic eyes, which were initially pooled to create a white eye colony. Individuals from this colony were later outcrossed to create an isoallelic white eye line homozygous for a single kmo-460 mutation (Wh-Iso8-kmo$^{460}$).

Immunofluorescence Assays

For immunofluorescence assays, dissected mosquito ovaries were fixed with 4% paraformaldehyde for 20 minutes at room temperature (RT). To block non-specific binding ovaries were incubated for two hours at RT with 3% bovine serum albumen (BSA) in phosphate buffered saline (PBS) with 0.1% Tween 20. Following blocking, Cas9 protein was detected using rabbit anti-Cas9 polyclonal antibody (Abcam ab204448). Primary antibody was diluted 1:500 in PBS with 0.1% Tween 20 and incubated for one hour at RT or overnight at 4° C. After incubation, samples were washed three times with 0.1% Tween 20 in PBS, and the primary antibody labeled with 1:500 anti-rabbit Alexa Fluor 594 secondary antibody (Abcam ab150076). After three additional washes, ovaries were air-dried and slide mounted with ProLong Gold Antifade Reagent (Molecular Probes) and visualized using epifluorescent microscopy.

Detection of Cas9-Mediated Editing

After mating as described in the above, females (generation −1; $G_{-1}$) were blood fed and injected with P2C-Cas9 RNPs and EERs. Resulting $G_0$ offspring were screened for kmo gene editing phenotypes (white or mosaic eyes). Genomic DNA from identified individuals was extracted using DNeasy blood and tissue kits (Qiagen) and the region spanning both kmo 460 and 519* sites amplified by PCR using primers ZA2210 (5'TTC-AAG-ACC-AGG-CCT-CAA-TC3') (SEQ ID NO: 35) and KmR1 (5'TCA-CTA-AAC-TCA-GCC-AGT-ATC-CTA-T3') (SEQ ID NO: 36) and cloned into the pJET1.2 vector. A minimum of 6 clones per individual were randomly selected and sequenced.

Results

Figure 3:
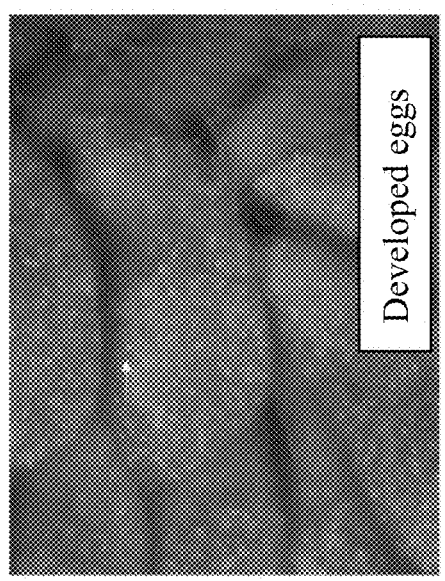
FIG. 3 shows P2C-mediated transduction of EGFP was observed in yolk granules (arrows) throughout embryo development.
Figure 3:
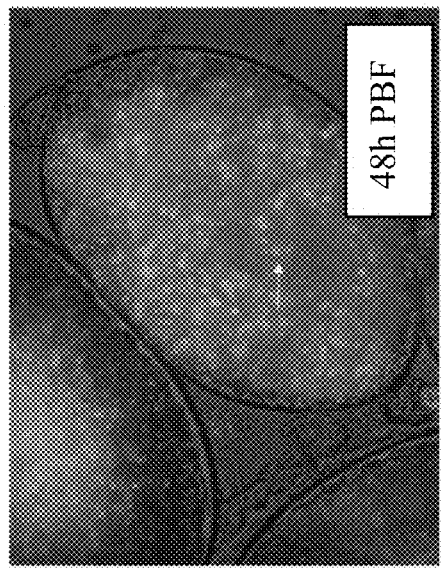
Figure 3:
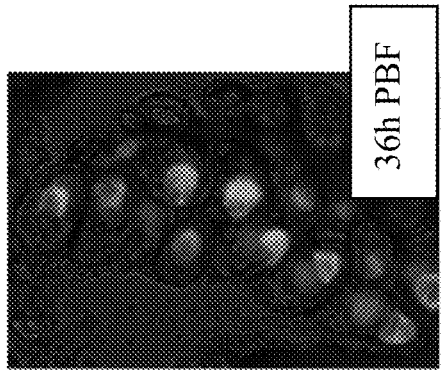

Recombinant EGFP lacking a targeting ligand was injected as a negative control. Ovaries dissected at 24, 36, 48, 60 and 72 h PBF were examined for visible EGFP fluorescence. EGFP was visualized in 90-100% of primary oocytes regardless of the timing of the injection (Table 1) and at all stages of oocyte development including in fully developed eggs ready to be oviposited (FIG. 3).

For easier downstream construct design and expression, deletion analysis identified a smaller region of the protein required for ovary uptake. Fragments containing the 120 amino acid N-terminal portion of the protein ("P2") could be taken up into ovaries (FIG. 1). Further deletion analysis of the P2 fragment identified that a 41 amino acid fragment, termed "P2C" (NLQQQRQHGKNGNQDYQDQSNEQRKNQRTSSEEDYSEEVKN, SEQ ID NO: 3) was fully sufficient to deliver EGFP to Anopheles oocytes (FIG. 1).

Figure 4A:
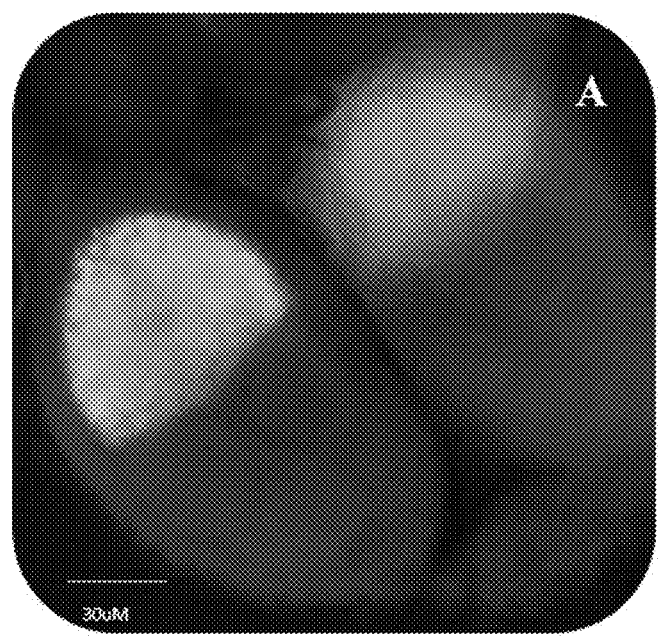
FIG. 4A shows localization of EGFP by P2C fusion in developing *Ae. aegypti* oocytes following injection in adult blood-fed females (positive control).
Figure 4B:
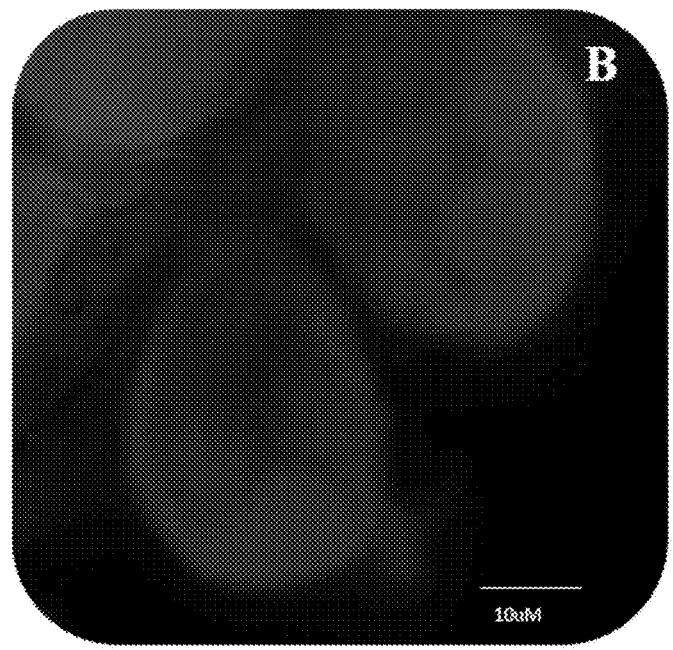
FIG. 4B shows lack of signal when Cas9 was localized lacking a targeting ligand (negative control).
Figure 4C:
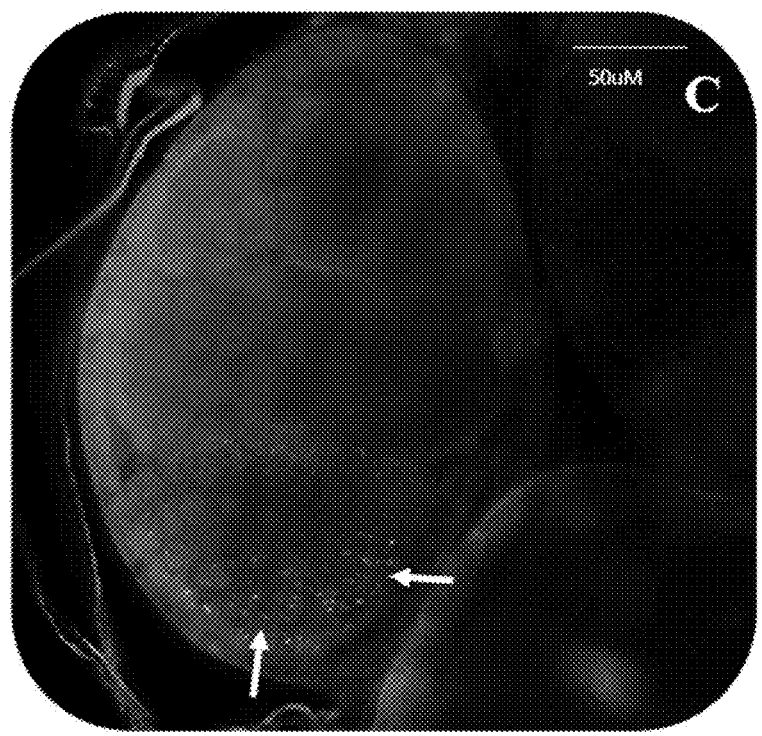
FIG. 4C shows the localization of P2C-Cas9 fusion protein (arrows).
Figure 4D:
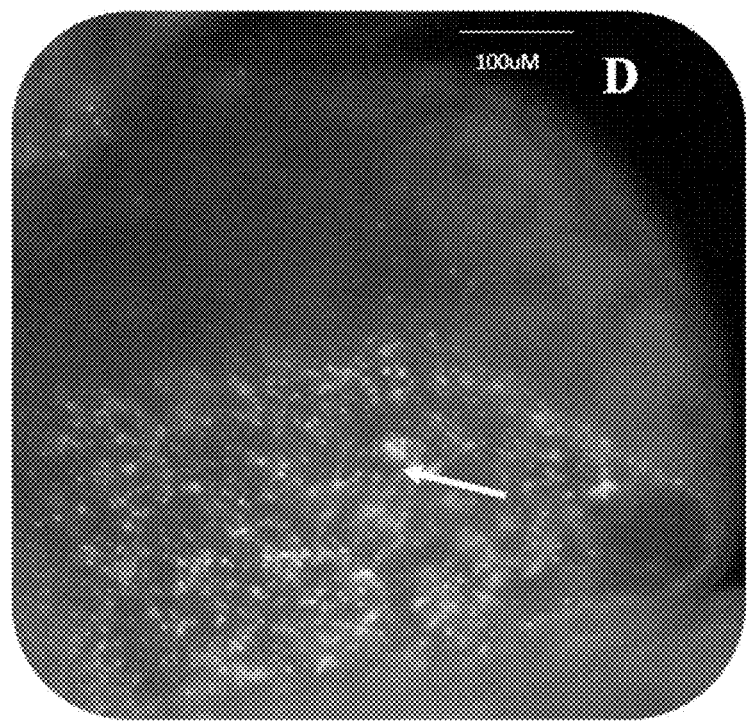
FIG. 4D shows the localization of CAS9-P2C-EGFP (arrows). Arrows indicate foci of fluorescence. All images were taken 24 hours post-injection.
Figure 5:
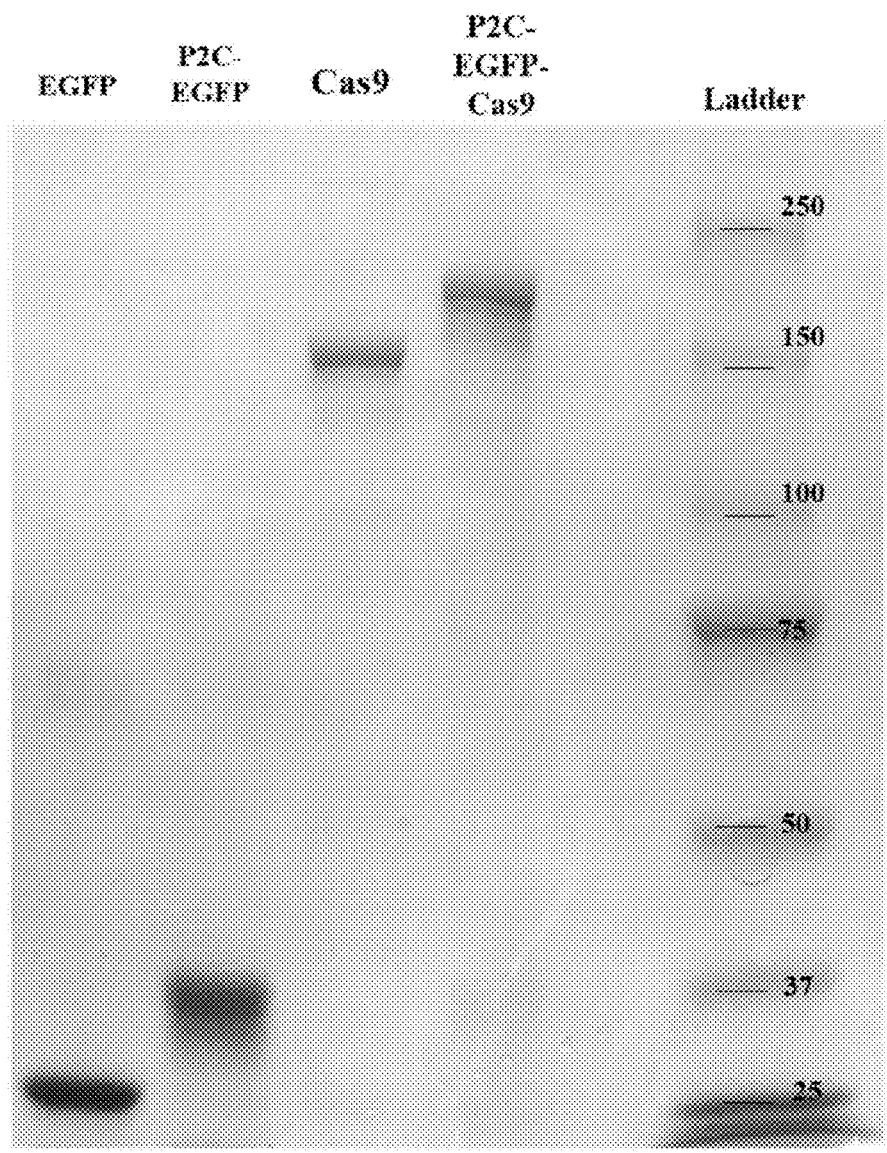
FIG. 5 shows the verification of *E. coli* expression and activity for recombinant proteins by Coomassie-stained gel of *E. coli*-expressed EGFP, P2C-EGFP, Cas9 and P2C-EGFP-Cas9.
Figure 6:
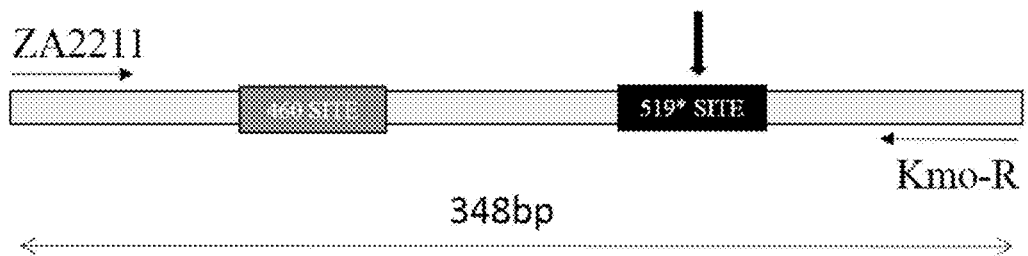
FIG. 6 shows the schematic showing cut site for in vitro Cas9 cleavage assays.

After validating the utility of P2C to target material to An. gambiae oocytes, the Zika virus vector mosquito Ae. Aegypti was also tested, since efficient gene-editing tools have already been established in this species that could serve as positive controls for our analysis. As a preliminary test, P2C-EGFP was injected into Ae. aegypti following a blood meal. EGFP fluorescence was seen in 100% of primary follicles (FIG. 4A), an uptake efficiency comparable to analogous tests in An. gambiae females. P2C was then expressed and purified as fusion protein with Cas9 (P2C-Cas9 and P2C-EGFP-Cas9). After injection in vitellogenic females, Cas9 or EGFP-Cas9 was detected by fluorescence/immunofluorescence in the developing oocytes (FIGS. 4B-D).

In Vivo Activity of P2C-Cas9 and P2C-EGFP-Cas9 and Generation of an Isoallelic White-Eye Line of Ae. Aegypti To test whether the P2C ligand affected the function of Cas9 in vivo, fusion proteins P2C-Cas9 and Cas9-P2C-EGFP and unmodified Cas9 (control) were used to target the Ae. aegypti kynurenine monooxygenase (kmo) gene using sgRNA460 by standard embryonic microinjection. Fusion proteins were active in embryos and generated mutations at the kmo-460 site in 2-9.6% of injected embryos (4-45% of hatched larvae, Table 2). Resulting larval phenotypes included mosaic and white-eyed individuals (FIGS. 9A-E) that were pooled to generate a multiallelic colony of white-eye mosquitoes with mutations at the 460 site (Table 2). One individual female was used to find an isoallelic line)(Wh-Iso8-kmo$^{460}$) with a characterized kmo site 460 deletion (del-5'GGTGATCATT3') (SEQ ID NO: 37).

Gene Knockout in the Maternal Germline

Figure 7:
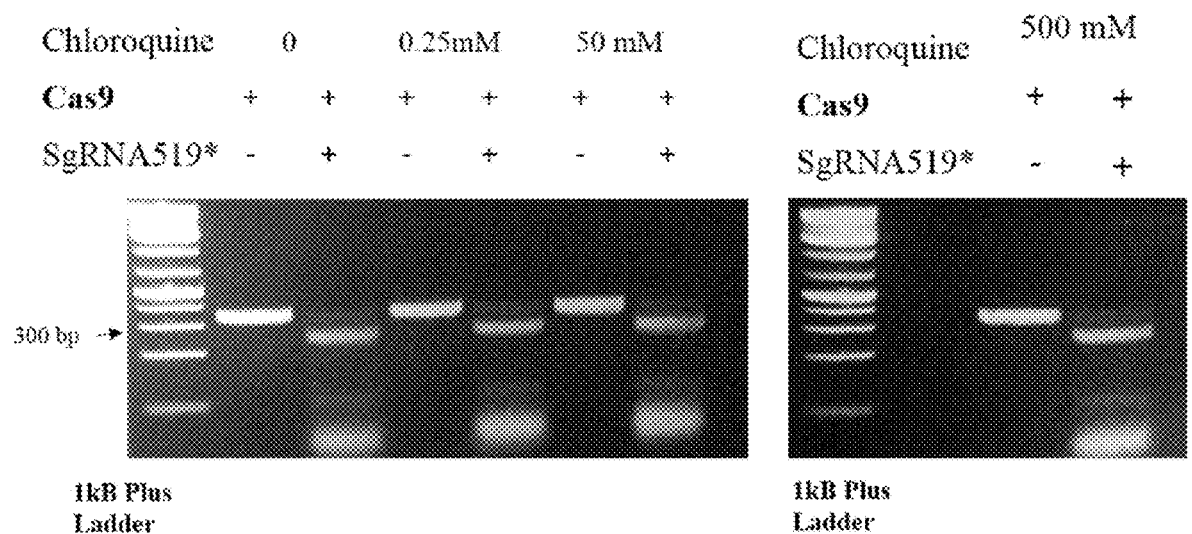
FIG. 7 shows the cleavage activity of recombinant Cas9 is not inhibited by chloroquine by gel separation.
Figure 8:
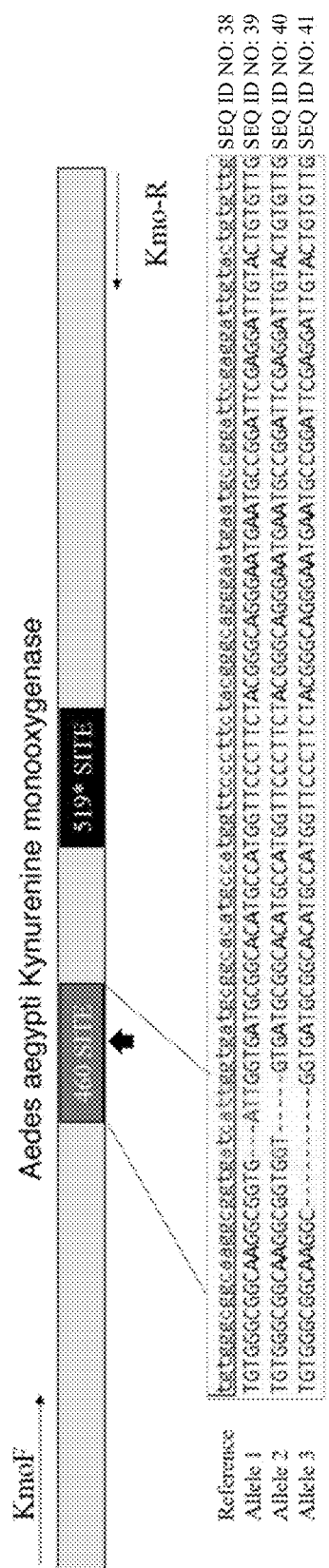
FIG. 8 shows the schematic for generation of white eye kmo-460 deletion *Aedes aegypti* colony and examples of obtained genotypes (SEQ ID NOs: 38-41).
Figure 9A:
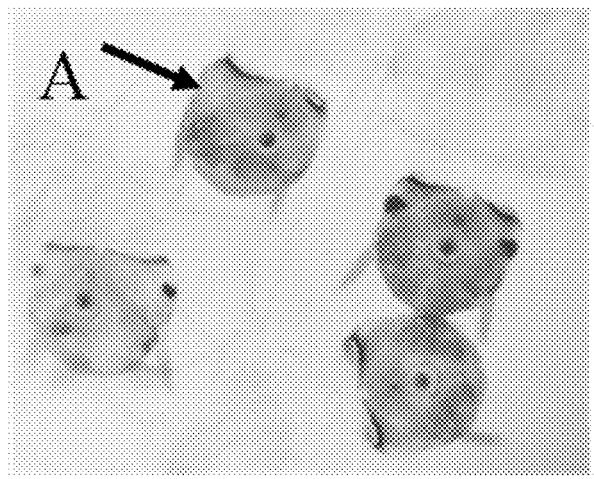
FIG. 9A-E shows phenotypes obtained by microinjection of Cas9 and Cas9 fusion proteins with sgRNA460 into *Ae. aegypti* embryos.
Figure 9B:
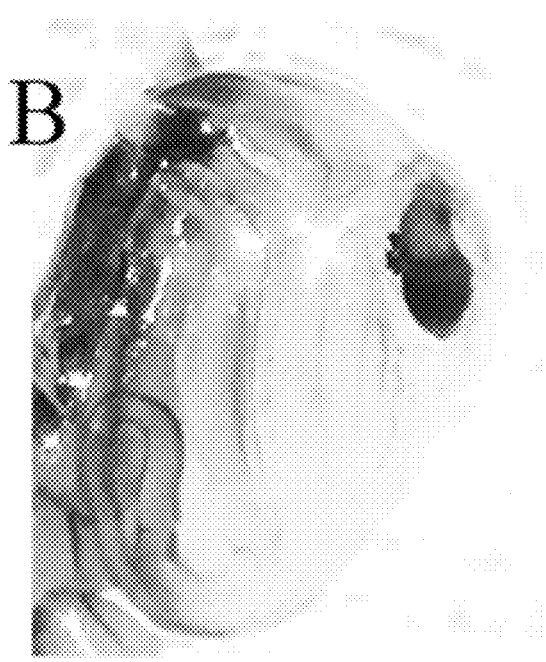
Figure 9C:
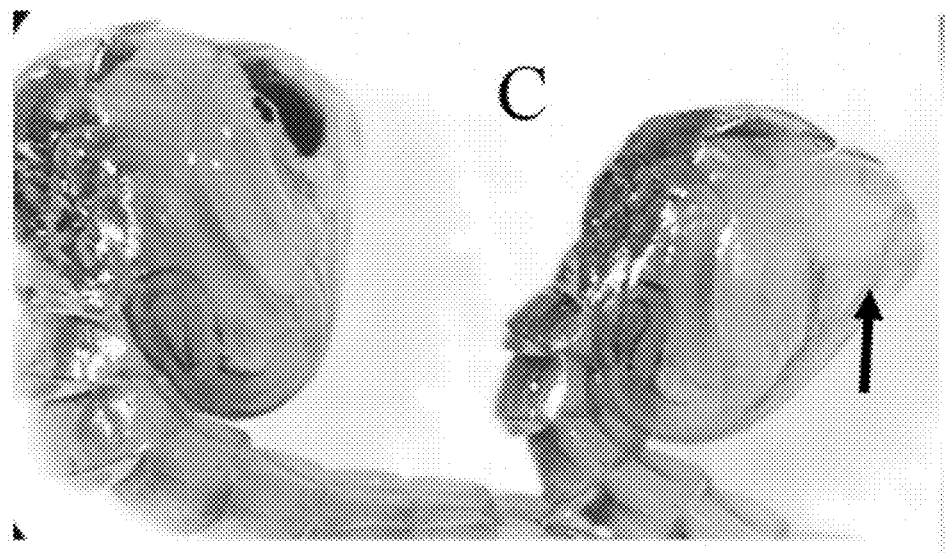
Figure 9D:
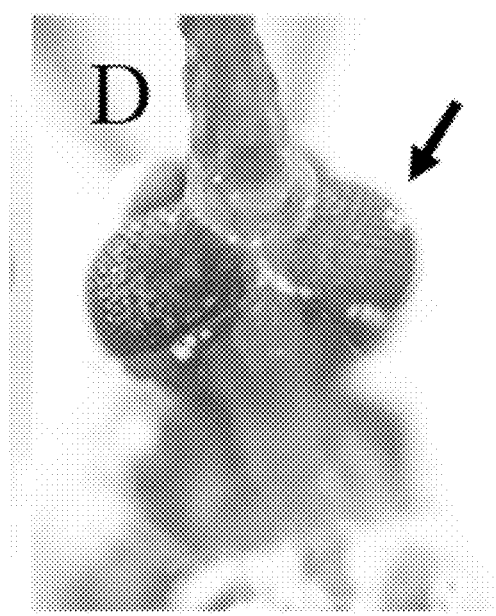
Figure 9E:
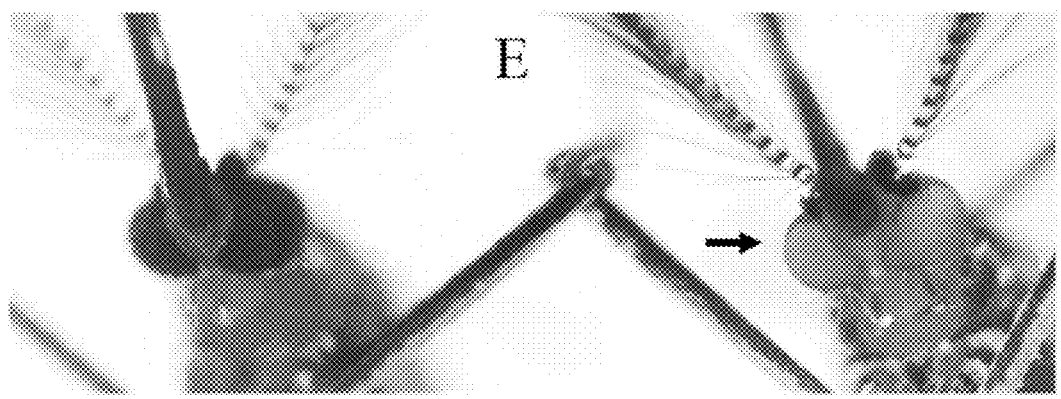

To test for editing of the oocyte chromosomal sequence, wild-type females outcrossed to white eye males (Wh-Iso8-kmo$^{460}$ in most cases; the multi-allelic white eye line was used for early experiments) with Cas9 RNP using the sgRNA targeting the kmo 519* site. In the absence of editing, all offspring from this cross would have black eyes, but if editing of the maternal germline was successful, the cross would result in white eye offspring. We observed a focal pattern of EGFP and Cas9 fluorescence in ovaries following injection suggesting that cargo (molecule of interest) was not released from the endosomes but rather was delivered to the yolk granules (FIGS. 1 and 4B-D), and the body of literature surrounding drug delivery efforts supports the confinement of cargo to endosomes following RME. We therefore sought to explore whether endosomal release reagents (EERs) characterized in these drug studies would promote editing of the germline DNA by mediating the release of the P2C-EGFP-Cas9 from endosomes. The effect of dynasore, ammonium chloride, chloroquine, saponin and monensin on efficiency in adult females was tested with the same crossing scheme. Each compound identified was injected using the $LD_{50}$ concentration as a starting point for injections (Table 3). Chloroquine also did not affect Cas9 cleavage function in vitro (FIG. 7).

In optimizing the compositions and method, a total of 34 trials were performed, injecting females at different time points post blood feed, different concentrations of P2C-EGFP-Cas9 and sgRNA519*, and different concentrations and types of EERs (Table 4). White eye offspring were produced with P2C-EGFP-Cas9 concentrations between 2200 ng/ul to 6400 ng/ul of protein, sgRNA higher than 1000 ng/ul, injecting females ≥24 hours post blood meal, and the EER chloroquine at a concentration between 0.5 mM-2 mM (Table 4). These conditions also resulted in eight out of twelve trials producing gene editing events (Table 4, Table 5), resulting in eight white-eye $G_0$ and three mosaic $G_0$ (most individuals documented in FIG. 10B). The efficiency was calculated for the maternal chromosome gene editing as the percentage of knock-out $G_0$ out of the number of injected females ($G_{-1}$) that laid eggs (when females were allowed to oviposit individually) or as percentage of knock-out $G_0$ out of the number of females injected (when females were pooled for oviposition) in order to compare editing efficiencies to embryo injections. In the 8 successful trials, knock-out efficiency ranged from 3% to 27% (Table 5). Interestingly, we found that females injected at 30 hours post blood meal or earlier produced only white eye progeny, while females injected later at 54 hours post blood meal produced both mosaic and white eye progeny. This supports that the timing of injection after blood feeding plays a role in whether Cas9 nuclease activity occurs in the oocyte or in the embryo.

To verify editing events, the sequence flanking both target sites was amplified from the genomic DNA of white-eye and mosaic offspring, cloned and sequenced. Sequences from at least 6 clones per individual were obtained to confirm maternal vs. paternal gene deletion events. The sequences of the kmo gene of all white individuals showed site 460 and 519 indels on separate clones, confirming gene editing took place and indicating that the maternal chromosome was targeted. Sequencing clones derived from mosaic individuals detected multiple alleles at the 519 site including wild type (WT) sequences and indels at both sites on the same clone, indicating that the maternal and paternal chromosomes were targeted. Since the paternal chromosome is only exposed to the P2C-EGFP-Cas9 RNP following fertilization, these data indicate that the complex is functional for over 24 hours post blood meal and is active in the embryo.

Gene Knockout of Paternal Alleles

Figure 10A:
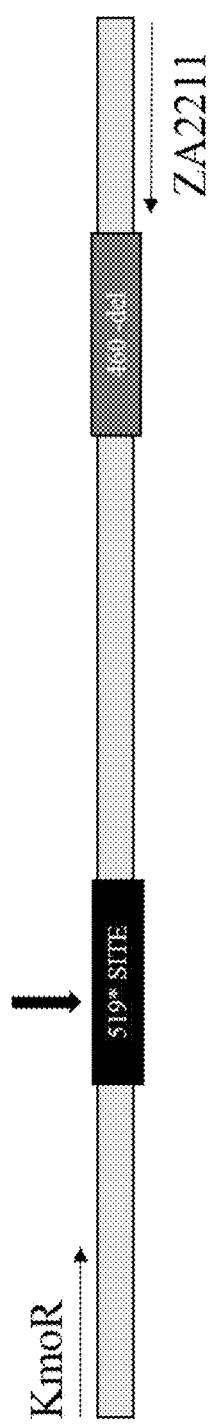
FIG. 10A shows the schematic for the target sites for sgRNAs.
Figure 10B:
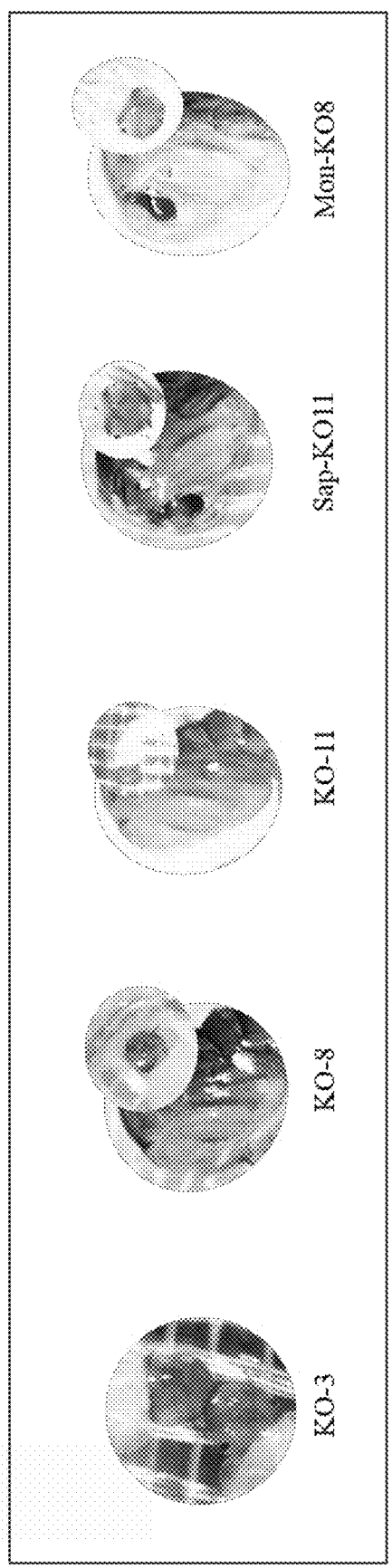
FIG. 10B shows phenotypes (larvae, pupae and/or adults) of obtained edited individuals.
Figure 10C:
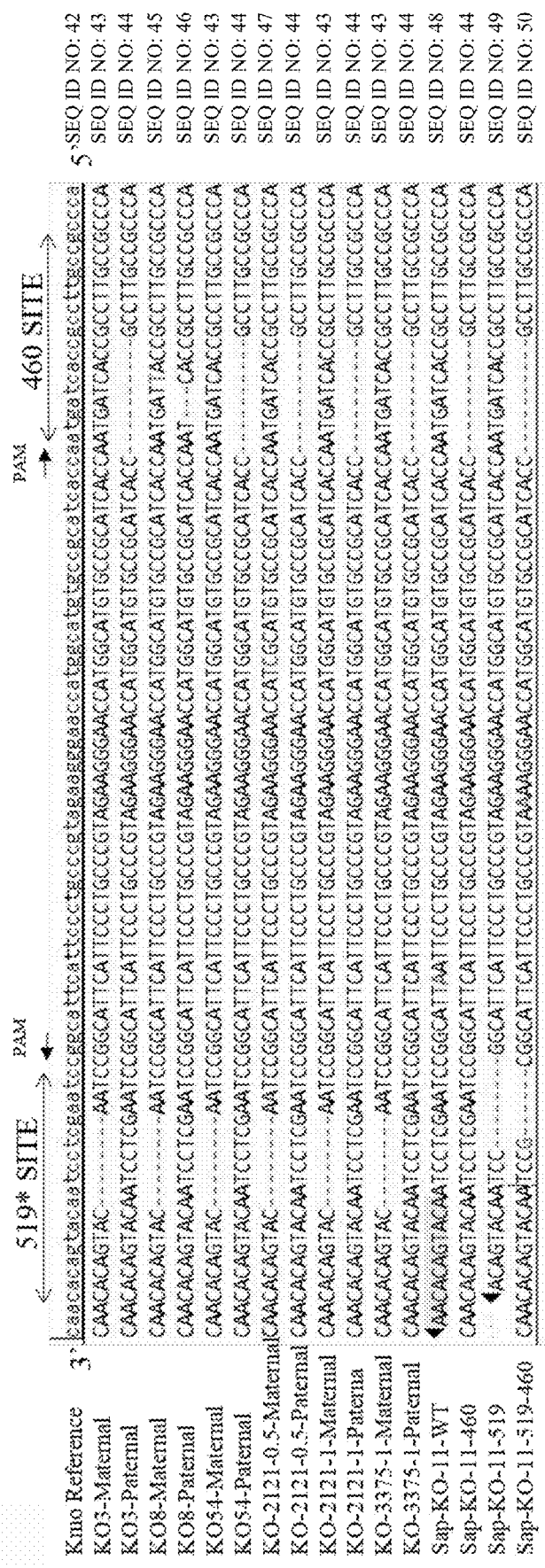
FIG. 10C shows examples of obtained maternal and paternal allele clone sequences of edited individuals (SEQ ID NOs: 42-50).

In order to estimate the frequency of paternal gene editing, homozygous Wh-Iso8-kmo$^{460}$ females outcrossed to homozygous wild type males were injected at 48-52 h PBF. Twelve trials were carried out with several EERs and concentrations of RNP and detected no altered offspring from treatments with dynasore, chloroquine or ammonium chloride. One mosaic offspring was observed in the saponin treatment (1/20 females=5%) and one mosaic offspring from the monensin treatment (1/20 females=5%) (Table 6). The region spanning the target sites from the mosaic individual collected from saponin treatment was cloned and sequenced (FIG. 10A). Deletions at both 460 and 519* sites were detected on the same clone, suggesting post-zygotic paternal gene editing. The genomic DNA from the monensin and spontaneous white eye individuals were not of suitable quality for PCR and cloning.

Gene Knockout in Wild Type Mosquitoes

An experiment was conducted to validate Cas9-mediated editing in wild-type Ae. aegypti. Wild-type intercrossed females were injected at 54 h PBF with the optimal concentrations of reagents determined in previous experiments and pooled for oviposition. 1413 larvae were screened and one mosaic $G_0$ individual was found (out of 40 ovipositing $G_{-1}$ females=2.5%). This individual died as a pupa. Remaining $G_0$ wild-type males and females were pooled by sex, outcrossed to Wh-Iso8-kmo$^{460}$ adults of the appropriate sex, and $G_0$ progeny from each outcross was screened for white eyes. Nine white eye larvae were found exclusively on the progeny from $G_0$ males×Wh-Iso8-kmo$^{460}$ females (Table 6).

Heritability of the Kmo Mutations

A sample of $G_0$ individuals showing white eyes (1 male and 2 females from outcrossed, injected wild-type female $G_{-1}$) and mosaic (1 male and 1 female from outcrossed, injected white-eye $G_{-1}$ female) phenotypes were outcrossed to homozygous Wh-Iso8-kmo$^{460}$ mosquitoes and the progeny screened for white eyes. Surprisingly, it was observed that 100% of the progeny resulting from white eye $G_0$ females had white eyes. Sequencing of kmo PCR fragments showed both the paternal 460 site mutation and the maternal site 519 mutation in $G_0$ and $G_1$ individuals with white eye-phenotype. On the other hand, heritable gene-editing in the $G_0$ offspring from the two mosaics was not confirmed since ~50% had white-eyes, consistent with what we would expect from crossing a heterozygous $G_1$ with white-eye mosquitoes.

CONCLUSION

A novel method for the delivery of cargo, such as gene editing compounds, that circumvents the need for embryo injections has been developed. This delivery has potential for broad application of Cas9-mediated gene editing technology, having particular utility for systems/animal species recalcitrant to traditional embryonic microinjection techniques. By exploiting the endogenous YPP uptake pathway that is conserved across species of oviparous animals, we have targeted cargo to the oocytes of both An. gambiae and Ae. aegypti. A 41 amino acid peptide (P2C) derived from DmYP1 was sufficient to mediate Cas9 uptake into the ovaries and when coupled with an appropriate EER, the Cas9 RNP specifically targeted the kmo gene in a manner that is both heritable, and flexible in terms of timing and efficient. Targeting peptides derived from yolk protein precursor proteins which have utility to more efficiently gene edit commercially meaningful species, including chickens, turkeys, salmon, tilapia, and trout, also exist and can be isolated for this purpose in diverse species.

The phenotypes we observed following injection of the P2C-EGFP-Cas9/sgRNA RNP likely reflect the developmental timing of the mosquito oocyte and the embryo, suggesting that accessibility of the chromosomal DNA to the RNP in the oocyte changes during development of the ovaries. That paternal copies of the gene are mutated suggests that the complex is stable and active following fertilization, which is more than 24 hours after injection. Earlier injections (~24 hrs PBF) produced maternal chromosome editing events at high efficiency, while mosaic $G_0$s were observed from later injections PBF, indicating editing events in some somatic cells, and confirming that the RNP complex is active in the fertilized embryo. Application of the targeting ligands to other species will use system-specific timing to optimize efficiency.

Although the targeting ligands were validated in mosquitoes, the technique can be conceptually extended to any animal species that undergoes vitellogenesis (most invertebrates and non-mammalian vertebrates). The P2C ligand will likely work generally in dipterans, as YP receptors from D. melanogaster have been shown to uptake YPPs from 13 other Drosophila species and five non-drosophilid dipterans. DmYPs also share sequence homology with two minor YPPs of lepidopterans, the egg-specific protein and the follicular epithelium yolk protein. In non-mammalian vertebrates, oogenesis occurs in an analogous manner to arthropods; the major yolk proteins vitellogenins (Vgs) are synthesized in the liver, secreted into the bloodstream, and are taken up into the developing eggs by RME, and could be exploited for species-specific targeting ligand development. Oogenesis in eutherian mammals, however, occurs in a qualitatively different manner compared to the lower vertebrates. Vgs and other yolk proteins have been evolutionarily lost. Instead, the mammals have evolved the placenta, an organ that acts as a connection between the mother and the offspring, providing nutrients for the developing embryo. However, even in mammals, RME is used to deliver hormones and other signaling molecules to the developing embryo, suggesting that targeting ligands could potentially be adapted for use in mammals.

Compared to embryo injection, gene editing was efficient and technically much easier to accomplish (Table 5). The requirements for the target ligands are substantially lower compared to embryonic microinjection where the microinjection apparatus costs tens of thousands of dollars and requires extensive training to use. In contrast, the equipment for target ligand conjugation and injection costs approximately 2 dollars, and the technique can be learned in less than an hour. While higher concentrations of Cas9 protein and sgRNAs are required in the injections mixes, the cost to produce these reagents is substantially lower than traditional microinjection equipment. Along with the financial improvements, the ease of adult injections makes this method a substantial improvement over existing embryo-injection techniques, putting gene editing capability into the reach of non-specialist laboratories and non-model systems and potentially revolutionizing the broad application of functional organismal genetics.

Example 2

Figure 11:
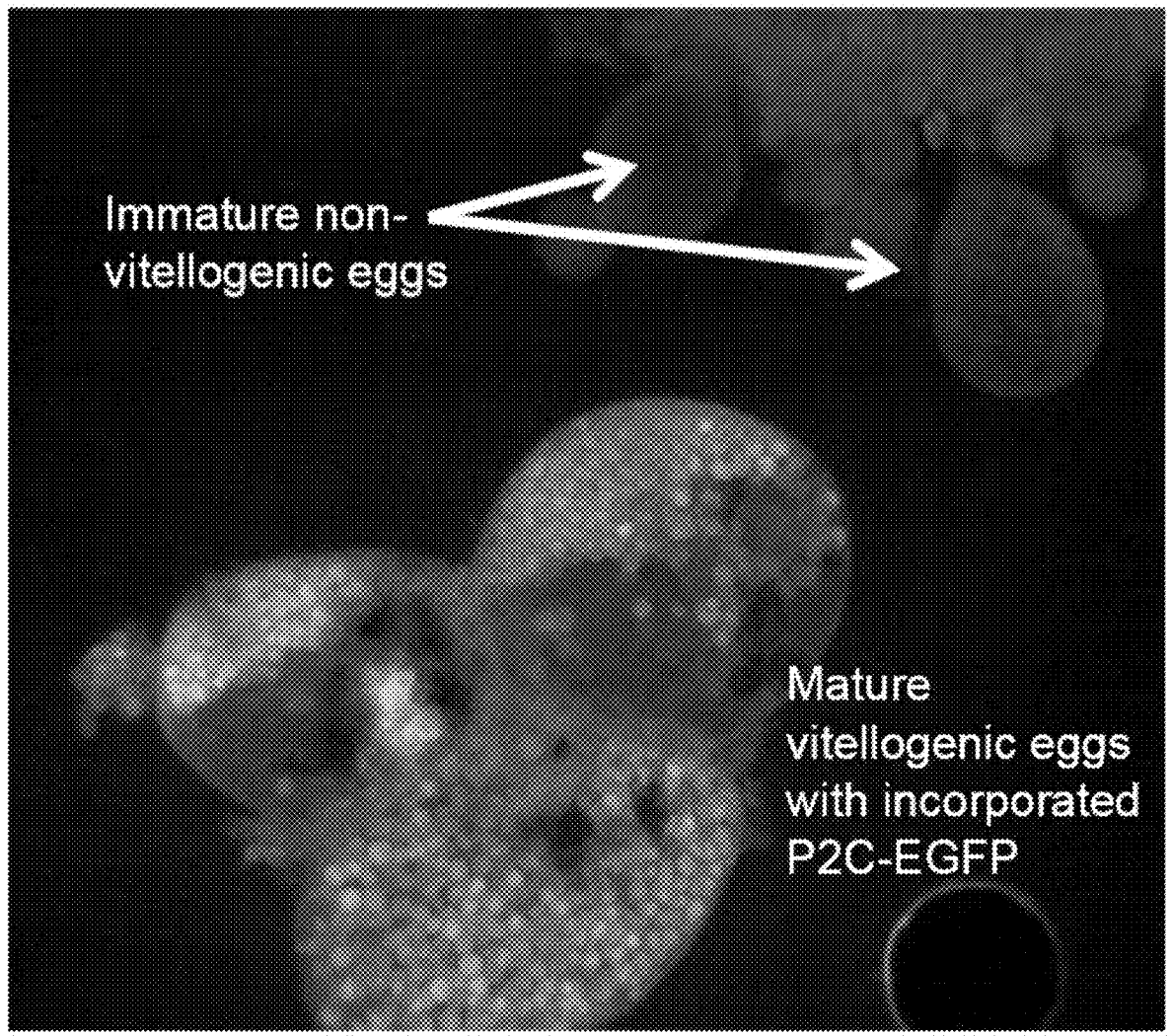
FIG. 11 shows dissected mealybug ovaries with P2C-EGFP visible in only the developing vitellogenic eggs.
Figure 12:
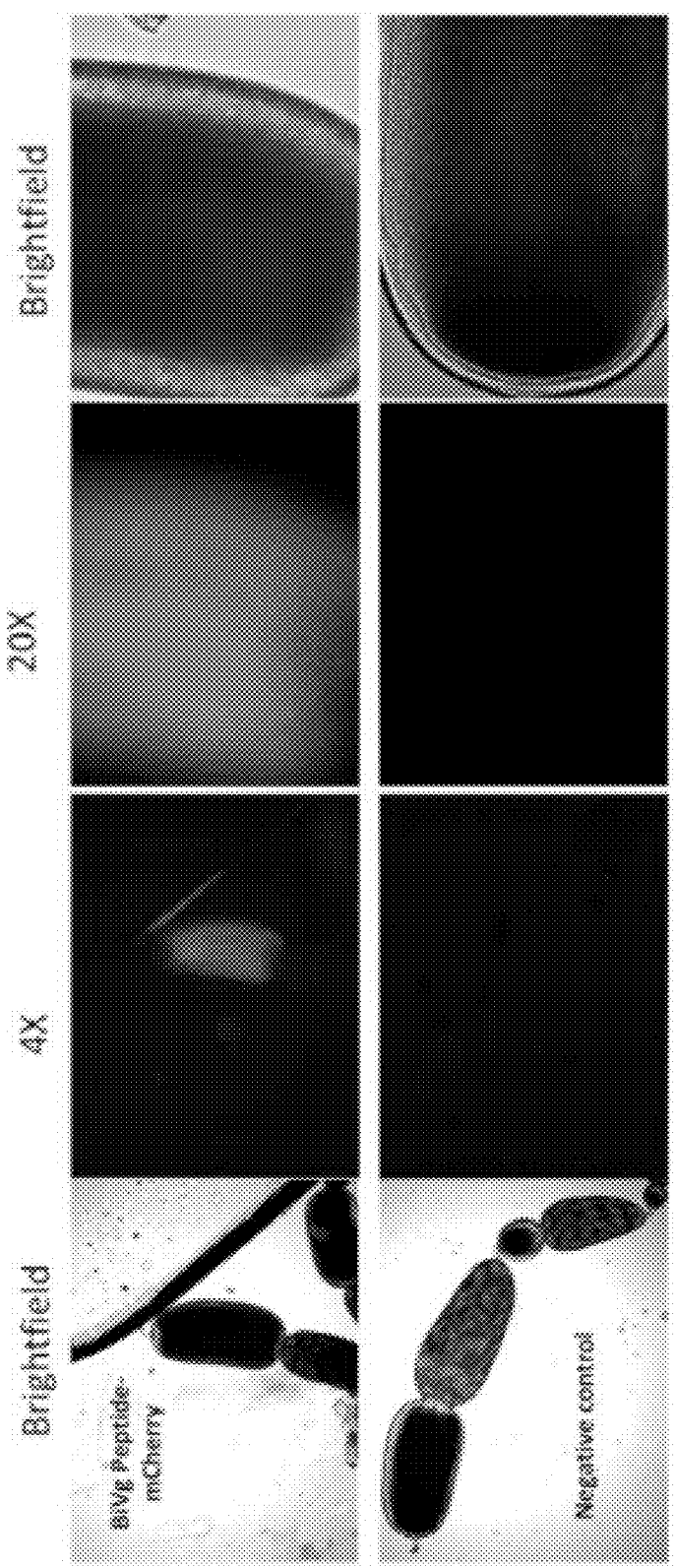
FIG. 12 shows the transduction of mCherry protein in *Bombus impatiens* ovaries using targeting peptide RKSKNFDK (SEQ ID NO: 27) (See GenBank accession no. XP_003492277.1). mCherry is transduced into developing vitellogenic eggs after injection into adult females.
Figure 13:
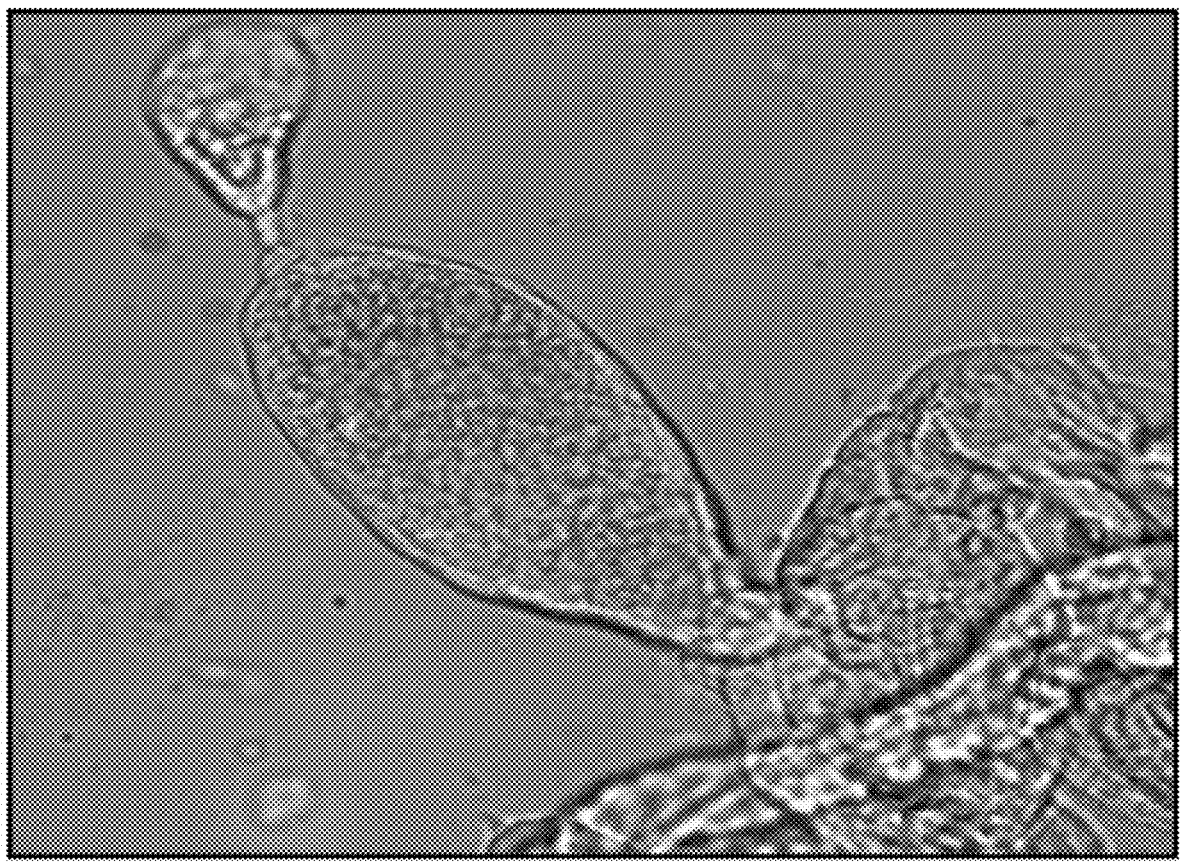
FIG. 13 shows the transduction of mCherry protein in *Bemisia tabaci* ovaries using targeting peptide DIVKTTNY (SEQ ID NO:26) (See GenBank accession no. ANF29558.2). mCherry is transduced into developing vitellogenic eggs after injection into adult females.
Figure 14:
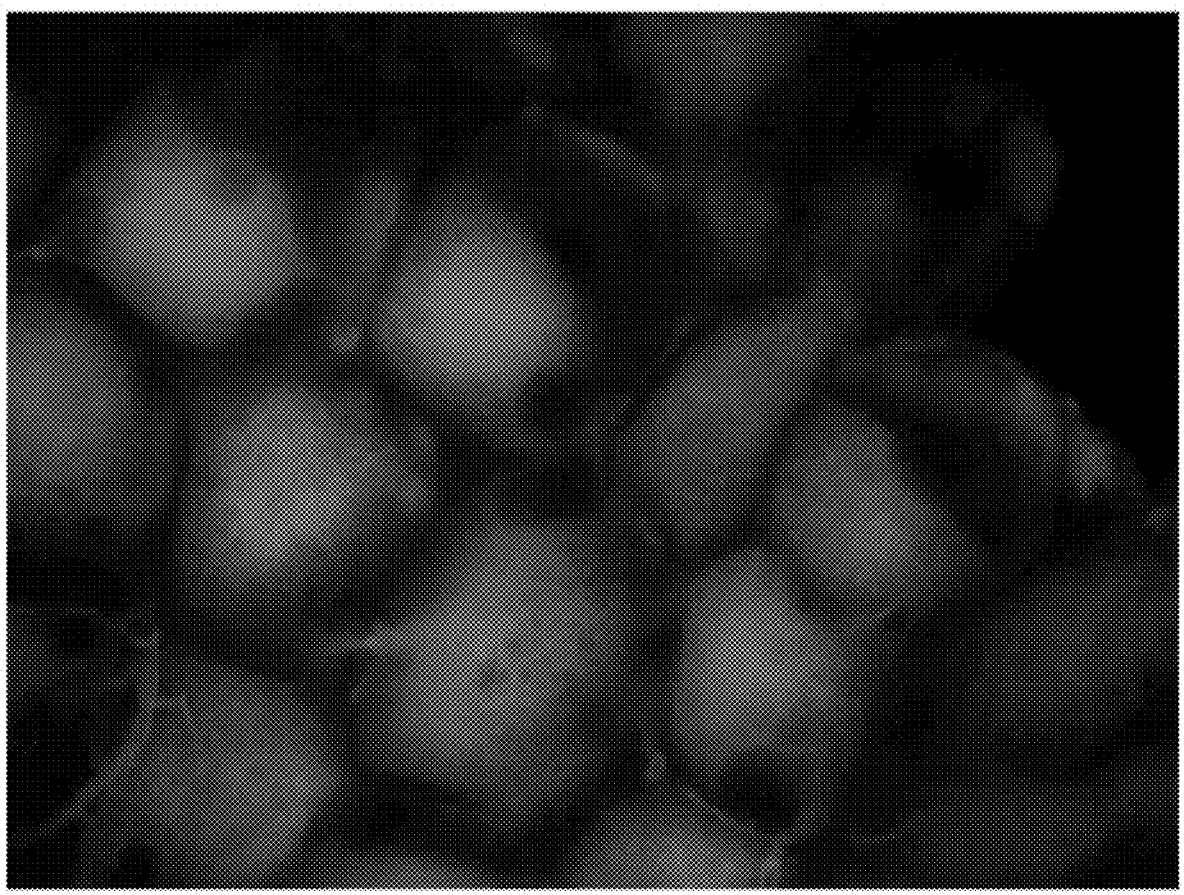
FIG. 14 shows the transduction of mCherry protein in *Aedes aegypti* ovaries using targeting peptide QVTKTQNF (SEQ ID NO: 4) (See GenBank accession no. AAA99486.1). mCherry is transduced into developing vitellogenic eggs after injection into adult females.
Figure 15:
FIG. 15 shows the transduction of mCherry protein in *Ixodes scapularis* ovaries using targeting peptide NFTKTKNY (SEQ ID NO: 28) (See GenBank accession no. EEC14774.1). mCherry is transduced into developing vitellogenic eggs after injection into adult females.
Figure 16:
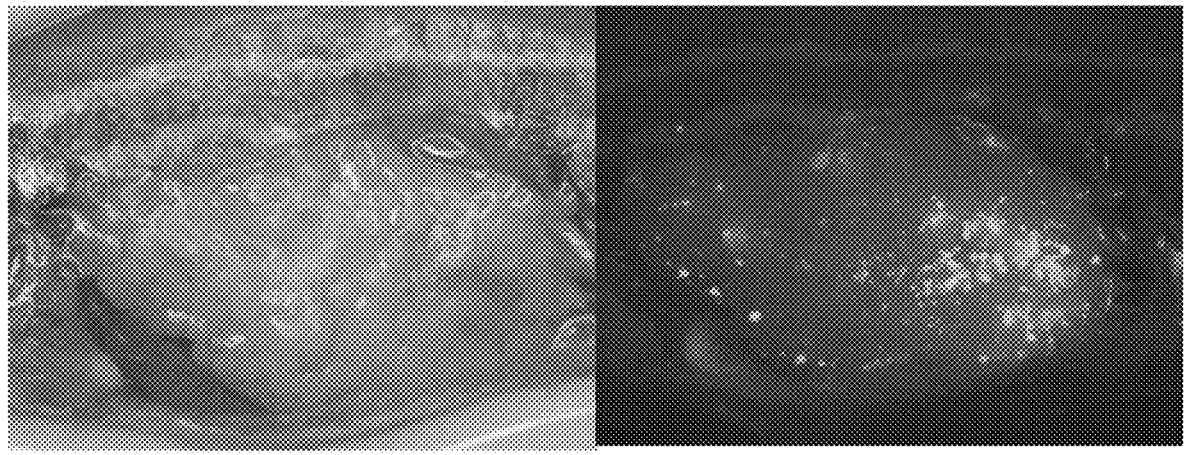
FIG. 16 shows the brightfield and fluorescence of the transduction of EGFP protein into *Danio rerio* ovaries using targeting peptide IVTKSKDL (SEQ ID NO: 29) (See GenBank accession no. AAK94945.1). EGFP is transduced into developing vitellogenic eggs after injection into adult females.

To determine if P2C could be used in to deliver cargo in species other than mosquito, it was tested on mealybugs using the procedure of Example 1. As shown in FIG. 11, P2C was able to specifically deliver EGFP into the developing vitellogenic eggs, but not the immature eggs. Therefore, P2C is an effective targeting molecule in more than just mosquitoes.

Example 3

To further determine ovary targeting ligands that may deliver cargo in other species, the conserved functional domain of vitellogenin was identified and screened in a wide variety of organisms, including both invertebrates and vertebrates.

The conserved region of vitellogenin genes was determined by Li et al. (*Receptor-Ligand Interaction between Vitellogenin Receptor (VtgR) and Vitellogenin (Vtg), Implications on Low Density Lipoprotein Receptor and Apolipoprotein B/E*, 2003, J Biol Chem, 278(5); 2799-2806, herein incorporated by reference in its entirety). The region on conservation encompasses amino acid positions 286-293 of the *Aedes aegypti* VgA1 vitellogenin gene. For example, the targeting ligand may be AVVKTKDL (lamprey, SEQ ID NO: 6), IITKSINF (nematode, SEQ ID NO: 7), RVVKTINY (cicada, SEQ ID NO: 8), EVVKTRNF (bean bug, SEQ ID NO: 9), DIVKTSNF (saw fly, SEQ ID NO: 10), DIVKTKNY (wasp, SEQ ID NO: 11), TIMKTHQF (cockroach, SEQ ID NO: 12), RIIKSTDF (frog, SEQ ID NO: 13), EVIKSKNY (weevil, SEQ ID NO: 14), EITKSKNY (oak silkmoth, SEQ ID NO: 15), EVTKSTNY (silkworm, SEQ ID NO: 16), IVTKSKDL (sturgeon, SEQ ID NO: 17), IVTKSKDL (zebrafish, SEQ ID NO: 18) TVTKSKDL (carp, SEQ ID NO: 19), EVTKSKNL (silkmoth, SEQ ID NO: 20), HLTKSKDL (trout, SEQ ID NO: 21), HLTKTKDL (tilapia, SEQ ID NO: 22), LLTKTRDL (killifish, SEQ ID NO: 23), LLTKTRDM (ricefish, SEQ ID NO:24), IVVKEKNH (prawn, SEQ ID NO: 25), DIVKTTNY (*Bemisia tabaci*, SEQ ID NO: 26), RKSKNFDK (*Bombus impatiens*, SEQ ID NO: 27), NFTKTKNY (*Ixodes scapularis*, SEQ ID NO: 28), or IVTKSKDL (*Danio rerio*, SEQ ID NO: 29).

Several targeting peptides, including DIVKTTNY (*Bemisia tabaci*, SEQ ID NO: 26), RKSKNFDK (*Bombus impatiens*, SEQ ID NO: 27), NFTKTKNY (*Ixodes scapularis*, SEQ ID NO: 28), or IVTKSKDL (*Danio rerio*, SEQ ID NO: 29), were further validated. The DNA encoding these peptides were synthesized, fused to the fluorescent reporter proteins GFP or mCherry (with a HIS tag to aid in purification), and cloned into pET28. The plasmids were then transformed into *E. coli* BL21 (NEB) and Rosetta2™ (DE3) pLysS competent cells, with the transformation being verified by PCT.

To induce expression of the recombinant protein, a pre-culture was grown overnight at 30° C. in 50 mL of Luria Broth (LB) supplemented with 50 µg/µl chloramphenicol and 100 µg/µl kanamycin. After 12 hours, 10 mL of preculture was transferred to 900 mL of LB supplemented with the same antibiotics, incubated at 37° C. until OD=0.6. Then 0.05 mM isopropyl β-D-1-thiogalactopyranoside (IPTG) was added and the culture incubated overnight at 30° C.

Cells were spun down at >10,000×g for 15 min, resuspended in 50 mL lysis buffer (20 mM Tris-HCl, pH 8.0, 300 mM NaCl, 20 mM imidazole), placed at −80° C. overnight and incubated with lysozyme (1 mg/ml) and 100 ppm of paramethylsulfoxide (PMSF) for 30 min at 4° C. The suspension was sonicated 5 times at 60% duty 5 seconds pulse 5 seconds rest (two aliquots each 20 mL), centrifuged at 13,000×g for 30 min, the supernatant removed and incubated with Ni-NTA beads (Qiagen) with rotation at 4° C. overnight. Beads were washed 3 times with 10 mL lysis buffer and eluted with 1 mL elution buffer (20 mM Tris-HCl, pH 8.0, 300 mM NaCl, 250 mM imidazole) 10 times. Eluted protein was dialyzed in a Slide-A-Lyzer dialysis cassette (Thermo Fisher) for two hours in dialysis buffer (50 mM Tris-HCl, pH 8.0, 300 mM KCl, 0.1 mM EDTA, 0.5 mM PMSF) and buffer changed every 2 hours, for 2 times, then left overnight at 4° C. with gentle agitation in fresh buffer, Protein purity was visualized by SDS-PAGE and concentration estimated using Bradford assay.

For arthropod injections, injections were performed with an aspirated tube assembly (A5177, Sigma) filed with a glass capillary needle. Bitellogenic adult females of each species were injected intra thoracically with the taxa-specific protein as described in Chaverra-Rodriguez et al. (herein incorporated by reference in its entirety) 24-50 hours post-injection, depending on the particular species, ovaries were dissected, mounted in saline buffer mixed with SlowFade Gold® antifade reagent (Invitrogen), covered with a coverslip and imaged on an Olympus BX41 epiflourescent microscope for GFP or mCherry. For zebrafish, purified protein was injected into the tail vein, and ovaries dissected and images for GFP 4-7 days post-injection.

As shown in FIGS. 12-16 by the presence of fluorescence inside the eggs, the transduction of both mCherry (arthropods) and EGFP (vertebrates) underwent RME. Therefore, using the 8 amino-acid taxa specific targeting molecule, it was possible to target and introduce into the cells a reporter or other cargo. Further, this region can easily be identified for any species of interest and the invention can be extended to any species that develops eggs by vitellogenesis, invertebrates and most vertebrates, except for eutherian mammals.

TABLE 1

Effects of time of injection on delivery efficiency. See FIG. 1.

| Time of injection (hours PBF)/ Replicate # | N Injected | N (showing EGFP in follicles) | N Observed | N Follicles | N Follicles with EGFP | % Follicles (Efficiency) |
|---|---|---|---|---|---|---|
| 12 h/1 | 20 | 17 | 5 | 243 | 243 | 100% |
| 12 h/2 | 20 | 19 | 8 | 383 | 381 | 98% |
| Total | 40 | 36 | 13 | 626 | 624 | 99.7% |
| 24 h/1 | 20 | 18 | 5 | 250 | 245 | 98% |
| 24 h/2 | 20 | 17 | 4 | 200 | 197 | 99% |
| Total | 40 | 35 | 9 | 450 | 442 | 98.2% |

TABLE 2

Validation of protein activity in vivo of different fusion P2C- Cas9/sgRNA460 RNP targeting the kmo gene in *Ae. aegypti*. GE = gene editing events. See FIGS. 4B-D.

| Protein | Protein (ng/ul) | sgRNA (ng/ul) | Eggs injected | $G_0$ larvae hatched | % hatching | $G_1$ Mosaic | $G_1$ white | % GE/injected eggs | % GE/hatched injected eggs |
|---|---|---|---|---|---|---|---|---|---|
| Cas9 | 300 | 100 | 48 | 23 | 48 | 1 | 0 | 2.1 | 4.3 |
| | | | 48 | 21 | 44 | 1 | 0 | 2.1 | 4.8 |
| | | | 73 | 23 | 32 | 7 | 0 | 9.6 | 30.4 |
| Cas9-P2C | 300 | 100 | 101 | 34 | 34 | 0 | 0 | 0.0 | 0.0 |
| | 300 | 200 | 74 | 21 | 28 | 0 | 0 | 0.0 | 0.0 |
| | | | 224 | 47 | 21 | 19 | 2 | 9.4 | 44.7 |
| Cas9-P2C-GFP | 300 | 250 | 137 | 53 | 39 | 0 | 0 | 0.0 | 0.0 |
| | 300 | 200 | 100 | 13 | 13 | 1 | 1 | 2.0 | 15.4 |
| Total | | | 805 | 235 | 32.4% | 29 | 3 | 3.1% | 12.5% |

TABLE 3

Related to Table 5. LD50 for different endosomal escape reagents (EER) injected into the hemolymph of *Ae. aegypti* females 24h PBF.

| Endosomal Escape Reagent | Females injected (N) | $LD_{50}$ (mM) |
|---|---|---|
| Chloroquine | 100 | 0.25 |
| Monensin | 100 | 1.0 |
| Saponin | 100 | 0.024 |
| Ammonium Chloride | 100 | 50 |

TABLE 4

Related to Table 5. Results from all maternal chromosome knockout trials in *Ae. aegypti* using P2C-EGFP-Cas9.

| [Protein] (ug/ul) | [sgRNA] | Endosomal escape strategy | $(G_{-1})$ ♀ injected | ♀ Laying eggs | Wild type | Knock-out (KO) | GE/injected female | GE/$G_{-1}$ female |
|---|---|---|---|---|---|---|---|---|
| 1237 | 1118.3 | None | 20 | 1 | 2 | 0 | 0% | 0% |
| 1250 | 1853 | None | 12 | 7 | 231 | 0 | 0% | 0% |
| | | Dynasore | 18 | 1 | 4 | 0 | 0% | 0% |
| | | None | 10 | 3 | 73 | 0 | 0% | 0% |
| | | Dynasore | 15 | 1 | 4 | 0 | 0% | 0% |
| 3337.5 | 1174 | None | 9 | 6 | 75 | 0 | 0% | 0% |
| | | Chl 0.25 mM | 15 | 6 | 72 | 0 | 0% | 0% |
| | | Chl 0.5 mM | 15 | 6 | 79 | 1 | 7% | 17% |
| | | Chl 1 mM | 15 | 4 | 46 | 0 | 0% | 0% |
| 3375 | 1342 | Chl 0.5 mM | 39 | 17 | 375 | 2 | 5% | 12% |
| 3375 | 703 | Chl 0.5 mM | 30 | 17 | 137 | 0 | 0% | 0% |
| | | Chl 0.5 mM | 25 | 20 | 330 | 0 | 0% | 0% |
| | | Chl 1 mM | 30 | 20 | 375 | 0 | 0% | 0% |
| | | Chl 5 mM | 30 | 23 | 373 | 0 | 0% | 0% |

TABLE 4-continued

Related to Table 5. Results from all maternal chromosome knockout trials in *Ae. aegypti* using P2C-EGFP-Cas9.

| [Protein] (ug/ul) | [sgRNA] | Endosomal escape strategy | ♀ injected | (G$_{-1}$) ♀ Laying eggs | Wild type | Knock-out (KO) | GE/injected female | GE/G$_{-1}$ female |
|---|---|---|---|---|---|---|---|---|
| | | Chl 10 mM | 30 | 18 | 194 | 0 | 0% | 0% |
| | | Mon 1 mM | 20 | 18 | 405 | 0 | 0% | 0% |
| | | Sap 24 uM | 20 | 14 | 164 | 0 | 0% | 0% |
| | | Amm 50 mM | 20 | 18 | 265 | 0 | 0% | 0% |
| 3375 | 1396 | Chl 0.5 mM | 36 | 34 | 567 | 0 | 0% | 0% |
| | | Chl 1 mM | 36 | 29 | 579 | 1 | 3% | 3% |
| | | Chl 20 mM | 28 | 17 | 220 | 0 | 0% | 0% |
| 2258 | 1079 | Chl 0.5 mM | 32 | 28 | 149 | 1 | 3% | 4% |
| | | Chl 1 mM | 31 | 25 | 162 | 1 | 3% | 4% |
| | | Chl 1.8 mM | 22 | 20 | 228 | 1 | 5% | 5% |
| 6750 | 1406.3 | Chl 0.5 mM | 13 | 11 | 143 | 1 | 8% | 9% |
| 4214 | 903 | Chl 0.5 mM | 62 | 12 | 105 | 0 | 0% | 0% |
| 3375 | 1353 | Chl 0.5 mM | 36 | 11 | 80 | 3 | 8% | 27% |
| 3375 | 1394 | Chl 0.5 mM | 15 | 8 | 330 | 0 | 0% | 0% |
| 3375 | 1394 | Chl 0.5 mM* | 19 | 10 | 676 | 0 | 0% | 0% |
| 3375 | 1394 | Chl 0.5 mM* | 20 | 13 | 574 | 0 | 0% | 0% |
| 3375 | 1394 | Chl 0.5 mM | 15 | 10 | 379 | 0 | 0% | 0% |
| 1588 | 1405 | Chl 0.5 mM | 26 | 18 | 753 | 0 | 0% | 0% |
| 1125 | 1393 | Chl 0.5 mM | 26 | 19 | 809 | 0 | 0% | 0% |
| 502 | 1393 | Chl 0.5 mM | 26 | 13 | 421 | 0 | 0% | 0% |
| | | | 816 | 478 | 9379 | 11 | 1.3% | 2.3% |

[a]Endosomal Escape Reagent
Chl: Chloroquine,
Mon: Monensin,
Sap: Saponin.
Amm: Ammonium chloride
Bold highlights injections performed under "optimized" conditions of timing, Cas9, sgRNA, and chl concentrations.
*= Early injection at 5 hours PBF.
GE = gene editing events.

TABLE 5

Results from all successful ReMOT Control trials. See Tables 4 and 8 for all trials and conditions.

| Time of injection (PBF) | Injection components | | | G$_{-1}$ Females | | G$_0$ Offspring | | | Gene editing (GE) Efficiency | | |
|---|---|---|---|---|---|---|---|---|---|---|---|
| | Cas9 (ng/µL) | sgRNA (ng/µL) | [EER[a]] | Injected (IG$_{-1}$) | Ovipositing (OG$_{-1}$) | Wildtype (N) | Mosaic (N) | White (N) | GE/IG$_{-1}$ | GE/OG$_{-1}$ | GE/G$_0$ Larvae |
| Maternal gene editing: Wild-type females x white eye males | | | | | | | | | | | |
| 24 h | 3375 | 1394 | Chl (0.5 mM) | 36 | 11 | 80 | 0 | 3 | 8.3% | 27.3% | 3.6% |
| 28 h | 3375 | 1394 | Chl (0.5 mM) | 39 | 17 | 375 | 0 | 2 | 5.1% | 11.8% | 0.5% |
| 30 h | 3338 | 1175 | Chl (0.5 mM) | 15 | 6 | 79 | 0 | 1 | 6.7% | 16.7% | 1.3% |
| 54 h | 3375 | 1397 | Chl (1.0 mM) | 36 | 29 | 579 | 1 | 0 | 2.8% | 3.4% | 0.2% |
| 54 h | 2258 | 1079 | Chl (0.5 mM) | 32 | 28 | 149 | 1 | 0 | 3.1% | 3.6% | 0.7% |
| 54 h | 2258 | 1079 | Chl (1.0 mM) | 31 | 25 | 162 | 1 | 0 | 3.2% | 4.0% | 0.6% |
| 54 h | 2258 | 1079 | Chl (1.8 mM) | 22 | 20 | 228 | 0 | 1 | 4.5% | 5.0% | 0.4% |
| 54 h | 6750 | 1406 | Chl (0.5 mM) | 13 | 11 | 143 | 0 | 1 | 7.7% | 9.1% | 0.7% |
| | | | Total | 224 | 147 | 1795 | 3 | 8 | 4.9% | 7.5% | 0.6% |
| Paternal gene editing: White eye females x Wild-type males | | | | | | | | | | | |
| 48 h | 3375 | 1353 | none | 18 | 4 | 9 | 0 | 1 | 5.6% | 25.0% | 10.0% |
| 52 h | 3375 | 1040 | Mon (1 mM) | 20 | 11 | 53 | 1 | 0 | 5.0% | 9.1% | 1.9% |
| 52 h | 3375 | 1040 | Sap (24 uM) | 20 | 11 | 160 | 1 | 0 | 5.0% | 9.1% | 0.6% |
| | | | Total | 58 | 26 | 222 | 2 | 0 | 3.4% | 7.7% | 0.9% |
| Maternal & Paternal gene editing: Wild type females x Wild-type males | | | | | | | | | | | |
| 54 h | 3375 | 1353 | Chl (0.5 mM) | 58 | 40 | 1413 | 1 | 0 | 1.7% | 2.5% | 0.1% |

TABLE 6

Related to Table 5. Screening of G1 individuals from G0 adults obtained by female injection of a wild-type × wild-type outcross.

|  | Outcross | Number of adult $G_0$ | Number of adult wild-type | $G_1$ Larvae (N) | Number of White |
|---|---|---|---|---|---|
| Cage 1 | $G_0$ male × white female | 411 | 572 | 4796 | 9 |
| Cage 2 | $G_0$ female × white male | 385 | 744 | 6365 | 0 |
| Total |  |  | 1316 | 11161 | 9 |

TABLE 7

Related to Table 5. Results from all paternal allele knockout trials in *Ae. aegypti* using P2C-EGFP-Cas9.

| Protein (ug/ul) | sgRNA | Endosomal escape strategy[a] | ♀ injected | Ovipositing | Wild type | White | GE/injected female | GE/$G_{-1}$ female |
|---|---|---|---|---|---|---|---|---|
| 1866 | 1863 | None | 18 | 7 | 78 | 0 | 0% | 0% |
| 1250 | 1853 | None | 10 | 3 | 73 | 0 | 0% | 0% |
| 1250 | 1853 | Dynasore | 15 | 1 | 4 | 0 | 0% | 0% |
| 1250 | 1853 | None | 12 | 7 | 102 | 0 | 0% | 0% |
| 3375 | 1353 | None | 18 | 4 | 9 | 1 | 5.5% | 25% |
| 3337 | 1167 | Chl (0.5 mM) + Mon ($10^{-8}$ M) | 12 | 5 | 88 | 0 | 0% | 0% |
| 3000 | 1086 | Chl 1 mM | 20 | 15 | 136 | 0 | 0% | 0% |
| 3375 | 1040 | Chl 0.5 mM | 28 | 16 | 162 | 0 | 0% | 0% |
| 3375 | 1040 | Chl 10 mM | 20 | 14 | 78 | 0 | 0% | 0% |
| 3375 | 1040 | Mon 1 mM | 20 | 11 | 53 | 1 | 5% | 9% |
| 3375 | 1040 | Sap 24 uM | 20 | 11 | 160 | 1 | 5% | 9% |
| 3375 | 1040 | Amm 50 mM | 20 | 8 | 29 | 0 | 0% | 0% |
|  |  |  | 213 | 40 | 972 | 4 | 3.3% | 5.4% |

[a]Endosomal Escape Reagent
Chl: Chloroquine,
Mon: Monensin,
Sap: Saponin.
Amm: Ammonium chloride
Bolded numbers highlight positive gene editing events.
GE = Gene editing events.

TABLE 8

Heritability test in *Aedes aegypti*. Individual G0 adults showing a gene edited phenotype (white or mosaic eyes) were mated to white eye Wh-Iso8-kmo460 adults. See FIG. 10B.

| # Test | G0 adults | | | G1 Offspring (N) | | | |
|---|---|---|---|---|---|---|---|
|  | ID | Phenotype | Sex | # Egg batches | Wild type | White | % White eye |
| 1 | Mon-KO8 | Mosaic | Male | 1 | 18 | 17 | 48.57% |
|  | Sap-KO11 | Mosaic | Male | 1 | 14 | 16 | 53.33% |
| 2 | KO-2021-1.8 | White | Female* | 1 | 0 | 61 | 100% |
|  |  |  |  | 2 | 0 | 52 | 100% |
| 3 | KO6-2 | White | Male | 1 | 0 | 51 | 100% |
| 4 | KO6-3 | White | Female | 1 | 0 | 23 | 100% |

Example 4

*Bemisia tabaci* cryptic species Middle East-Asia Minor I (MEAM1) is a serious agricultural polyphagous insect pest, and vector of numerous plant viruses, causing major worldwide economic losses. *B. tabaci* control is limited by lack of robust gene editing tools. Gene editing is difficult in *B. tabaci* due to small embryos that are technically challenging to inject, and which have high mortality post-injection. We developed a CRISPR-Cas9 gene editing protocol based on injection of vitellogenic adult females rather than embryos ("ReMOT Control"). We identified an ovary-targeting peptide ligand ("BtKV") that, when fused to Cas9 and injected into adult females, transduced the ribonucleoprotein complex to the germline, resulting in efficient, heritable editing of the offspring genome. In contrast to embryo injection, adult injection is easy and does not require specialized equipment. Development of easy-to-use gene editing protocols for *B. tabaci* will allow researchers to apply the power of reverse genetic approaches to this species and will lead to novel control methods for this devastating pest insect.

Bemisia tabaci cryptic species Middle East-Asia Minor I (MEAM1) is a widely distributed invasive agricultural pest that causes the economic loss of billions of dollars in crop damages worldwide[1,2]. B. tabaci is polyphagous with a broad host range. This insect feeds on plant phloem sap through its life cycle using piercing-sucking mouthparts and can cause direct damage to the plants. The honeydew excretions from whiteflies promote fungus growth that can reduce photosynthesis and crop yields. Finally, B. tabaci is an important vector of numerous plant viruses that affect economically critical crop species. B. tabaci is the only known vector of begomoviruses, a family of plant viruses known to cause plant diseases and adversely affect crop yield. Current control methods for B. tabaci are insecticides, and limited use of biological control[3,4]. Plant-mediated RNAi targeting begomoviruses or the whitefly vector has shown some promise in laboratory settings but has not been translated to field applications[5-8]. Although RNAi can be effective at reducing gene transcription, efficacy can be highly variable depending on the gene and tissue of interest. Thus far, the lack of tools to genetically manipulate whitefly hinders the screening of potential genetic targets that can be used to design agricultural control strategies.

The economic importance of B. tabaci demands new methods to control this devastating pest insect. Gene editing, using CRISPR-Cas9, has formed the foundation for novel control strategies for insect vectors of human diseases[9-13] and plant diseases[14], but lack of gene editing techniques for B. tabaci is a significant barrier to the application of gene editing for basic biological studies and control of this insect. Arthropod gene editing by CRISPR-Cas9 is usually performed by injecting gene-editing materials into pre-blastoderm embryos, but the exceedingly small size of B. tabaci embryos (0.2 mm) and high mortality of injected eggs makes this technically challenging. A method has recently been developed called "ReMOT Control" (Receptor-Mediated Ovary Transduction of Cargo) which circumvents the need to inject embryos, but rather uses a small ovary-targeting peptide to directly transduce the Cas9 ribonucleoprotein complex (RNP; the Cas9 protein complexed with a guide RNA) into the developing ovaries upon injection into the hemolymph of adult female insects. ReMOT Control has been shown to efficiently edit the germline of the mosquitoes Aedes aegypti and Anopheles stephensi[9,10].

Here, we develop an efficient ReMOT Control CRISPR-Cas9-based adult injection protocol for gene editing in B. tabaci. The development of robust gene editing methodologies for this species opens the power of CRISPR and reverse genetic approaches to study the biology and develop new control strategies for this important economic pest.

Bemisia tabaci Colony Maintenance

A colony of B. tabaci MEAM1 (originally collected from a poinsettia plant in Ithaca, NY) was maintained in a growth chamber set at 28° C.+/−2° C., 14L/10D photoperiod and 50% relative humidity in 24×24×24 inch cages with organza access sleeves. Insects were maintained on organic soybean (var. Viking, Johnny's Selected Seeds), organic radish (var. Cherry Belle, Burpee Seeds and Plants), and/or gerbera daisy (var. Garvinea, Burpee Seeds and Plants). Plants were grown in a separate growth chamber using the same parameters as the insect growth chamber. Plants were grown in 6-inch pots using enriched potting media, with liquid fertilizer (Peter's Excel Cal-Mag 15-5-15) applied twice a month.

Plasmid Construction and Protein Expression

Figure 21:
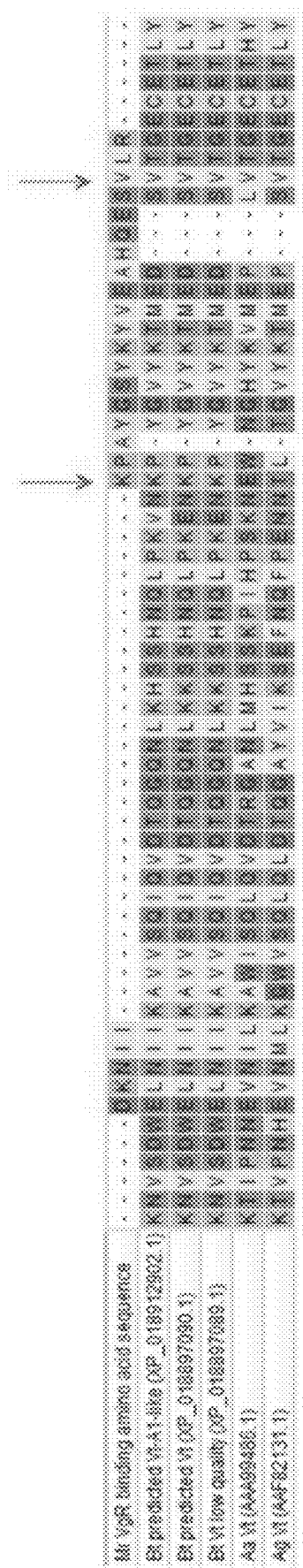

Based on a predicted 24 aa vitellogenin binding sequence from the crustacean Macrobrachiumrosen bergii[15] we identified the homologous sequence from multiple B. tabaci vitellogenin genes (XP_018897090, XP_018912902, XP_018897089), and from the mosquitoes Ae. aegypti (AAA994861.1), and An. gambiae (AAF82131.1). We identified a lysine conserved across B. tabaci sequences and a fully conserved valine residue that defined the ends of the targeting sequence ("BtKV") (FIG. 21). pET28A-BtKV-Cas9 was constructed from pET28-P2C-Cas9[10] and a gblock (IDT) of BtKV-mCherry. pET28A-P2C-Cas9 was digested with restriction enzymes BamHI and SalI. A gblock of BtKV fused to mCherry was synthesized and inserted into the digested pET28-P2C-Cas9 using In-Fusion Cloning (Takara). Sanger sequencing was used to verify the sequence. pET28A-BtKV-mCherry-Cas9 was further digested with either SalI or XhoI to remove mCherry or Cas9 respectively, gel purified, and re-ligated using T4 ligase to obtain the plasmids pET28A-BtKV-Cas9 or pET28A-BtKV-mCh. Plasmids were transformed into BL21(DE3) cells for BtKV-Cas9/mCh expression following standard protein expression protocols. P2C-Cas9 and Cas9 were expressed using plasmids as previously described[10]. Briefly, a 5 mL starter culture grown overnight at 37° C. with shaking at 225 rpm was used to inoculate 50 mL Terrific Broth (Invitrogen) at a 1:100 dilution. When the culture reached an OD600 of 0.4-0.8, it was induced with isopropyl-β-D-1-thiogalactopyranoside (IPTG) at [500 µM] concentration at 20° C. overnight. Cultures were pelleted, resuspended in lysis buffer (20 mM Tris-HCl pH 8.0, 300 mM NaCl, 20 mM imidazole) and sonicated. Cell debris was pelleted and the supernatant collected and used for immobilized metal affinity chromatography using Ni-NTA agarose beads (Qiagen) and agitated for at least 2 hours at 4° C. Subsequently, the beads were separated in a chromatography column and washed with lysis buffer allowing gravity flow. Proteins were eluted (20 mM Tris-HCl pH 8.0, 300 mM NaCl, 250 mM imidazole) and dialyzed in 20 mM Tris-HCl pH 8.0, 300 mM KCl, 500 µM phenylmethylsulfonyl fluoride. Proteins were concentrated using an Amicon Ultra-0.5 mL centrifugal filter device with a cutoff of 100 kDa (Millipore Sigma).

Generating Guide RNAs sgRNA were generated following the protocols found here[11]. The 20 nucleotide guide sequences were designed against exon 2, exon 3, and exon 5 of the B. tabaci white gene (NW_017550151, region 408016-472564) both manually and by CRISPOR[16]. Primers and guide RNA sequences are listed in Table 10.

Injection Protocol for Bemisia tabaci

For initial experiments B. tabaci adults of unknown age and mating status were aspirated from the colony cage into 2-dram screw cap vials, placed in ice to anesthetize the insects, sexed, and transferred to a standard plain glass slide with double-sided tape on a chill table. For later experiments we established a synchronous colony so that we could control for the age of injected insects (see below). For localization of BtKV fusion protein into the embryos, female B. tabaci were injected in the abdomen with BtKV-mCherry fusion protein (3 mg/ml) or PBS control using quartz capillary needles. Samples were collected 24 hours post injection and ovaries dissected onto a concavity microscope slide with a glass coverslip and imaged by epifluorescence microscopy.

To generate mutants, the injection mixture consisted of the RNP complex of BtKV-Cas9 (3 mg/mL) with a mix of all sgRNAs (3 mg/mL) at a 1:3 molar ratio, and ⅓$^{rd}$ the volume of saponin [4, 8, or 16 μg/mL] as an endosome escape reagent (or buffer as a control)[9,10]. Five sgRNA multiplexed were used at a concentration of 250 ng/μL each and 1.25 μg/μL total. Two groups of females were collected: 1) Females of unknown age and unknown mated status were collected at random and 2) females less than 24 hours post emergence (hpe) were collected to reduce their chances of having already developed eggs[18]. The females were injected and placed on a piece of soybean leaflet in a petri dish with a moist paper towel wrapped around the stem and another paper towel on the bottom plate to prolong the life of the leaflet. Water and liquid fertilizer were added as needed. Females were removed from the leaflet 2 weeks post injection. The petri dishes were incubated at 28° C., 16L/8D cycle, in a humidified Heratherm IMH750-S reach-in chamber, and the progeny of injected females screened visually for altered eye color in nymphs or adults using an Olympus SZX7 stereomicroscope. Mutations in insects showing altered eye color were confirmed by PCR using PHIRE Tissue Direct PCR Master Mix (Thermo Fischer Scientific), the amplicon was cloned into pJET1.2, and clones were submitted for Sanger sequencing.

Heritability Crosses

Figure 20:
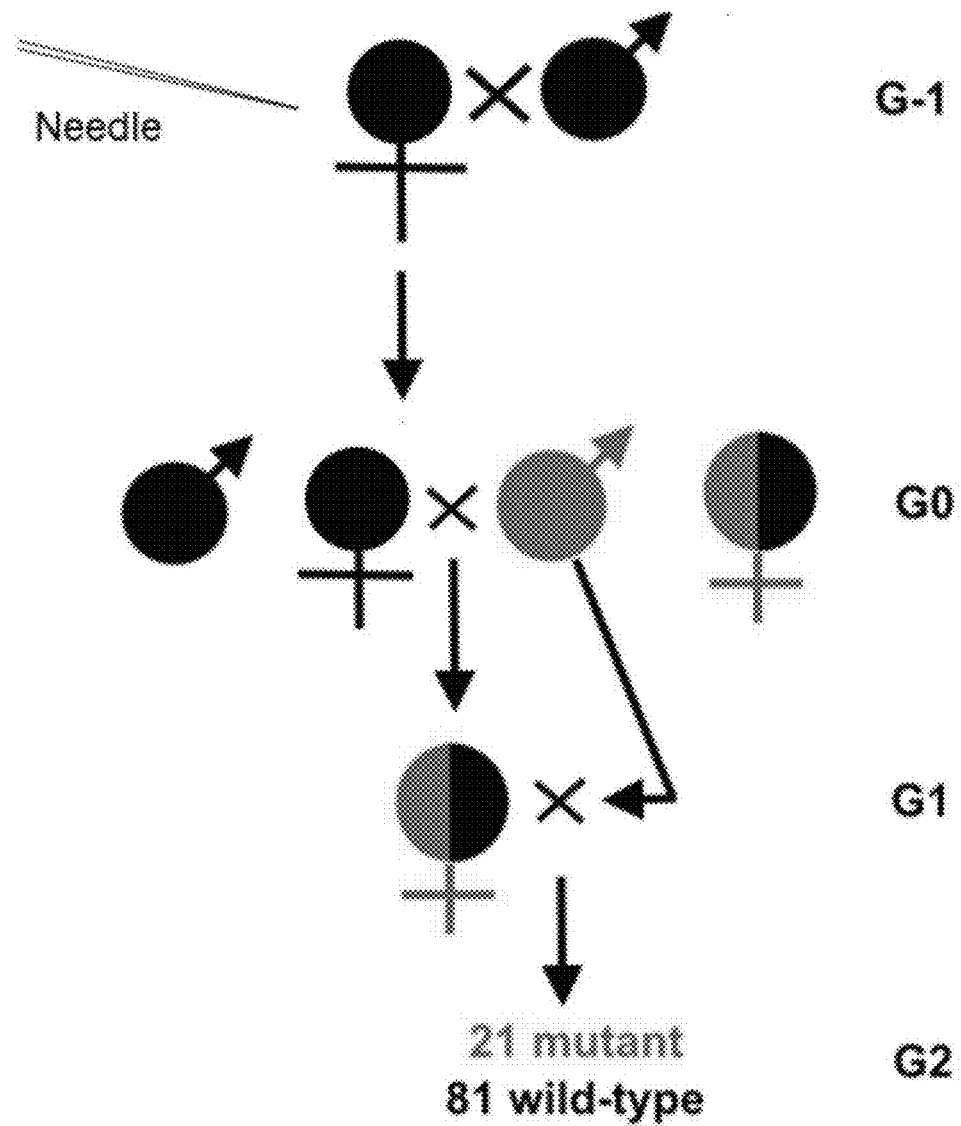

Crosses of mutant males and wild-type females were performed (FIG. 20) to demonstrate heritability of the mutant allele and phenotype. In brief, G0 mutant males resulting from injection of G−1 females were interbred with wild-type G0 females. Resulting G1's were sexed and separated approximately 24 hpe. G1 females were backcrossed to a G0 mutant male to generate G2 offspring. Insects were screened for eye color in the nymphal stage.

Homology Modeling of Mutated Proteins

A homology model of one in-frame insertion mutant [21 bp] was generated using the Swiss Model homology server (swissmodel.expasy.org). The structure of the *B. tabaci* white gene has not been empirically solved, so a model of the wild-type protein was first generated against the database using the server, the result of which was used as template to model the [21 lbp] insertion mutant.

Identification and Validation of the BtKV Ovary Targeting Ligand

Figure 17:
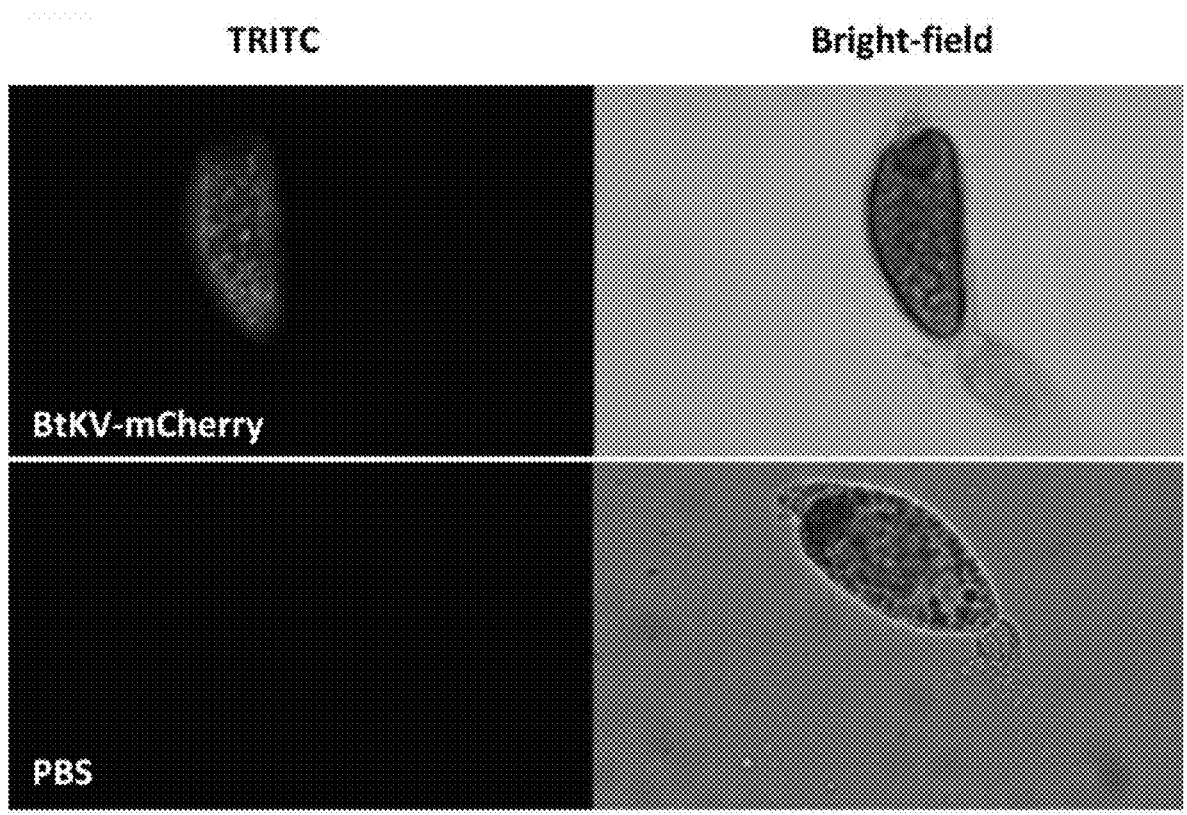
FIG. 17 shows the targeting of molecular cargo to *B. tabaci* ovaries. The BtKV peptide KPYGVYKTMEDSV (SEQ ID NO: 30) targets molecular cargo (mCherry-Cas9 fusion protein) into *B. tabaci* ovaries and is visible in dissected mature oocytes 24 hours post-injection (top). No signal is visible in control ovaries (bottom).
Figure 18:
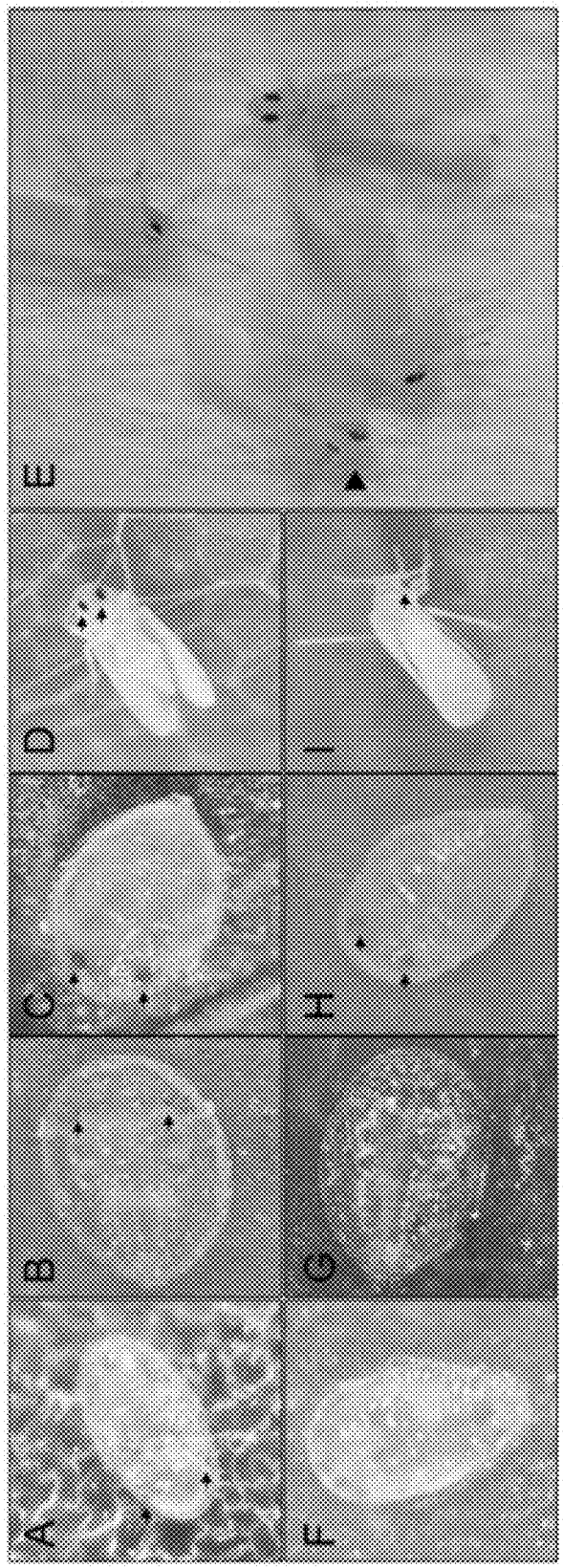
Figure 19A:
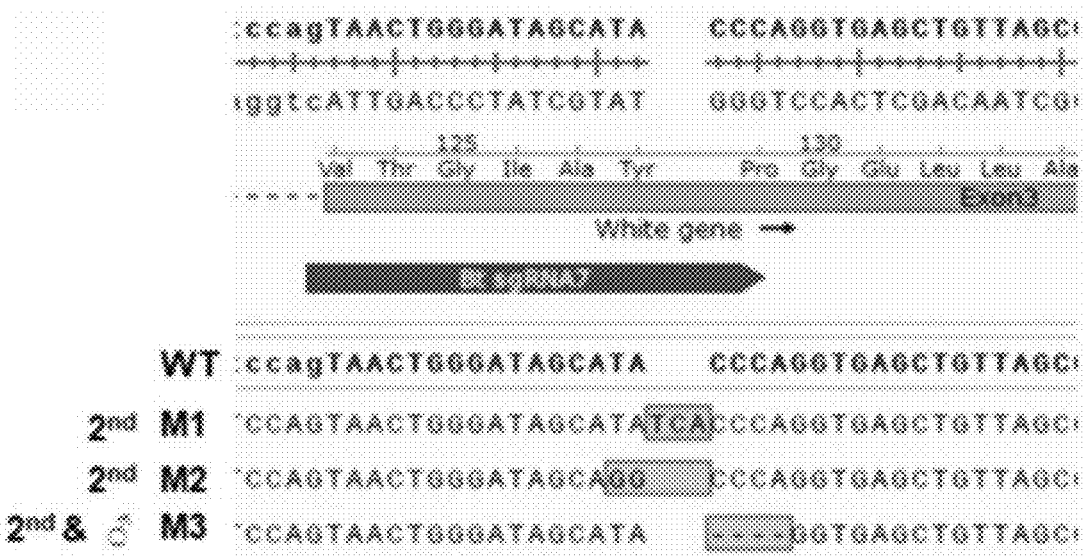
Figure 19B:
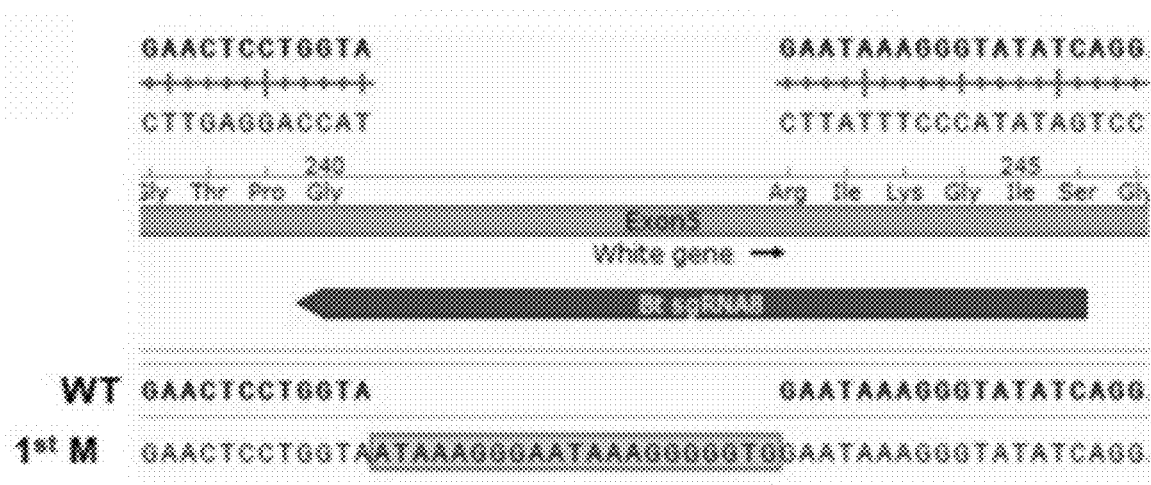
Figure 19C:
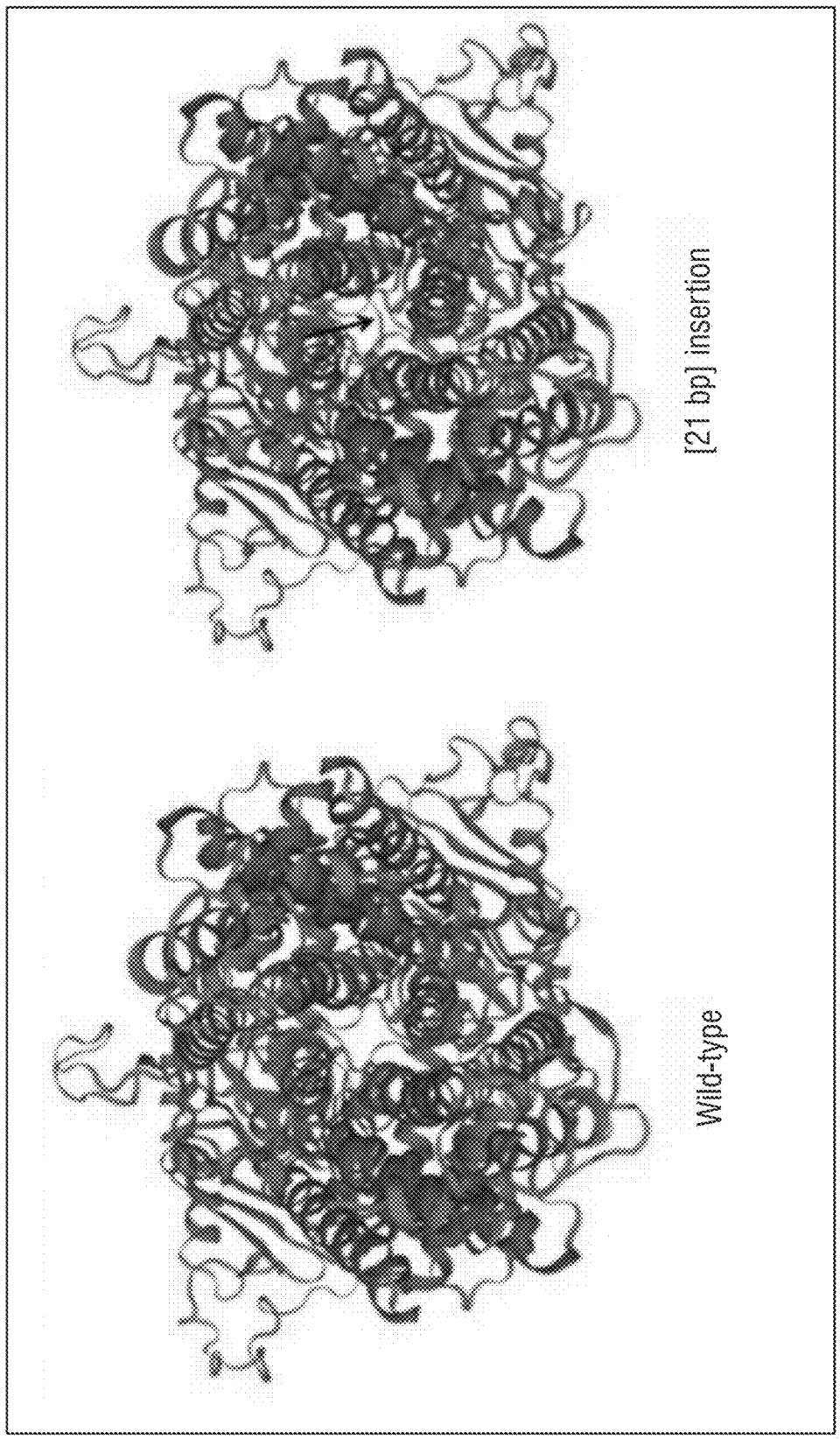

While the P2C ligand works to target cargo to the ovaries of multiple mosquito species[9,10], it did not function robustly in *B. tabaci* (Table 9). We therefore designed a new targeting peptide suitable for this insect species based on its endogenous vitellogenin protein ("BtKV"; KPYGVYKTMEDSV (SEQ ID NO: 30)) (see methods). *B. tabaci* oocyte development is asynchronous with stage I, II, III, and IV at 11 days post eclosion or older[19] where oocytes are always developing. Developmental phase II oocytes have the highest amount of vitellogenin uptake via endocytosis and nutrient cord[19]. After injection of BtKV-mCherry into reproductive adult *B. tabaci* females, ovaries were dissected after 24 hours and visualized for red fluorescence. We observed red fluorescence in the developing oocytes from females injected with BtKV-mCherry fusion protein but not PBS-injected controls (FIG. 17).

Knockout of the *B. tabaci* White Gene by ReMOT Control

For proof of principle gene editing experiments, we chose the white gene, which is an ABC transporter protein responsible for transport of ommochrome pigments into the eyes. Null mutants for this gene have white eyes in multiple taxa[20, 22]. Cas9 proteins were complexed with 5 sgRNAs targeting exons 2, 3 and 5 of the gene (Table 10). We used saponin as an endosome escape reagent as it was functional in *Aedes aegypti* and *Anopheles gambiae* ReMOT Control editing experiments[9,10].

Cas9 RNP injections with no targeting peptide or with P2C as the targeting peptide, with or without saponin, did not result in any visibly edited offspring (Table 9). For injections using BtKV as the targeting peptide, white-eye nymphal offspring were recovered from 7 of 14 independent replicate injection experiments (FIG. 18, Table 9). The data showed that mutants were only recovered in treatments without saponin, or the lowest concentration of saponin; higher concentrations of saponin were inhibitory (Table 9). Mutants were recovered in 7 out of 9 independent injection experiments using less than or equal to 4 μg/mL saponin. Finally, females less than 24 hpe with or without saponin generated mutants with higher efficiency compared to females of unknown ages (Table 9). Early nymphal instar mutants had white (colorless) eyes but during development the color changed to a bright orange-red color (FIG. 18) compared to the dark red-brown color of the wild-type.

Due to the haplodiploid nature of *B. tabaci*, we are much more likely to observe mutant males as they are haploid. While we can not determine the sex of mutants that did not survive to adulthood, all mutants that did make it to the adult stage were male. We assume that mutants identified in the immature stage were male as well. This can bias actual estimates of editing efficiency if the sex ratio is not 50:50. *B. tabaci* females can actively control the sex ratio of their offspring by controlling which eggs are fertilized, and published estimates of the sex ratio range from 25% to 75% female[23]. We examined the sex ratio in our colony 9 replicate times by random sampling and found it to be highly female biased, with estimates ranging from 65% to 85% female, and an average value of 73% female (Table 11). When adjusted for sex ratio bias, we calculated an editing rate in male offspring within a range of 0.39%-20.72% (Table 9), depending on whether young females were injected. When females <24 hpe were injected, editing rates in the offspring were >20% in some replicates, high enough for lineage screening by PCR to identify mutant individuals in the case of a gene without an obvious morphological phenotype. Across all replicates using 4 μg/mL saponin or less, injection of approximately 12 females was enough to obtain at least one edited offspring, an editing efficiency almost two-fold greater than observed in mosquitoes[9,10]

Analysis of Mutants

From the 23 mutant offspring visually identified, we randomly selected 8 for molecular characterization and were able to obtain DNA of sufficient quality for sequencing from 5 offspring (3 white-eye 1st or 2nd nymphal instars, and 2 orange eye male adults. PCR of housekeeping genes was unsuccessful for the other 3 individuals, indicating degraded DNA. We validated gene knockout by PCR and sequencing of the product of the targeted gene locus in these 5 individuals. The sequencing produced multiple peaks for one individual, and so the PCR product was cloned into pJET1.2 and 9 clones were sequenced. This individual (although phenotypically white eye) appeared to be a genetic mosaic, where we detected wild-type alleles and 2 insertion alleles (a 3 nucleotide insertion and a 2 nucleotide substitution). Another white-eye juvenile had a 21 bp in-frame insertion (insertion mutant [21 bp]). Homology modeling of this mutation predicted that it caused a loop to be cast across the pore region of the transporter, likely blocking the transport function of the gene by steric interference (FIG. 19). The final white-eye juvenile had a 4 bp deletion in exon 3 causing a frame shift of the white gene. Similarly, the two orange-red eye males had the same 4 bp deletion.

Heritability of Generated Mutations

To demonstrate that the mutations generated by ReMOT Control were heritable in B. tabaci, we performed a cross (FIG. 20) between male and female offspring of injected females. The males used in the cross were visibly mutant (white-eye as juvenile, orange-red eye as adults). The females were phenotypically wild-type. All 90 G1 offspring had wild-type eye color which indicates that the parents consisted of a mutant male and wild-type females. Subsequently, G1 females were backcrossed with the same G0 mutant male. The expected ratio of mutant to wild-type offspring resulting from a cross between a haploid mutant male to a hemizygous mutant female is 50:50. We observed 22 mutants and 81 wild-type offspring suggesting a deviation from the expected ratio (Chi-square=17.84, P<0.0001), Nevertheless, the data demonstrate that the mutation was heritable and thus the germline was edited.

Discussion

In this report, we demonstrated heritable CRISPR-Cas9 gene editing in B. tabaci using ReMOT Control by changing the ovary targeting ligand from P2C to BtKV. P2C was derived from the yolk protein of Drosophila melanogaster* and was used for gene editing in *Aedes aegypti*[10] and *Anopheles stephensi*[9]. In our experiments, P2C did not generate knockouts in *B. tabaci*; thus, we identified a new 13 aa ligand from the native vitellogenin protein of *B. tabaci* to target the RNP for ReMOT Control. This resulted in high efficiency gene editing. In mosquitoes use of an endosomal escape reagent is critical to the success of ReMOT Contro19, 10, and saponin was shown to be highly effective[9]. However, in *B. tabaci* we found a chemical endosomal escape reagent was unnecessary, and in fact saponin was detrimental to the process. This result demonstrates that ReMOT Control must be independently optimized for each new species, as parameters that are successful in one system may not work in others.

ReMOT Control transduces Cas9 RNP into the ovaries of females, so it cannot edit the paternal derived chromosome until after the egg has been fertilized. Thus, the maternal chromosome is edited more efficiently than the paternal chromosome[9,10]. *B. tabaci* is haplodiploid, where females are diploid and haploid males result from unfertilized eggs. Because ReMOT control preferentially edits the maternal chromosome, obtained white-eye nymphal instars were likely haploid males that developed from an unfertilized egg with a single edited chromosome. Haplodiploidy is an advantage for ReMOT Control because mutations in the female germline can be immediately recognized in the haploid male offspring. Consistent with this, all G0 mutant adults with orange-red eyes were males. To effectively exploit the haplodiploidy feature, we obtained females less than 24 hpe to inject to limit pre-injection egg development, as well as potentially limiting the chances of mating thus favoring male bias offspring, making it easier to screen for the visually noticeable phenotype.

Our cross experiment demonstrated that mutations generated by ReMOT Control are in the germline and can be passed down to offspring by heredity, rather than just editing the somatic tissues. Mutations were inherited in deviation of expected Mendelian ratios, possibly due to differential hatching of mutant vs. wild-type eggs.

We observed white-eye nymphs from $1^{st}$ to early $4^{th}$ instar and an unexpected orange-red eye phenotype in the mutant late $4^{th}$ instar nymphs and adults. During the late $4^{th}$ instar nymphal stage, the eyes of the pharate adult become diffused, heavily pigmented, and distinct[24], which means that the noticeable change in eye color during the late stages of the $4^{th}$ nymphal instar are the adult eyes. The change in pigmentation in *B. tabaci* is different from the brown leafhopper *Nilaparvata lugens*, another hemimetabolous insect. Mutation of the white gene in *N. lugens* yieled a white ocelli and a light red pigmented eye where the eye pigments were consistent throughout the life stages[14]. Both ommochrome (brown/black) and pteridine (red/orange/yellow) pigments contribute to eye color in insects[25]. We speculate that the *B. tabaci* white gene is responsible for transportation of the brown ommochrome pigments into the eye; with it mutated the red pteridine pigments become visible, explaining the shift in eye color of mutant insects, although further research is required to confirm or refute this hypothesis.

We have shown in this work that ReMOT Control allows easy and efficient CRISPR editing in *B. tabaci* without the need to inject embryos. The eggs of *B. tabaci* have a pedicel that is embedded into leaf tissue and acts a conduit for water and solute absorption into the eggs for successful embryonic development and hatching[26]. This character, along with the exceeding small size of the embryos (~0.2 mm×0.01 mm) and high mortality of injected eggs presents significant challenges for the success of embryo injections. ReMOT Control removes these constrains and significantly expands the ability for any laboratory to apply CRISPR techniques to whitefly research, which will greatly accelerate molecular biology research on this organism and lead to the development of novel control strategies for this economically devastating pest insect. Furthermore, this technology can be applied readily to other whitefly species and to related insect groups, e.g. psyllids, mealybugs, which also include major agricultural pests.

TABLE 9

| Injection | Saponin (ug/Ml) | N Females Injected | Sampling Method | N Offspring Screened | N Offspring Edited | KO Injected % | KO/offspring % | KO offspring % sex ratio corrected |
|---|---|---|---|---|---|---|---|---|
| Cas9 | 0 | 31 | Random | 70 | 0 | 0 | 0 | 0 |
| Cas9 | 4 | 28 | Random | 218 | 0 | 0 | 0 | 0 |
| P2C-Cas9 | 0 | 20 | Random | 54 | 0 | 0 | 0 | 0 |
| P2C-Cas9 | 4 | 13 | Random | 74 | 0 | 0 | 0 | 0 |
| BtKV-Cas9 | 0 | 42 | Random | 961 | 1 | 2.38% | 0.10% | 0.39% |
| BtKV-Cas9 | 4 | 47 | Random | 261 | 2 | 4.26% | 0.77% | 2.84% |
| BtKV-Cas9 | 4 | 47 | Random | 189 | 1 | 2.13% | 0.53% | 1.96% |
| BtKV-Cas9 | 4 | 30 | Random | 314 | 1 | 3.33% | 0.32% | 1.18% |
| BtKV-Cas9 | 4 | 28 | Random | 180 | 1 | 3.57% | 0.56% | 2.06% |
| BtKV-Cas9 | 8 | 31 | Random | 378 | 0 | 0 | 0 | 0 |
| BtKV-Cas9 | 8 | 29 | Random | 144 | 0 | 0 | 0 | 0 |
| BtKV-Cas9 | 16 | 34 | Random | 121 | 0 | 0 | 0 | 0 |
| BtKV-Cas9 | 16 | 22 | Random | 284 | 0 | 0 | 0 | 0 |
| BtKV-Cas9 | 16 | 29 | Random | 73 | 0 | 0 | 0 | 0 |
| BtKV-Cas9 | 0 | 14 | <24 hpe | 226 | 0 | 0 | 0 | 0 |
| BtKV-Cas9 | 0 | 21 | <24 hpe | 118 | 15 | 71.43% | 12.71% | 20.72%* |
| BtKV-Cas9 | 4 | 15 | <24 hpe | 96 | 0 | 0 | 0 | 0 |
| BtKV-Cas9 | 4 | 26 | <24 hpe | 243 | 2 | 7.69% | 0.82% | 1.03%* |

*Sex ratio corrected based on ratio of emerged males and females in the injected group.

TABLE 10

Primer and guide RNA sequences used in this study

| Primer Name | Sequence | Source |
|---|---|---|
| 7.Ex3.F1 | ATCCACTGTGCGGCATTCTT (SEQ ID NO: 66) | Here |
| 7.Ex3.R1 | TTCCATTGACTGCTCGCTGG (SEQ ID NO: 67) | Here |
| 8.Ex5.F1 | TGCTGGAAAGGTAGAATTTGAACG (SEQ ID NO: 68) | Here |
| 8.Ex5.R1 | TGGATGCCCAACAACATTCTTT (SEQ ID NO: 69) | Here |
| sgRNA.2F.Ex2 | gaaattaatacgactcactataGTGAGGACGCATTGGTCTGTgttttagagctagaaatagc (SEQ ID NO: 70) | Here |
| sgRNA.5F.Ex2 | gaaattaatacgactcactataGTTGATGCCGGACCACGTGTgttttagagctagaaatagc (SEQ ID NO: 71) | Here |
| sgRNA.6F.Ex2 | gaaattaatacgactcactataGGCATCAACGTCTTCGCCTCgttttagagctagaaatagc (SEQ ID NO: 72) | Here |
| sgRNA.7F.Ex3 | gaaattaatacgactcactataGTAACTGGGATAGCATACCCgttttagagctagaaatagc (SEQ ID NO: 73) | Here |
| sgRNA.8F.Ex5 | gaaattaatacgactcactataGATATACCCTTTATTCTACCgttttagagctagaaatagc (SEQ ID NO: 74) | Here |
| sgRNA R | AAAAGCACCGACTCGGTGCCACTTTTTCAAGTTGATAACGGACTAGCCTTATTTTAACTTGCTATTTCTAGCTCTAAAAC (SEQ ID NO: 75) | Kistler et al. 2015 |

TABLE 11

B. tabaci colony sex ratio.

| sample | female | male |
|---|---|---|
| 1 | 44 | 17 |
| 2 | 20 | 11 |
| 3 | 20 | 9 |
| 4 | 21 | 5 |
| 5 | 11 | 4 |
| 6 | 22 | 8 |
| 7 | 22 | 6 |
| 8 | 22 | 7 |
| 9 | 22 | 9 |
| Average | 22.7 | 8.4 |
| Ratio | 2.7 | 1 |

REFERENCES

1. A. K. Inoue-Nagata, et al., A review of geminivirus diseases in vegetables and other crops in Brazil: current status and approaches for management. *Hortic. Bras.* 34, 8-18 (2016). https://doi.org/10.1590/S0102-053620160000100002.
2. H. Czosnek, A. Hariton-Shalev, I. Sobol, R. Gorovits, M. Ghanim, The incredible journey of Begomoviruses in their whitefly vector. *Viruses* 9 (2017). https://doi.org/10.3390/v9100273.
3. M. Faria, S. P. Wraight, Biological control of *Bemisia tabaci* with fungi. *Crop Prot.* 20, 767-778 (2001). https://doi.org/10.1016/S0261-2194(01)00110-7.
4. D. Gerling, Ò. Alomar, J. Arnò, Biological control of *Bemisia tabaci* using predators and parasitoids. *Crop Prot.* 20, 779-799 (2001). https://doi.org/10.1016/S0261-2194(01)00111-9.
5. S. Kanakala, S. Kontsedalov, G. Lebedev, M. Ghanim, Plant-mediated silencing of the whitefly *Bemisia tabaci* cyclophilin B and heat shock protein 70 impairs insect development and virus transmission. *Front. Physiol.* 10, 557 (2019). https://doi.org/10.3389/fphys.2019.00557.
6. Y. Luo, et al., Towards an understanding of the molecular basis of effective RNAi against a global insect pest, the whitefly *Bemisia tabaci*. *Insect Biochem. Mol. Biol.* 88, 21-29 (2017). https://doi.org/10.1016/j.ibmb.2017.07.005.

7. H. J. Malik, et al., RNAi-mediated mortality of the whitefly through transgenic expression of double-stranded RNA homologous to acetylcholinesterase and ecdysone receptor in tobacco plants. *Sci. Rep.* 6, 38469 (2016). doi: 10,1038/srep38469.
8. A. Raza, et al., RNA interference based approach to down regulate osmoregulators of whitefly (*Bemisia tabaci*): Potential technology for the control of whitefly. *PLoS One* 11, e0153883 (2016). https://doi.org/10.1371/journal.pone.0153883.
9. V. M. Macias, et al., Cas9-Mediated Gene-Editing in the Malaria Mosquito *Anopheles stephensi* by ReMOT Control. G3 Genes, Genomes, Genet. 10 (2020). https://doi.org/10.1534/g3.120.401133
10. D. Chaverra-Rodriguez, et al., Targeted delivery of CRISPR-Cas9 ribonucleoprotein into arthropod ovaries for heritable germline gene editing. *Nat. Commun.* 9, 3008 (2018). https://doi.org/10.1038/s41467-018-05425-9.
11. K. E. Kistler, L. B. Vosshall, B. J. Matthews, Genome Engineering with CRISPR-Cas9 in the Mosquito *Aedes aegypti*. Cell Rep. 11, 51-60 (2015). https://doi.org/10.1016/j.celrep.2015.03.009.
12. Y. Dong, M. L. Simões, E. Marois, G. Dimopoulos, CRISPR/Cas9-mediated gene knockout of *Anopheles gambiae* FREP1 suppresses malaria parasite infection. *PLOS Pathog.* 14, e1006898 (2018). https://doi.org/10.1371/journal.ppat.1006898.
13. K. Kyrou, et al., A CRISPR-Cas9 gene drive targeting doublesex causes complete population suppression in caged *Anopheles gambiae* mosquitoes. Nat. *Biotechnol.* 36, 1062-1066 (2018). https://doi.org/10.1038/nbt.4245.
14. W.-H. Xue, et al., CRISPR/Cas9-mediated knockout of two eye pigmentation genes in the brown planthopper, *Nilaparvata lugens* (Hemiptera: Delphacidae). *Insect Biochem. Mol. Biol.* 93, 19-26 (2018). https://doi.org/10.1016/j.ibmb.2017.12.003.
15. Z. Roth, et al., Identification of receptor-interacting regions of vitellogenin within evolutionarily conserved β-sheet structures by using a peptide array. *ChemBioChem* 14, 1116-1122 (2013). https://doi.org/10.1002/cbic.201300152.
16. M. Haeussler, et al., Evaluation of off-target and on-target scoring algorithms and integration into the guide RNA selection tool CRISPOR. *Genome Biol.* 17, 148 (2016). https://dio.org/10.1186/s13059-016-1012-2.
17. T.-Y. Li, S. B. Vinson, D. Gerling, Courtship and mating behavior of *Bemisia tabaci* (Homoptera: Aleyrodidae). *Environ. Entomol.* 18, 800-806 (1989). https://doi.org/10.1093/ee/18.5.800.
18. J.-Y. Guo, et al., Enhanced vitellogenesis in a whitefly via feeding on a begomovirus-infected plant. *PLoS One* 7, e43567 (2012). https://doi.org/10.1371/journal.pone.0043567.
19. J.-Y. Guo, F.-H. Wan, G.-Y. Ye, Oogenesis in the *Bemisia tabaci* MEAM1 species complex. Micron 83, 1-10 (2016). https://doi.org/10.1016/j.micron.2016.01.003.
20. O. P. Perera, N. S. Little, C. A. Pierce, CRISPR/Cas9 mediated high efficiency knockout of the eye color gene Vermillion in *Helicoverpa zea* (Boddie). *PLoS One* 13, e0197567 (2018). https://doi.org/10.1371/journal.pone.0197567.
21. S. M. Mackenzie, et al., Mutations in the white gene of *Drosophila melanogaster* affecting ABC transporters that determine eye colouration. *Biochim. Biophys. Acta-Biomembr.* 1419, 173-185 (1999). https://doi.org/10.1016/S0005-2736(99)00064-4.
22. X. Bai, et al., CRISPR/Cas9-mediated knockout of the eye pigmentation gene white leads to alterations in colour of head spots in the oriental fruit fly, *Bactrocera dorsalis*. Insect Mol. Biol., imb.12592 (2019). https://doi.org/10.1111/imb.12592.
23. A. R. Horowitz, D. Gerling. Seasonal variation of sex ratio in *Bemisia tabaci* on cotton in Israel. *Environ. Entomol.* 21, 556-559 (1992). https://doi.org/10.1093/ee/21.3.556.
24. D. B. Gelman, M. B. Blackburn, J. S. Hu, D. Gerling, The nymphal-adult molt of the silverleaf whitefly (*Bemisia argentifolii*): Timing, regulation, and progress. Arch. *Insect Biochem. Physiol.* 51, 67-79 (2002). https://doi.org/10.1002/arch.10051.
25. J. L. Rasgon, T. W. Scott. Crimson: A Novel Sex-Linked Eye Color Mutant of *Culex Pipiens* L. (Diptera: Culicidae). *J. Med.* Entomol. 41, 385-391 (2004). https://doi.org/10.1603/0022-2585-41.3.385.
26. J. S. Buckner, T. P. Freeman, R. L. Ruud, C. Chu, T. J. Henneberry, Characterization and functions of the whitefly egg pedicel. Arch. *Insect Biochem. Physiol.* 49, 22-33 (2002). https://doi.org/10.1002/arch.10006.

What is claimed is:

1. A method for delivery of one or more molecules of interest to an oocyte of an animal, the method comprising,
   injecting into a vitellogenic female animal a functional fragment of a yolk protein precursor (YPP) linked to said one or more molecules of interest,
   wherein the YPP is a Drosophila Yolk Protein 1 (YP1) and wherein the functional fragment has 100% sequence identity to SEQ ID NO: 2 or SEQ ID NO: 3 and is capable of targeting the one or more molecules of interest to the oocyte.

2. The method of claim 1, wherein said animal is selected from the group of insects and/or vertebrate animals.

3. The method of claim 1, wherein said animal is an insect.

4. The method of claim 1, wherein said animal is a mosquito.

5. The method of claim 1, wherein said animal is selected from the group consisting of fish, frogs, lizards, birds, and monotremes.

6. The method of claim 1, wherein said molecule of interest is selected from a molecule inserted into the genome of said animal, a molecule of a gene editing system, an endonuclease, a detectable molecule, a selectable molecule, and a molecule that binds to a composition.

7. The method of claim 6, wherein said gene editing system comprises a CRISPR/Cas editing system.

8. The method of claim 7, wherein said molecule of interest is Cas.

9. The method of claim 1, wherein said functional fragment is SEQ ID NO: 2 or SEQ ID NO: 3.

10. A method of producing a gene edited animal having a stably inheritable edited genome, the method comprising, a) injecting into a vitellogenic female animal a functional fragment of a yolk protein precursor (YPP) linked to one or more molecules of interest,
wherein the YPP is a Drosophila Yolk Protein 1 (YP1), and wherein the functional fragment has 100% sequence identity to SEQ ID NO: 2 or SEQ ID NO: 3 and is capable of targeting the one or more molecules of interest to an oocyte, and wherein the one or more molecules of interest comprise at least one molecule of a gene editing system;
b) delivery of said molecule of interest to said oocyte of said animal under conditions such that said animal genome is edited and stable;
c) said animal producing progeny that inherit said edited genome.

11. The method of claim 10, wherein said animal is selected from insects and vertebrate animals.

12. The method of claim 10, wherein said animal is an insect.

13. The method of claim 10, wherein said animal is a mosquito.

14. The method of claim 10, wherein said animal is selected from the group consisting of fish, frogs, lizards, birds and monotremes.

15. The method of claim 10, wherein said gene editing is selected from the group consisting of deleting a nucleic acid molecule and/or inserting a nucleic acid molecule.

16. The method of claim 10, wherein said gene editing system is selected from the group consisting of CRISPR/Cas, TALENs and Zinc Finger Nuclease systems.

17. The method of claim 10, wherein said gene editing system comprises a CRISPR/Cas editing system.

18. The method of claim 17, wherein said molecule of interest is Cas.

19. A method of increasing the number of gene edited mosquitoes, the method comprising,
a) injecting into one or more vitellogenic female mosquitos of a population a functional fragment of a yolk protein precursor (YPP) linked to one or more molecules of interest,
wherein the YPP is a Drosophila Yolk Protein 1 (YP1), and wherein the functional fragment has 100% sequence identity to SEQ ID NO: 2 or SEQ ID NO: 3 and is capable of targeting the one or more molecules of interest to an oocyte, and wherein the one or more molecules of interest comprise at least one molecule of a gene editing system;
b) delivery of said molecule of interest to said oocyte of said mosquito;
c) said molecule of interest delivered at 30 hours or less post blood meal feeding of said mosquito or delivered with chloroquine in an amount of 0.5 to 1 mM of chloroquine, or both;
d) editing one or more sequences of said mosquito populations, wherein an increased number of gene edited mosquitoes are produced compared to a method which does not use step a).

20. The method of claim 19 wherein said molecule of interest comprises a Cas peptide.

21. The method of claim 19 wherein the genome of said oocyte is edited such that said mosquito cannot produce viable progeny.

22. The method of claim 19, wherein said molecule of interest is a molecule that produces in said mosquito a disabling or lethal condition.

* * * * *